(12) United States Patent
Rao et al.

US009642922B2

(10) Patent No.: US 9,642,922 B2
(45) Date of Patent: May 9, 2017

(54) CASPASE-TRIGGERED NANO-AGGREGATION PROBES AND METHODS OF USE

(71) Applicant: The Board of Trustees of the Leland Stanford Junior University, Palo Alto, CA (US)

(72) Inventors: Jianghong Rao, Sunnyvale, CA (US); Deju Ye, Mountain View, CA (US); Adam Shuhendler, Palo Alto, CA (US); Frederick Te-Ning Chin, Sunnyvale, CA (US); Jongho Jeon, Palo Alto, CA (US); Bin Shen, Mountain View, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 87 days.

(21) Appl. No.: 14/464,111

(22) Filed: Aug. 20, 2014

(65) Prior Publication Data

US 2015/0056137 A1 Feb. 26, 2015

Related U.S. Application Data

(60) Provisional application No. 61/869,223, filed on Aug. 23, 2013.

(51) Int. Cl.
| | | |
|---|---|---|
| *A61K 51/00* | (2006.01) | |
| *A61M 36/14* | (2006.01) | |
| *A61K 49/00* | (2006.01) | |
| *A61K 49/08* | (2006.01) | |
| *G01N 33/50* | (2006.01) | |
| *A61K 49/10* | (2006.01) | |
| *A61K 51/04* | (2006.01) | |

(52) U.S. Cl.
CPC ...... *A61K 49/0002* (2013.01); *A61K 49/0021* (2013.01); *A61K 49/0032* (2013.01); *A61K 49/0041* (2013.01); *A61K 49/0052* (2013.01); *A61K 49/085* (2013.01); *A61K 49/101* (2013.01); *A61K 51/0455* (2013.01); *G01N 33/5005* (2013.01); *G01N 2333/96469* (2013.01); *G01N 2510/00* (2013.01)

(58) Field of Classification Search
CPC ............... A61K 49/00; A61K 49/0002; A61K 49/0021; A61K 49/0032; A61K 49/0041; A61K 49/0052; A61K 49/085; A61K 49/1011; A61K 51/00; A61K 51/0455; G01N 33/5005; G01N 2333/96469; G01N 2510/00; C07D 277/62; C07D 215/00
USPC ....... 424/1.121, 1.65, 1.69, 1.81, 1.85, 1.89, 424/9.1, 9.3, 9.4, 9.5, 9.6, 1.11, 9.2; 514/1, 1.1; 530/300; 548/241; 546/152
See application file for complete search history.

(56) References Cited

U.S. PATENT DOCUMENTS 7,951,550 B2 * 5/2011 Cali ..................... C07D 277/66
435/25

* cited by examiner

*Primary Examiner* — D L Jones
(74) *Attorney, Agent, or Firm* — Thomas | Horstemeyer, LLP

(57) ABSTRACT

Provided is an activatable probe that undergoes intramolecular cyclization and subsequent aggregation in apoptotic tumor cells upon peptidase-initiated, and most advantageously caspase-3, activation. These caspase-sensitive nano-aggregation probes (C-SNAFs) are generally biocompatible, possess NIR spectral properties or may serve as PET or MRI imaging agents, and have a mechanism of target-mediated nanostructure self-assembly amenable to in vivo use. The probes encompass biocompatible condensation chemistry products that comprise D-cysteine and 2-cyano-6-hydroxy-quinoline (CHQ) moieties linked to an amino-luciferin scaffold, and which can be activated by a two-step reaction requiring caspase-3/7-mediated cleavage of an aspartate-glutamate-valine-aspartate (L-DEVD) capping peptide and the free intracellular thiol-mediated reduction of the disulfide bond.

19 Claims, 41 Drawing Sheets

Control probes
L-ctrl (R₁ = L-Ac-DEVD)
D-ctrl (R₁ = D-Ac-DEVD)

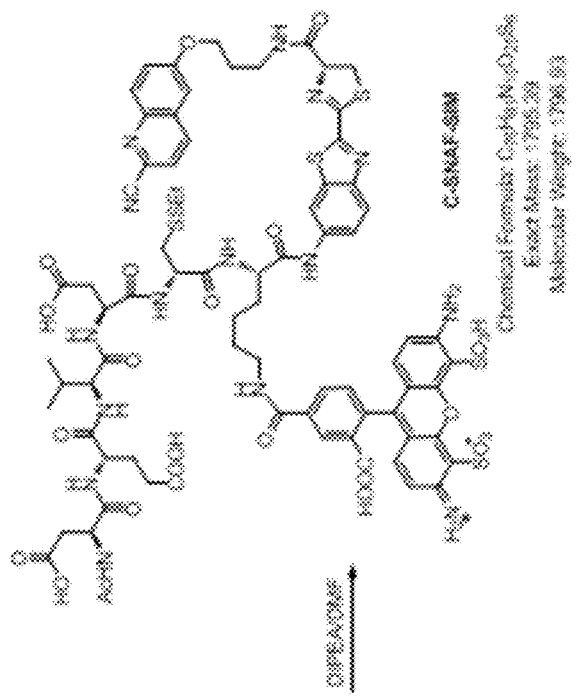
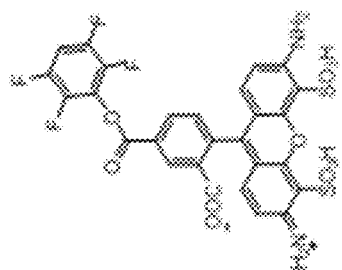
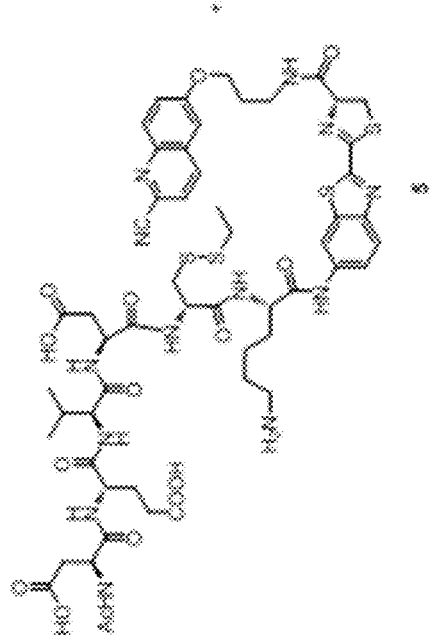
Fig. 6

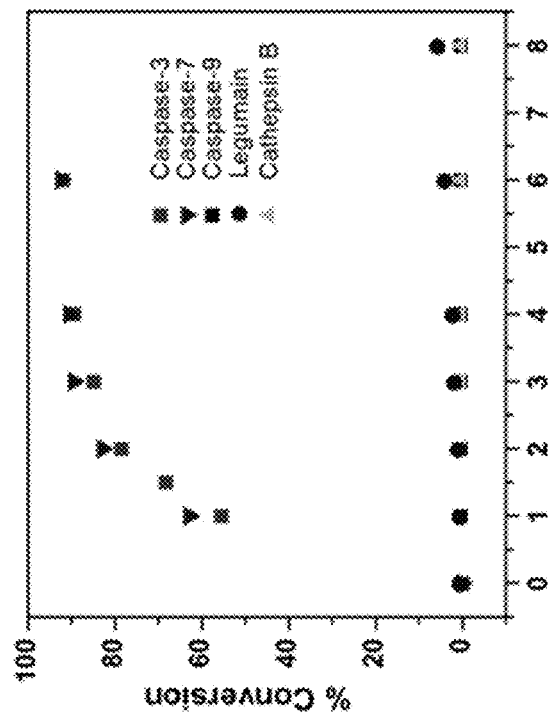
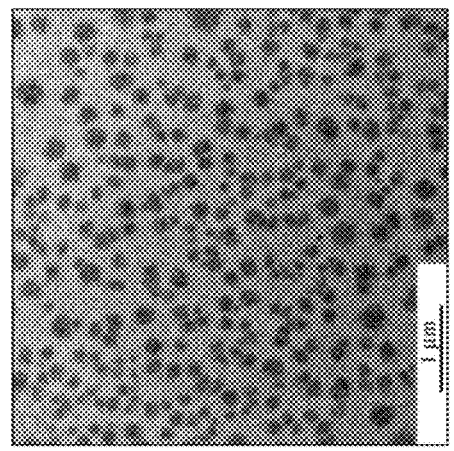

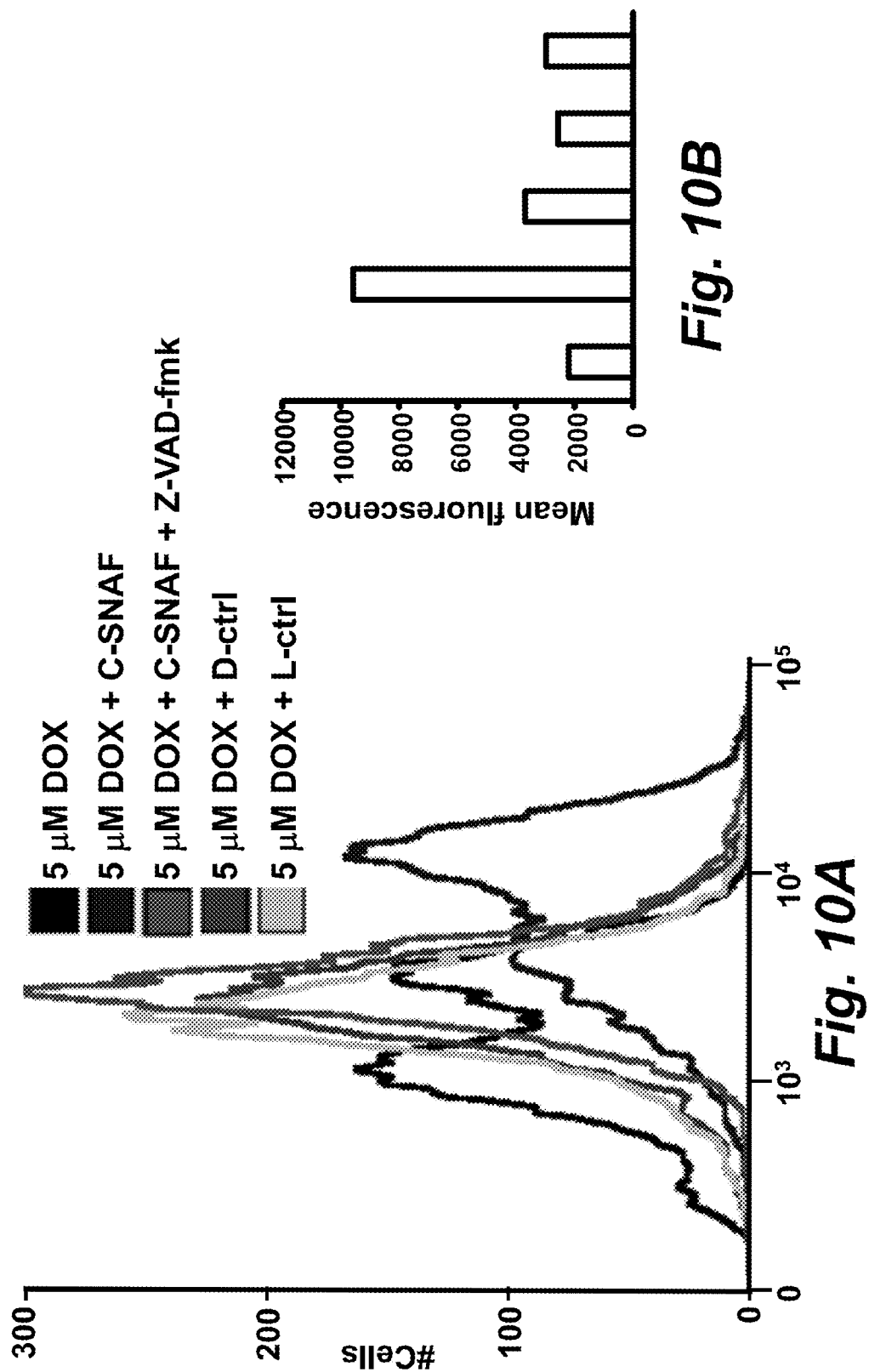

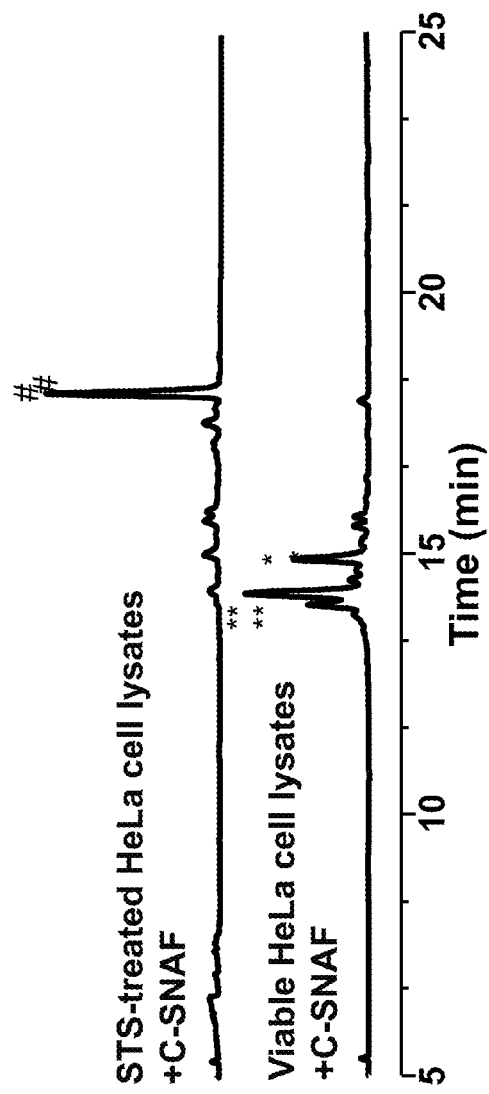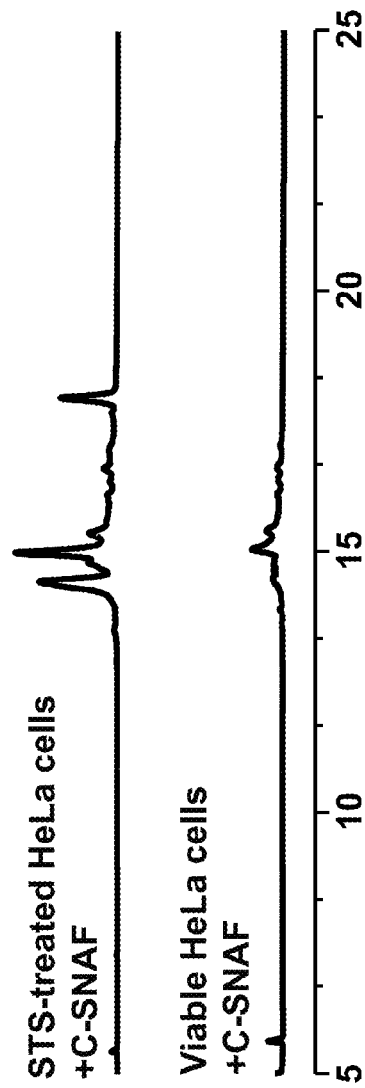
Fig. 12A
Fig. 12B

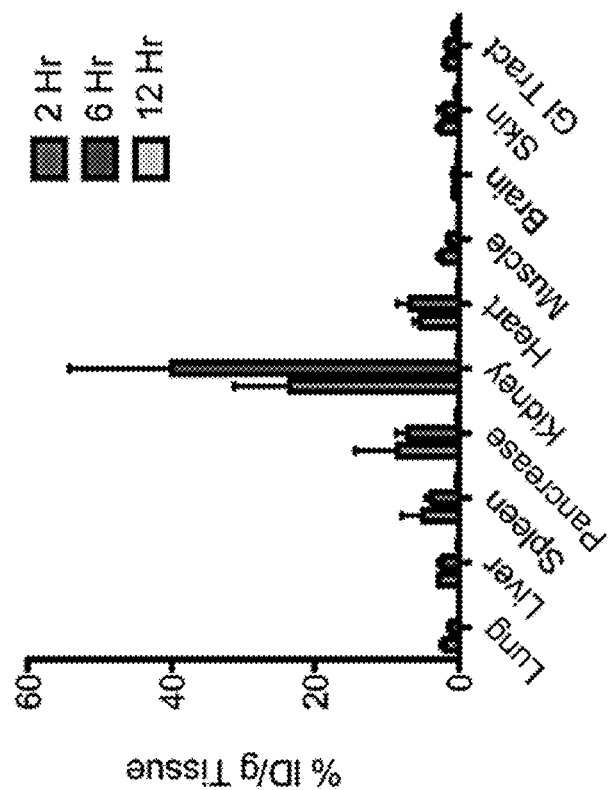
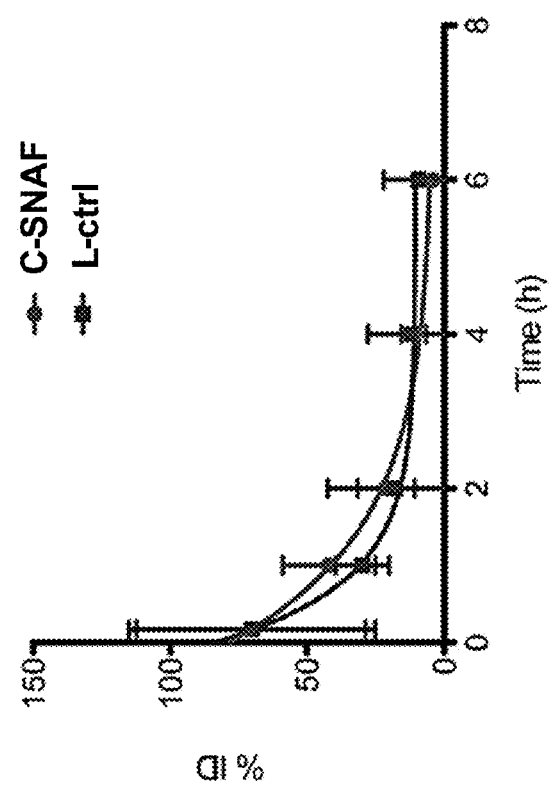
Fig. 14B
Fig. 14A

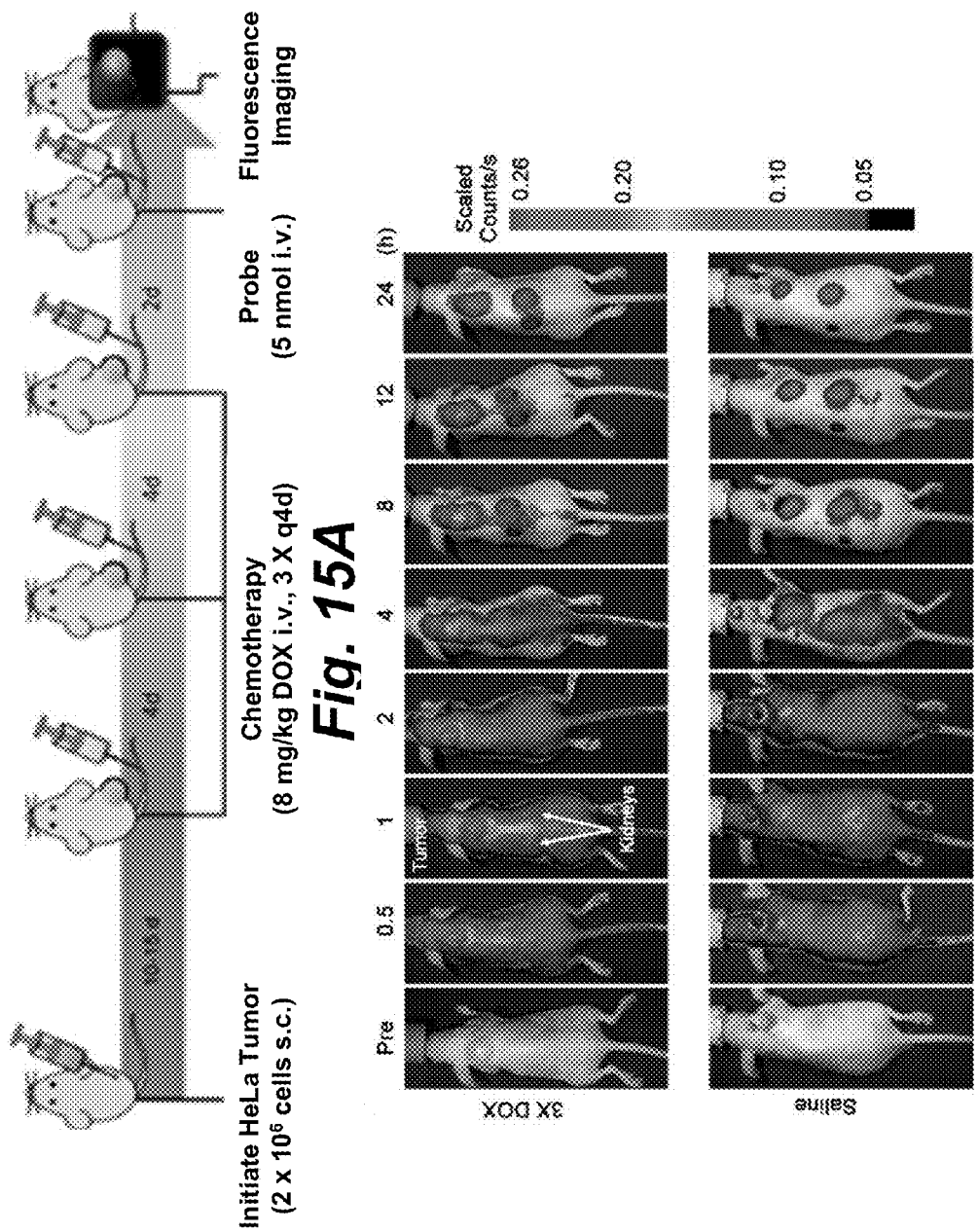

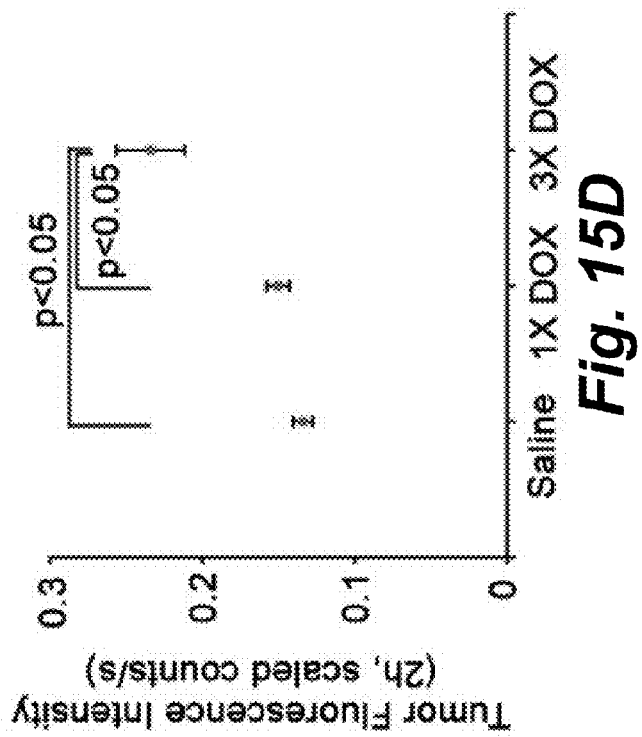
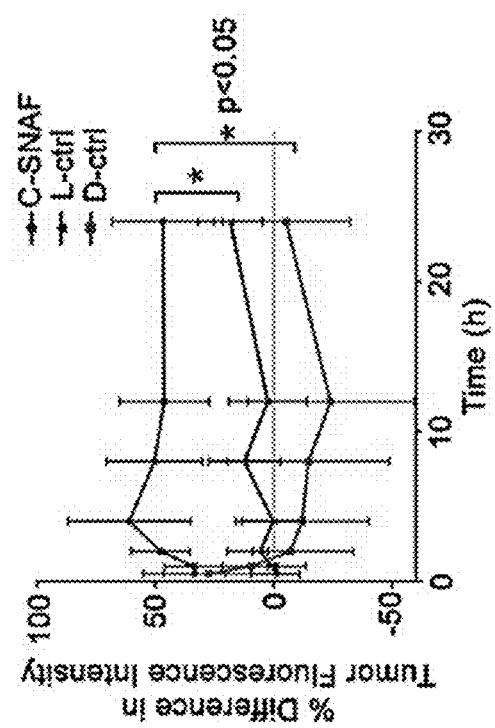
Fig. 15D
Fig. 15C

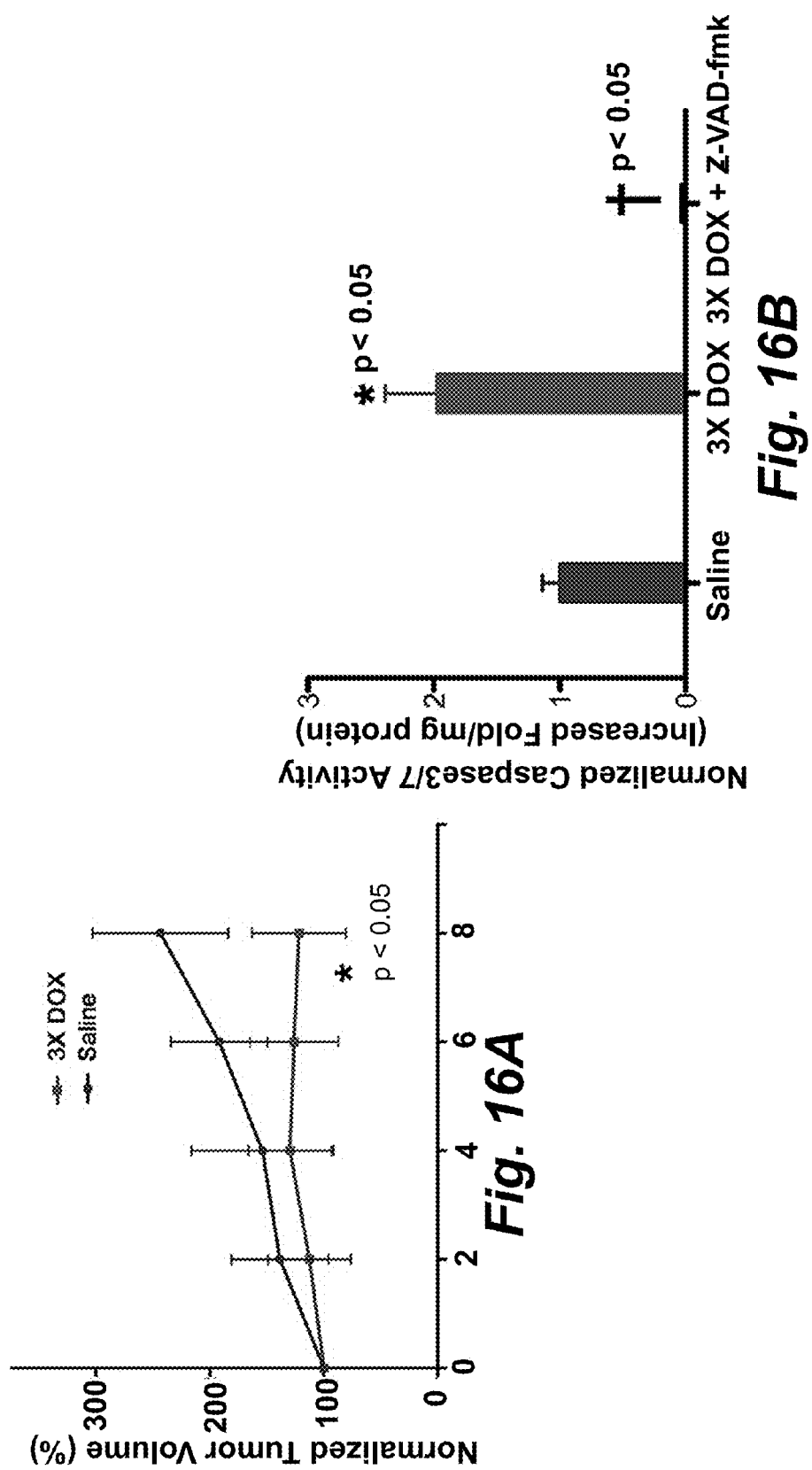

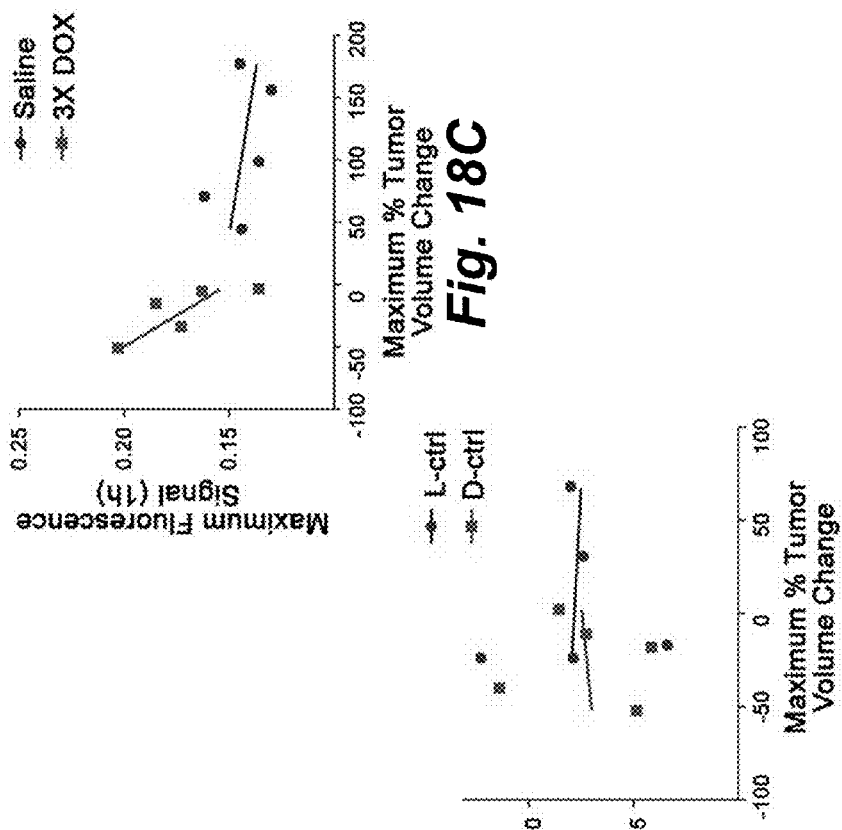
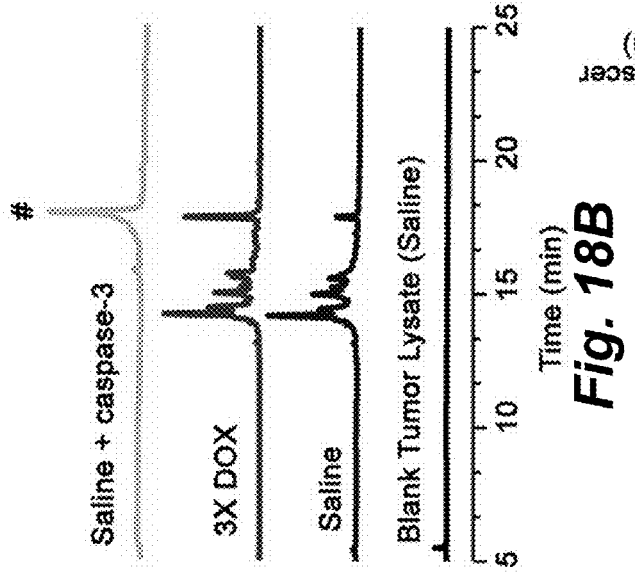
Fig. 18B
Fig. 18C
Fig. 18D

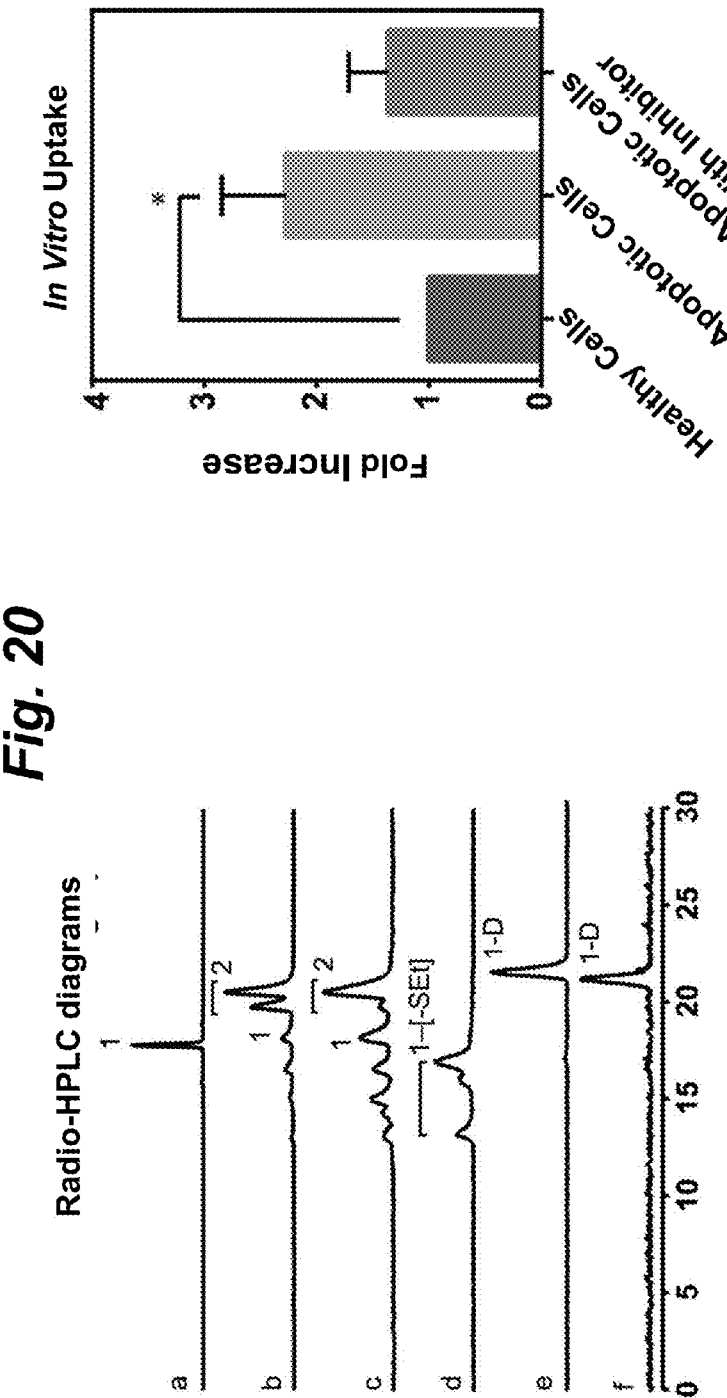
Fig. 20
Fig. 21A
Fig. 21B

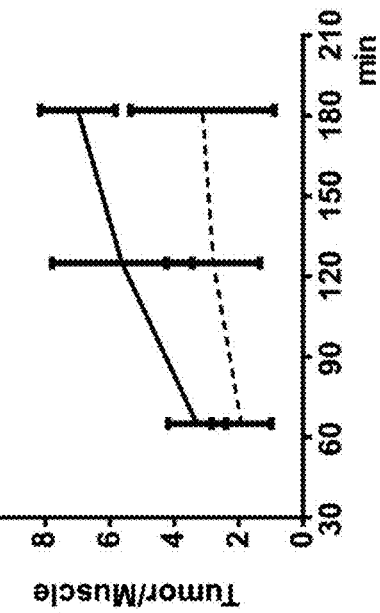
Fig. 23B
Fig. 23C
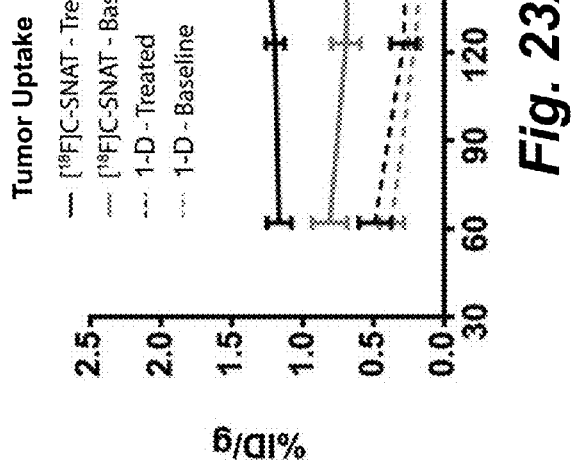
Fig. 23A

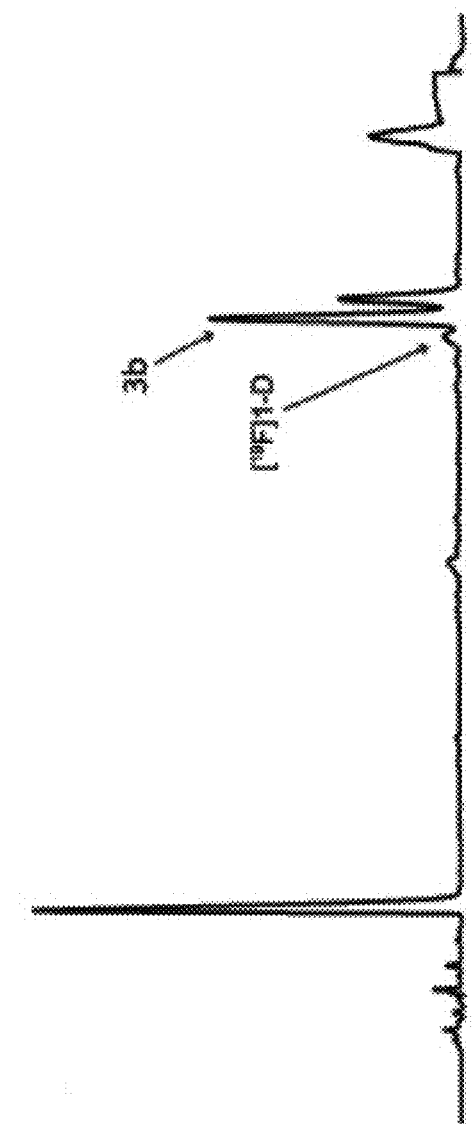
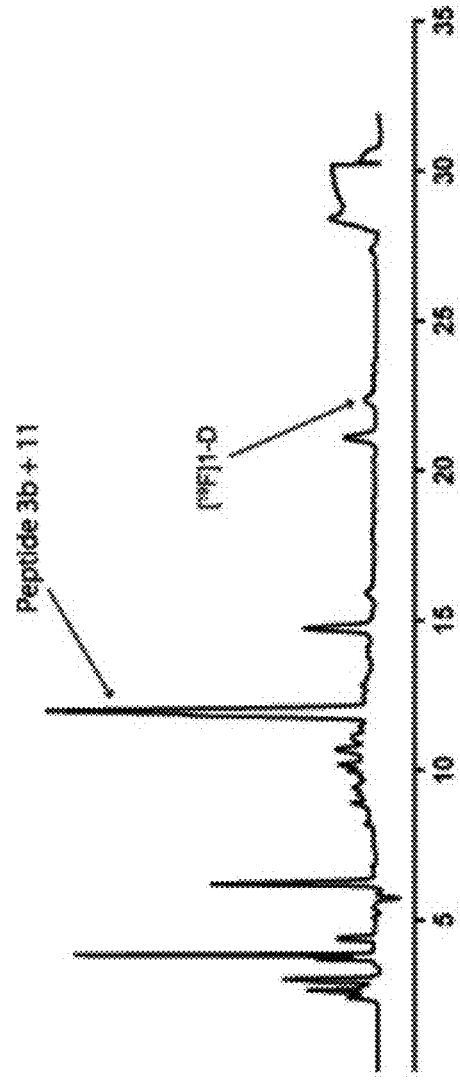
Fig. 24A
Fig. 24B

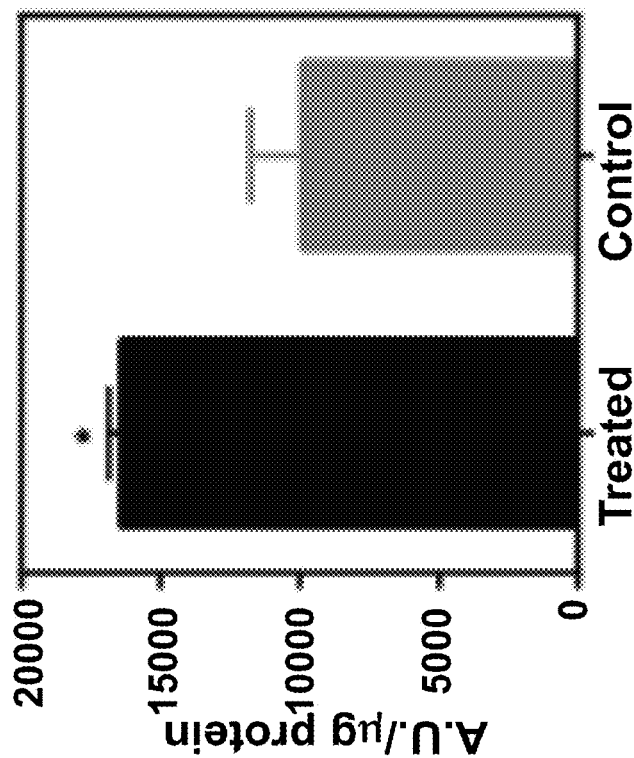
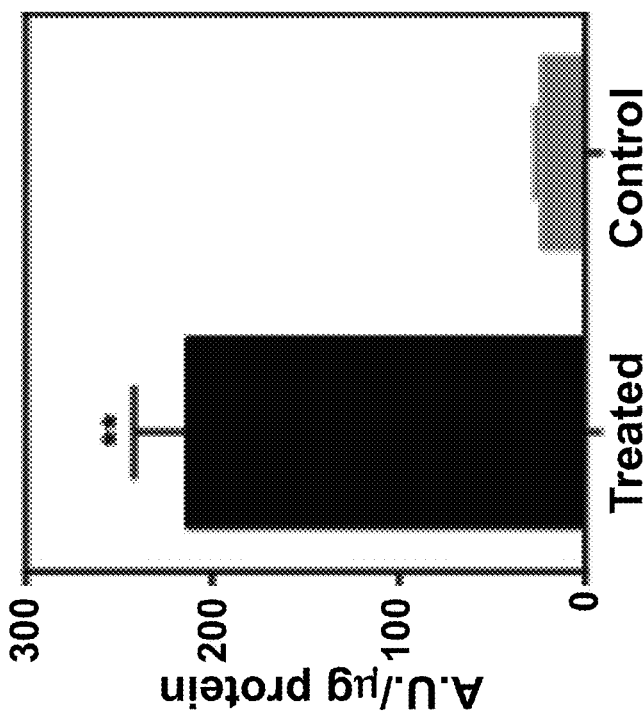
Fig. 26A
Fig. 26B

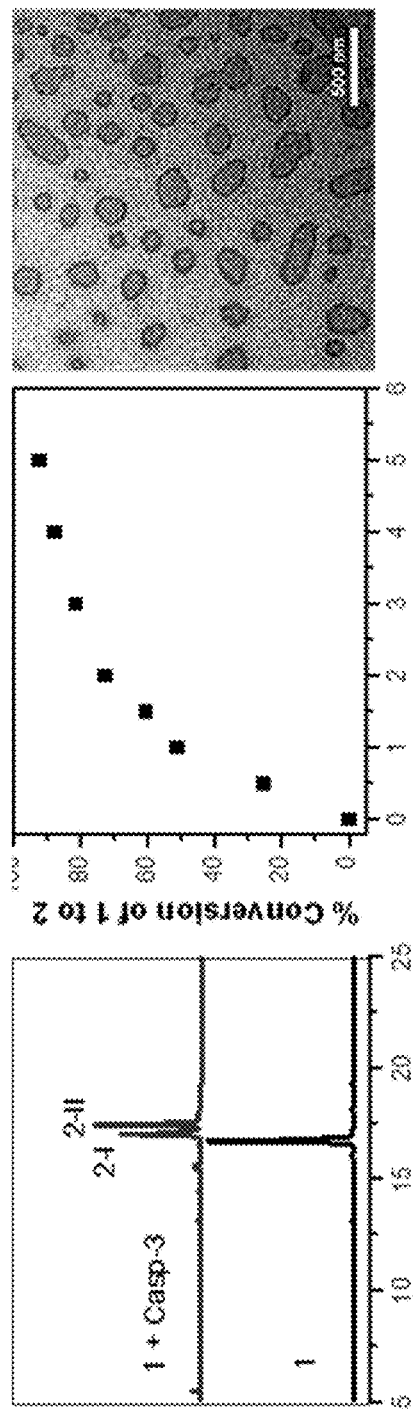
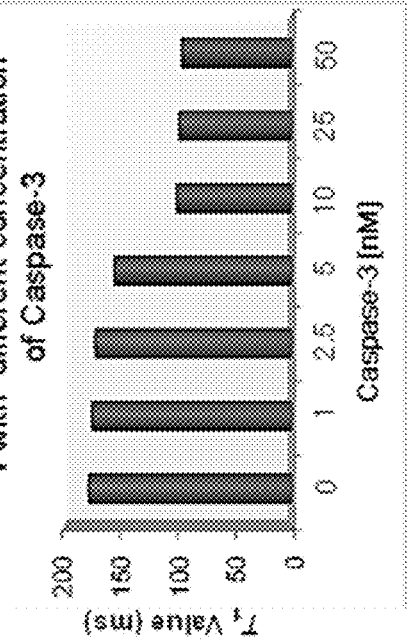
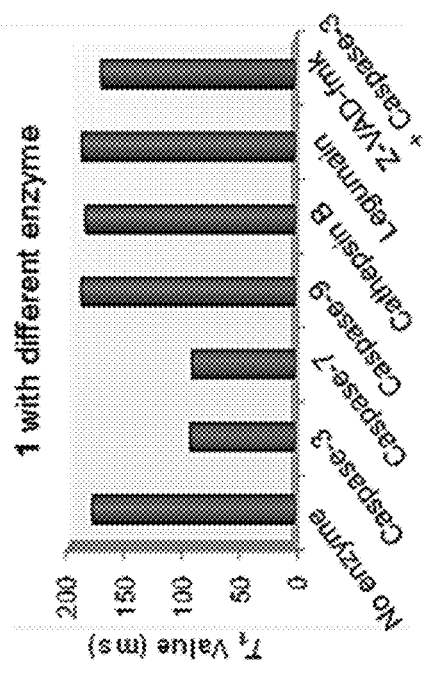
Fig. 27A
Fig. 27B
Fig. 27C
Fig. 27D
Fig. 27E

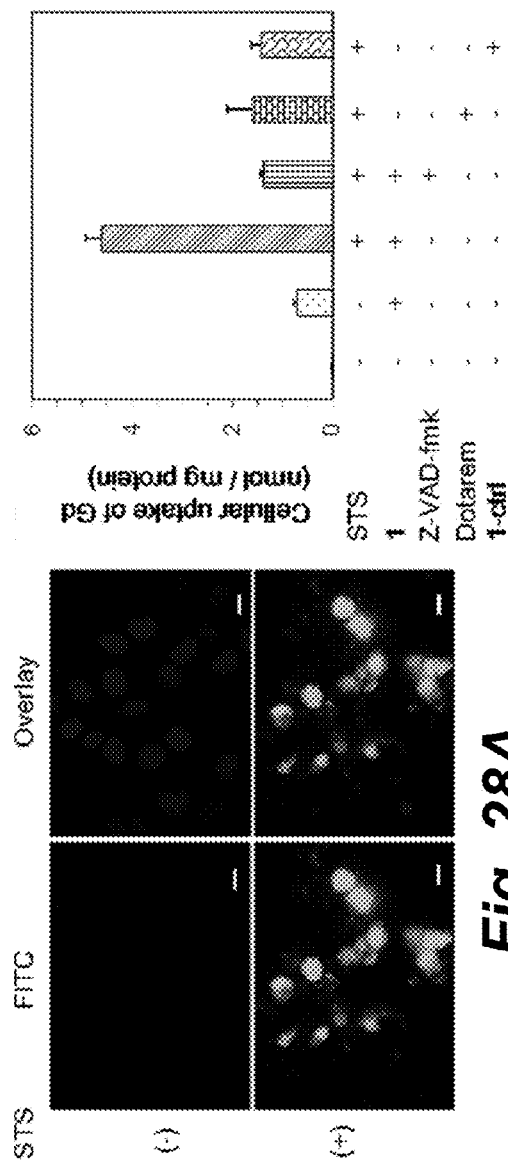
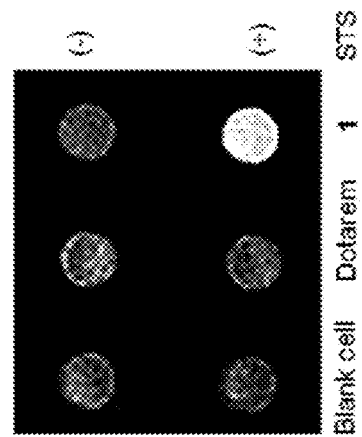
Fig. 28A
Fig. 28B
Fig. 28C
Fig. 28D

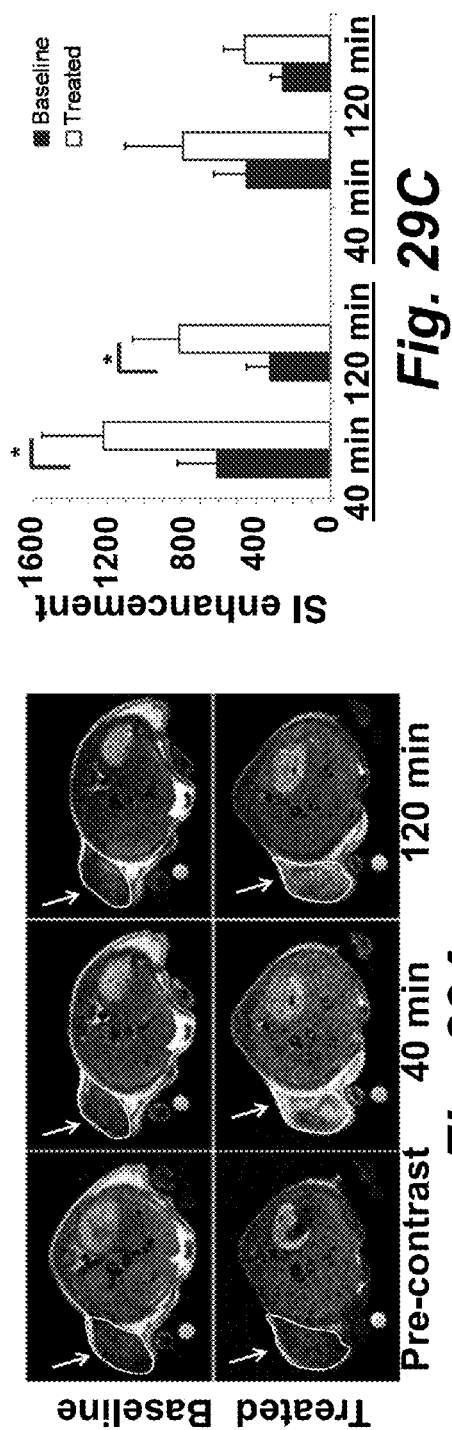
Fig. 29A
Fig. 29C
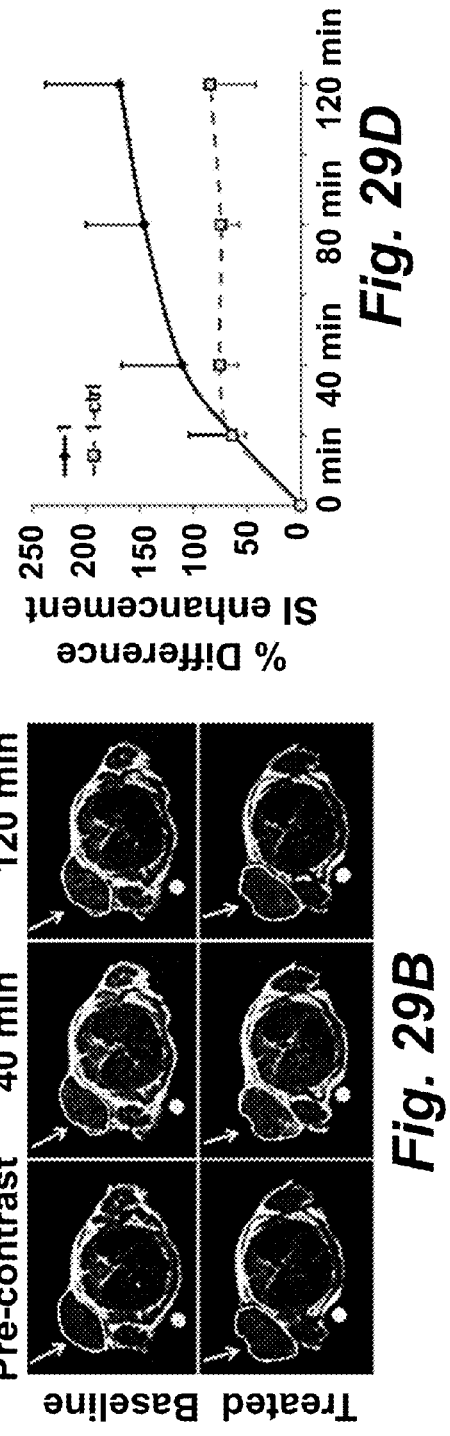
Fig. 29B
Fig. 29D

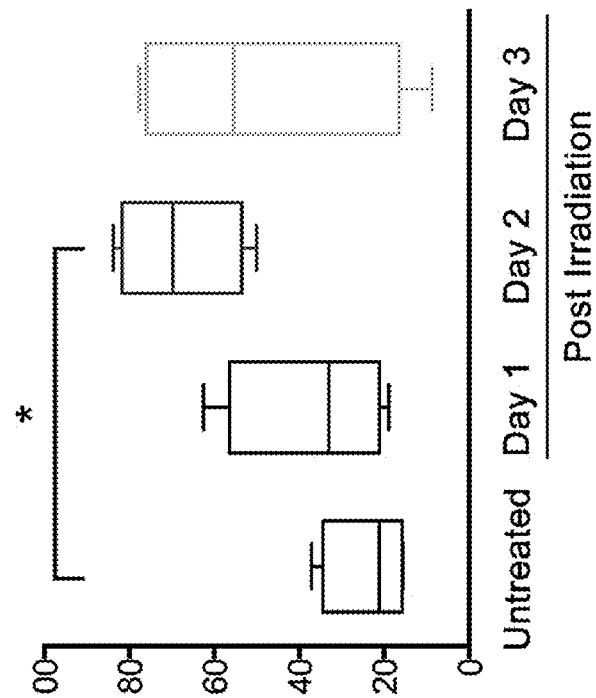
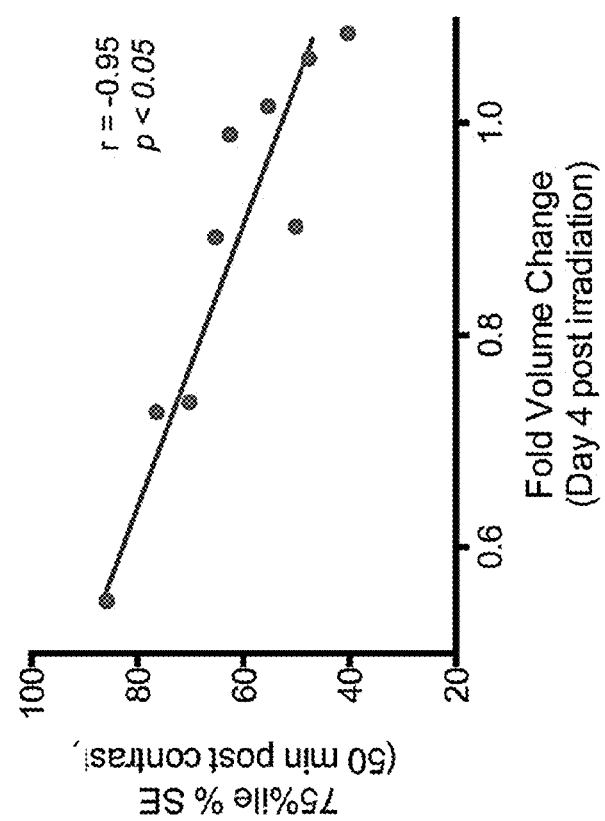
Fig. 34B
Fig. 34A

CASPASE-TRIGGERED NANO-AGGREGATION PROBES AND METHODS OF USE

CROSS-REFERENCE TO RELATED APPLICATIONS

This application claims priority to U.S. Provisional Patent Application Ser. No. 61/869,223 entitled "CASPASE-TRIGGERED NANO-AGGREGATION PROBES AND METHODS OF USE" filed on Aug. 23, 2013, the entirety of which is hereby incorporated by reference.

STATEMENT REGARDING FEDERALLY SPONSORED RESEARCH OR DEVELOPMENT

This invention was made with government support under contracts CA114747 and CA151459 awarded by the National Institutes of Health. The government has certain rights in this invention.

FIELD OF THE DISCLOSURE

The present disclosure relates to caspase-triggered self-assembling nano-aggregation probes for the detection of apoptotic cells and tissues. The present disclosure further relates to methods of detecting and imaging cells and tissues that are apoptotic.

BACKGROUND

Controlling small molecules to self-assemble into supra-molecular complexes is pervasive among living things, which build complex structures for high-order functions necessary for life (Whitesides et al., (1991) Science. 254: 1312-1319; Capito et al., (2008) Science 319: 1812-1816). In the laboratory, this principle of self-assembly is also widely used to synthesize supramolecules and nano/microstructures (O'Leary et al., (2011) Nat. Chem. 3: 821-828; Gazit, E. (2010) Nat. Chem. 2: 1010-1011; Yang et al., (2008) Acc. Chem. Res. 41: 315-326). Recently, extensive efforts have been made to design and control small molecules with the propensity to self-assemble in living cells (Liang et al., (2010) Nat. Chem. 2: 54-60; Gao et al., (2012) Nat. Commun. 3: 1033; Adler-Abramovich et al., (2012) Nat. Chem. Biol. 8: 701-706; Williams et al., (2011) Biomaterials 32: 5304-5310; Ye et al., (2011) Angew. Chem. Int. Ed. 50: 2275-2279). In these examples, membrane-permeable small molecules are shown to enter cells and undergo self-assembly after activation by intended cellular targets, such as an enzyme. This recent progress has already generated promising applications such as imaging a proteolytic enzyme activity in subcellular locations, and has provided possible means to investigate and control self-assembly in the context of living cells. Further advances in achieving controlled self-assembly of small molecules in whole mammalian organisms would offer myriads of applications in biology and medicine such as controlled drug delivery (Vemula et al., (2011) J. Biomed. Mater. Res. A 97: 103-110), synthesis of new functional molecules, new ways for regulating cellular processes and molecular imaging in living subjects. Unfortunately, there are no previous examples of controlled self-assembly of synthetic small molecules at the level of whole mammalian organisms. The in vivo physiological environment—a much more complex and dynamic setting than cultured cells—demands high bioorthogonality and biocompatibility of the chemistry that controls self-assembly, and also presents significant challenges to characterize such a system.

Currently, a number of biocompatible reactions including Staudinger ligation (Saxon & Bertozzi (2000) Science 287: 2007-2010; Lin et al., (2005) J. Am. Chem. Soc. 127: 2686-2695), strain-promoted azide-alkyne cycloaddition 14,15, trans-cyclooctene/tetrazine cycloaddition (Devaraj et al., (2009) Angew. Chem. Int. Ed. 48: 7013-7016; Blackman et al., (2008) J. Am. Chem. Soc. 130: 13518-13519; Lang et al., (2012) Nat. Chem. 4: 298-304), and Pictet-Spengler ligation (Agarwal et al., (2013) Proc. Natl. Acad. Sci. U.S.A. 110: 46-51), have been developed for probing biological interactions in living systems, some of which have been shown to work in cells (Yusop et al., (2011) Nat. Chem. 3: 239-243; Chan et al., (2012) Nat. Chem. 4: 973-984), but very few can work in living organisms (Prescher et al., (2004) Nature 430: 873-877; Laughlin et al., (2008) Science 320: 664-667; Devaraj et al., (2012) Proc. Natl. Acad. Sci. U.S.A. 109: 4762-4767; Sletten & Bertozzi (2011) Acc. Chem. Res. 44: 666-67622-25). A new biocompatible reaction between free cysteine and cyanobenzothiazole (CBT) has been reported that can proceed in physiological conditions with a fast second-order rate constant $(9.1\ M^{-1}s^{-1})$ (Ren et al., (2009) Angew. Chem. Int. Ed. 48: 9658-9662; Van de Bittner et al., (2013) J. Am. Chem. Soc. 135: 1783-1795). This reaction has been successfully applied to protein labelling (Devaraj et al., (2012) Proc. Natl. Acad. Sci. U.S.A. 109: 4762-4767) and protease activity imaging in living cells (Liang et al., (2010) Nat. Chem. 2: 54-60).

Recently, a few radiolabeled sulfonamide small-molecule caspase-3 inhibitors have been reported for PET imaging of caspase-3 in apoptotic cells (Nguyen et al., (2009) Proc. Natl. Acad. Sci. USA 106: 16375-16380; Zhou et al., (2009) Org. Biomol. Chem. 7: 1337-1348; Faust et al., (2007) J. Nucl. Med. Mol. Imaging. 51: 67-73; Reshef et al., (2010) J. Nucl. Med. 51: 837-840). However, a PET tracer that is mechanistically similar to the activatable fluorescent probes and can image caspase-3 activity with signal amplification has not been reported.

MRI probes that can specifically report on enzyme activity have become particularly attractive due to variations in enzyme expression levels in many diseases. The inherently low detection sensitivity of MRI has limited the development of enzyme activatable MRI probes for in vivo application. However, novel activatable MRI probes enable can high spatial resolution imaging of specific enzyme activity in vivo and are thus in high demand.

Recently, an activatable thulium-based paramagnetic chemical exchange saturation transfer (PARACEST) MRI probe and a paramagnetic relaxation-based $^{19}F$ MRI probe have been reported to detect caspase-3 activity with high sensitivity in solution. However, a probe responsive to caspase-3 that employs gadolinium, one of the major clinically used sources of MRI contrast, has not yet been reported.

SUMMARY

The disclosure provides embodiments of the synthesis, radiolabeling and biological applications of an activatable tracer that undergoes intramolecular cyclization and aggregation in apoptotic tumor cells upon caspase-3 activation. The aggregated nanoprobes of the disclosure may be detectable optically, by PET detection, magnetic resonance imaging, and the like depending on the detectable reporter attached to the nanoprobe.

One aspect of the disclosure, therefore, encompasses embodiments of an activatable probe comprising a detachable capping moiety conjugated to a self-cyclizing molecule comprising a cysteine moiety, a 2-cyano-6-hydroxyquinoline moiety, an amino luciferin scaffold, and a detectable imaging moiety.

In some embodiments of this aspect of the disclosure, the activatable probe can have the formula II, III, or IV:

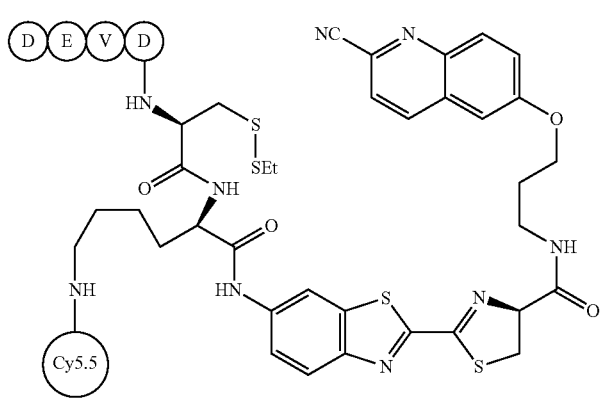

II

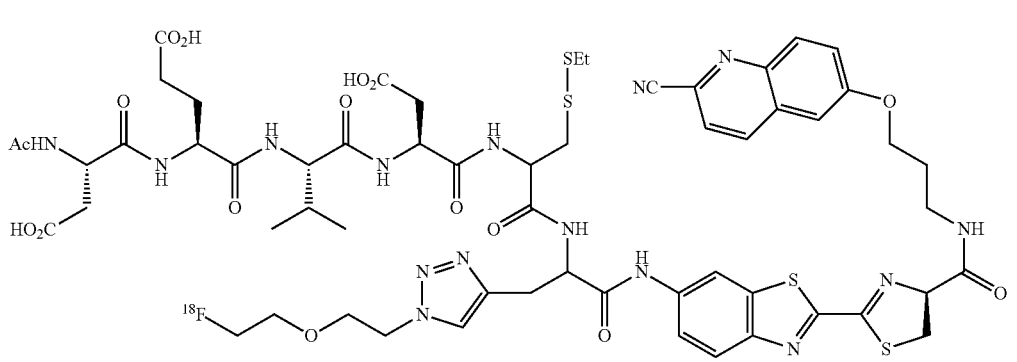

III

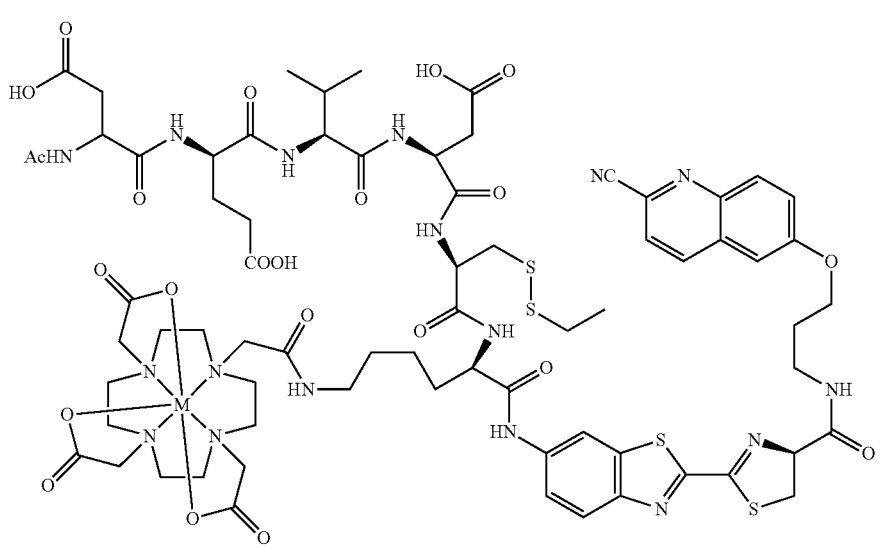

IV

Another aspect of the disclosure encompasses embodiments of a pharmaceutically acceptable composition comprising an activatable probe according to the disclosure and a pharmaceutically acceptable carrier.

Yet another aspect of the disclosure encompasses embodiments of a nano-aggregation probe, wherein said nanoprobe is an aggregate of an activated probe, wherein said activated probe comprises a self-cyclized molecule having the formula I and a detectable imaging moiety, wherein the detectable probe is a fluorophore or a radionuclide.

Still another aspect of the disclosure encompasses embodiments of a method of forming a nano-aggregation probe comprising delivering to an apoptotic cell a pharmaceutically acceptable composition comprising an activatable probe, wherein said activatable probe can comprise a detachable capping moiety conjugated to a self-cyclizing molecule, said self-cyclizing molecule comprising a cysteine moiety, a 2-cyano-6-hydroxyquinoline moiety, an amino luciferin scaffold, and a detectable imaging moiety, wherein the detachable capping moiety has the amino acid sequence L-aspartate-glutamate-valine-aspartate and is selectively cleavable from the self-cyclizing molecule by caspase 3/7, whereupon the activatable probe can enter the apoptotic cell, an apoptopically-induced caspase 3/7 cleaves the detachable capping moiety from the activatable probe, and said probe aggregates to form the nano-aggregation probe.

Still yet another aspect of the disclosure encompasses embodiments of a method of detecting an apoptotic cell, the method comprising the steps of: (i) delivering to the cytoplasm of an animal cell a pharmaceutically acceptable composition comprising an activatable probe, wherein said activatable probe comprises a detachable capping moiety conjugated to a self-cyclizing molecule, said self-cyclizing molecule comprising a cysteine moiety, a 2-cyano-6-hydroxyquinoline moiety, an amino luciferin scaffold, and a detectable imaging moiety, wherein the detachable capping moiety has the amino acid sequence L-aspartate-glutamate-valine-aspartate and is selectively cleavable from the self-cyclizing molecule by caspase 3/7, whereupon the activatable probe enters the apoptotic cell, an apoptopically-induced caspase 3/7 cleaves the detachable capping moiety from the activatable probe, and said probe aggregates to form a nano-aggregation probe; and (ii) detecting the nano-aggregation probe, thereby determining that the animal cell recipient of the activatable probe is apoptotic.

In some embodiments of this aspect of the disclosure, the detectable imaging moiety is a fluorophore and step (ii) can further comprise irradiating the recipient cell with an incident exciting energy, electronically detecting an emitted fluorescence, and measuring the intensity of said emission and optionally generating an image of the fluorescence.

In some embodiments of this aspect of the disclosure, the detectable imaging moiety is detectable by positron electron transmission and step (ii) can further comprise detecting the nano-aggregation probe by PET imaging.

BRIEF DESCRIPTION OF THE DRAWINGS

Many aspects of the disclosure can be better understood with reference to the following drawings.

FIG. 1A shows the caspase-3/7 and reduction-controlled conversion of C-SNAF to C-SNAF-cycl through the bioorthogonal intramolecular cyclization reaction, followed by self-assembly into nano-aggregates in situ.

FIG. 1B illustrates that the fate of C-SNAF in vivo is dependent upon the tumor response to chemotherapy. Following intravenous administration, C-SNAF extravasates into tumor tissue due to its small size. In live tumor tissue that is not responding to applied chemotherapy, the pro-caspase-3 is inactive, and the DEVD capping peptide remains intact. C-SNAF can freely diffuse away from live tumor tissue, leading to low fluorescence. In apoptotic tumor tissue, pro-caspase-3 is converted to active caspase-3. C-SNAF can readily enter dying cells due to the loss of plasma membrane integrity associated with apoptosis. After DEVD cleavage by active caspase-3 and disulfide reduction, C-SNAF undergoes macrocyclization and in situ nano-aggregation, leading to enhanced probe retention and high fluorescence.

FIG. 1C illustrates the chemical structures of control probes L-ctrl and D-ctrl.

FIG. 6 illustrates a scheme for the synthesis of probe C-SNAF-SIM.

FIGS. 7A-7C illustrate the in vitro characterization of caspase-3/7-sensitive nano-aggregation fluorescent probe (C-SNAF) of the disclosure.

FIG. 7A shows HPLC traces of C-SNAF in water (TR=15.8 min) and the incubation of C-SNAF (25 μM) with recombinant human caspase-3 (4.9×10-3 μml) for 24 h at 37° C. in caspase-3 buffer (TR=17.7 min).

FIG. 7B illustrates the enzymatic reaction kinetics and specificity studies by longitudinal monitoring of the percentage conversion of C-SNAF (25 μM) to C-SNAF-cycl after incubation with equal masses (0.735 μg/ml) of recombinant human caspase-3, caspase-7, caspase-9, cathepsin B, and legumain, respectively.

FIG. 7C is a digital TEM image of nano-aggregates after incubation C-SNAF (50 μM) with recombinant human caspase-3 ($4.9 \times 10^{-3}$ U/mL) overnight at 37° C. in caspase-3 buffer; scale bar, 1 μm.

FIG. 10A illustrates that overlay histograms obtained by flow cytometry analysis that show C-SNAF, but not control probes L-ctrl nor D-ctrl, can efficiently label DOX-induced apoptotic cells. Cells treated with caspase-3 inhibitor were not labeled by C-SNAF. Cells were treated with 5 μM DOX, or co-incubated with 5 μM DOX and 2 μM C-SNAF, L-ctrl, D-ctrl, or 2 μM C-SNAF together with 50 μM caspase inhibitor Z-VAD-fmk for 24 h.

FIG. 10B illustrates the quantitation of the fluorescent intensity of Cy5.5 in cells derived from the flow cytometry analysis shown in FIG. 10A and shows that 5 μM DOX-induced apoptotic cells incubated with C-SNAF (blue) have approximately a 4-fold increased intensity compared to that without incubation or incubation with L-ctrl or D-ctrl. The labeling of apoptotic cells with C-SNAF was blocked by the caspase inhibitor.

FIG. 11A illustrates a flow cytometry analysis of viable and STS-induced apoptotic HeLa cells after incubation with C-SNAF (2 μM), C-SNAF (2 μM) with caspase inhibitor Z-VAD-fmk (50 μM), or 2 μM of L-ctrl or D-ctrl. The quadrants Q were defined as Q1=FLICA-negative/Cy5.5-negative, Q2=FLICA-positive/Cy5.5-negative, Q3=FLICA-positive/Cy5.5-positive and Q4=FLICA-negative/Cy5.5-positive.

Representative dot plots show that FLICA-positive apoptotic cells were efficiently labeled by C-SNAF, but not by control probes (L-ctrl and D-ctrl), demonstrating a good correlation between C-SNAF and FLICA.

Figure 11A:
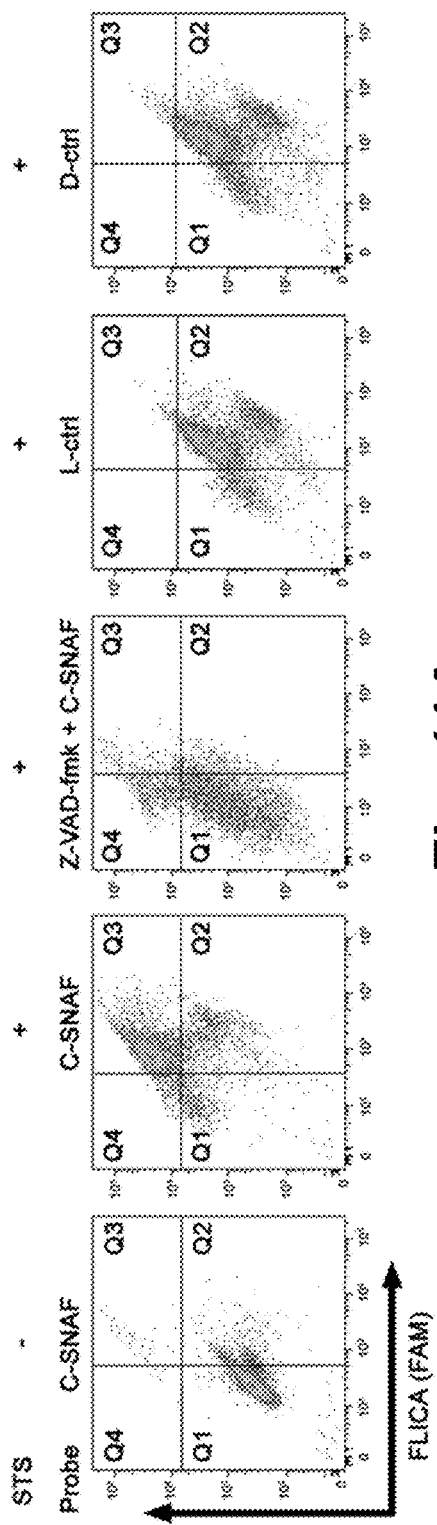
FIGS. 11A and 11B illustrate the imaging of caspase-3/7 activities in STS-treated cancer cells with C-SNAF.
Figure 11B:
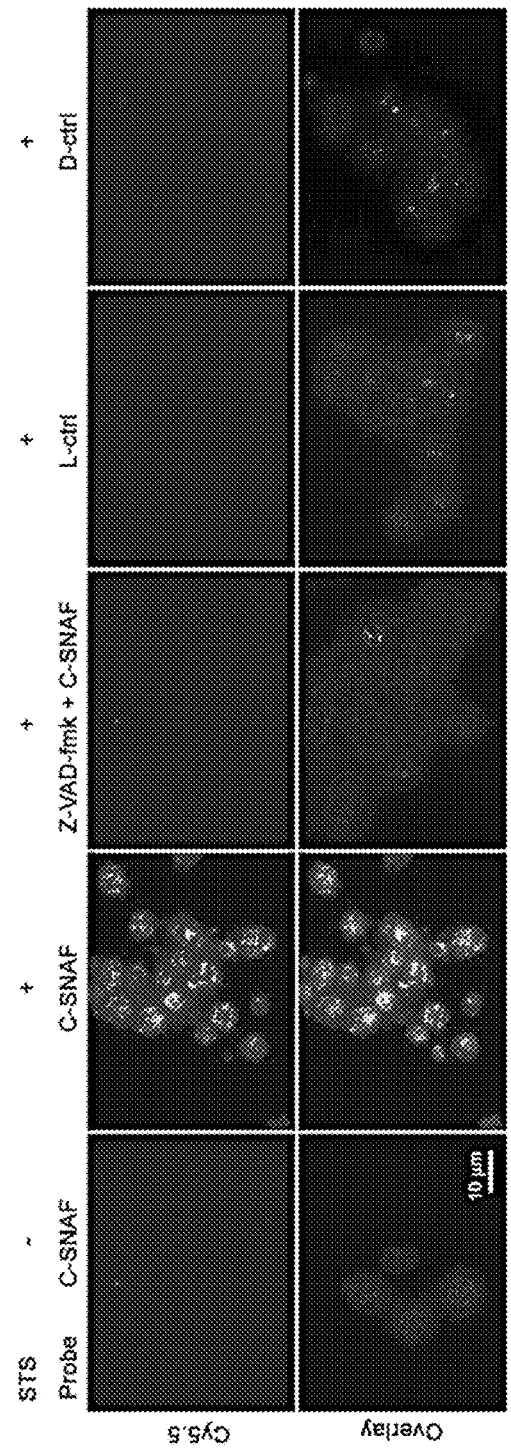

FIG. 11B is a series of digital fluorescence microscopy imaging of C-SNAF (2 μM) labeling STS-induced apoptotic HeLa cells. Cells were stained with nuclear binding probe Hoechst 33342 (blue). An extensive fluorescence was observed only in the apoptotic cells after incubation with C-SNAF, indicating a specifically intracellular accumulation of the probe after caspase-3/7-triggered macrocyclization and nano-aggregation.

FIGS. 12A and 12B illustrate an analysis of caspase-3-triggered intramolecular condensation of C-SNAF in viable and STS (2 μM) treated HeLa cells.

FIG. 12A shows HPLC traces of incubation of C-SNAF (5 μM) in viable and apoptotic HeLa cell lysates overnight at 37° C. HeLa cells (about $8 \times 10^6$) were either untreated or treated with 2 μM STS for 4 h and kept growing in blank culture medium for another 24 h after removal of STS. Cells were then lysed with RIPA buffer, and incubated with C-SNAF (5 μM) followed by analyzing the reaction by HPLC (678 nm UV detection).). Peaks * and ** indicate the disulfide reduction products T1 and T2; peak # indicates the cyclized product C-SNAF-cycl.

FIG. 12B shows HPLC traces of viable and apoptotic HeLa cells incubated with C-SNAF (50 μM) for 24 h. HeLa cells (about $8 \times 10^6$) were untreated or treated with 2 μM STS for 4 h and then incubated with C-SNAF (50 μM) for another 24 h after removal of STS. Cells were then lysed, and analyzed by HPLC assay (675 nm UV detector).

Figure 13:

FIG. 13 illustrates a super-resolution imaging of caspase-3/7-triggered nano-aggregation in apoptotic cells using 3D-SIM. Panel a: Representative 3D-SIM image of self-assembling fluorescent nanoparticles in apoptotic cells incubated with C-SNAF-SIM (2 μM). Cells were co-stained with DAPI (4',6-diamidino-2-phenylindole); Panel b, Enlarged 3D-SIM image of self-assembling nanoparticles in single cell from Panel a. The arrows show the probe accumulated in the apoptotic bodies. The insert box indicates the enlarged area; Panel c, Enlarged 3D-SIM images of self-assembling nanoparticles in 3D-slice in cells. Upper left panel shows XY slices, upper right and lower left panels show orthogonal YZ and XZ views of the processed Z-stack. The box in lower right panel indicates the enlarged area in the cell shown in Panel b. The arrows show the views of representative individual fluorescent dot in XY, YZ, and XZ panels, with a diameter of approximately 150 nm at X or Y dimension.

FIGS. 14A and 14B illustrate the pharmacokinetics of the probes in mice.

FIG. 14A shows the blood circulation study of C-SNAF (5 nmol) and L-ctrl (5 nmol) in healthy nude mice (n=5).

FIG. 14B shows a biodistribution study of C-SNAF in healthy nude mice after intravenous administration of 5 nmol of C-SNAF at 2, 6, and 12 hr.

FIGS. 15A-15D illustrate non-invasive imaging of apoptosis in tumor-bearing mice treated with DOX.

FIG. 15A illustrates an in vivo experimental design outlining HeLa tumor implantation, three rounds of applied DOX chemotherapy (3×DOX), and fluorescence imaging.

FIG. 15B shows longitudinal fluorescence imaging of 3×DOX- (top) and saline-treated (bottom) tumor-bearing mice with C-SNAF (5 nmol). Anatomical locations of the tumor and kidneys are indicated by white arrows.

FIG. 15C is a graph illustrating the percent difference in tumor fluorescence intensity between 3×DOX and saline treatment groups over the course of imaging for C-SNAF (n=5), L-ctrl (n=5), or D-ctrl (n=5). *p<0.05 between groups indicated by brackets.

FIG. 15D illustrates a comparison of the average tumor fluorescence intensity at 2 h after C-SNAF administration in saline-treated mice (n=4), or following a single (1×DOX) or three DOX treatments (3×DOX) in the same animals (n=4). *p<0.05 between groups indicated by brackets.

FIGS. 16A and 16B illustrate the validation of a HeLa tumor xenograft mouse model response to chemotherapy.

FIG. 16A shows the longitudinal monitoring of tumor size changes showing a significant decrease in tumor growth rates for 3×DOX- (n=19) relative to saline-treated (n=15) mice.

FIG. 16B shows the measurement of caspase-3/7 activity levels in tumor lysates, showing an approximately 2-fold increase in 3×DOX- versus saline-treated mice that was inhibited by z-VAD-fmk. *p<0.05 for saline versus 3×DOX treatment, † p<0.05 for 3×DOX versus 3×DOX+z-VAD-fmk, all groups are n=4. These data confirm that the chosen dose and chemotherapeutic administration schedule is suitable for assessment of C-SNAF for monitoring cancer chemotherapeutic response in vivo.

Figures 17A, 17B:
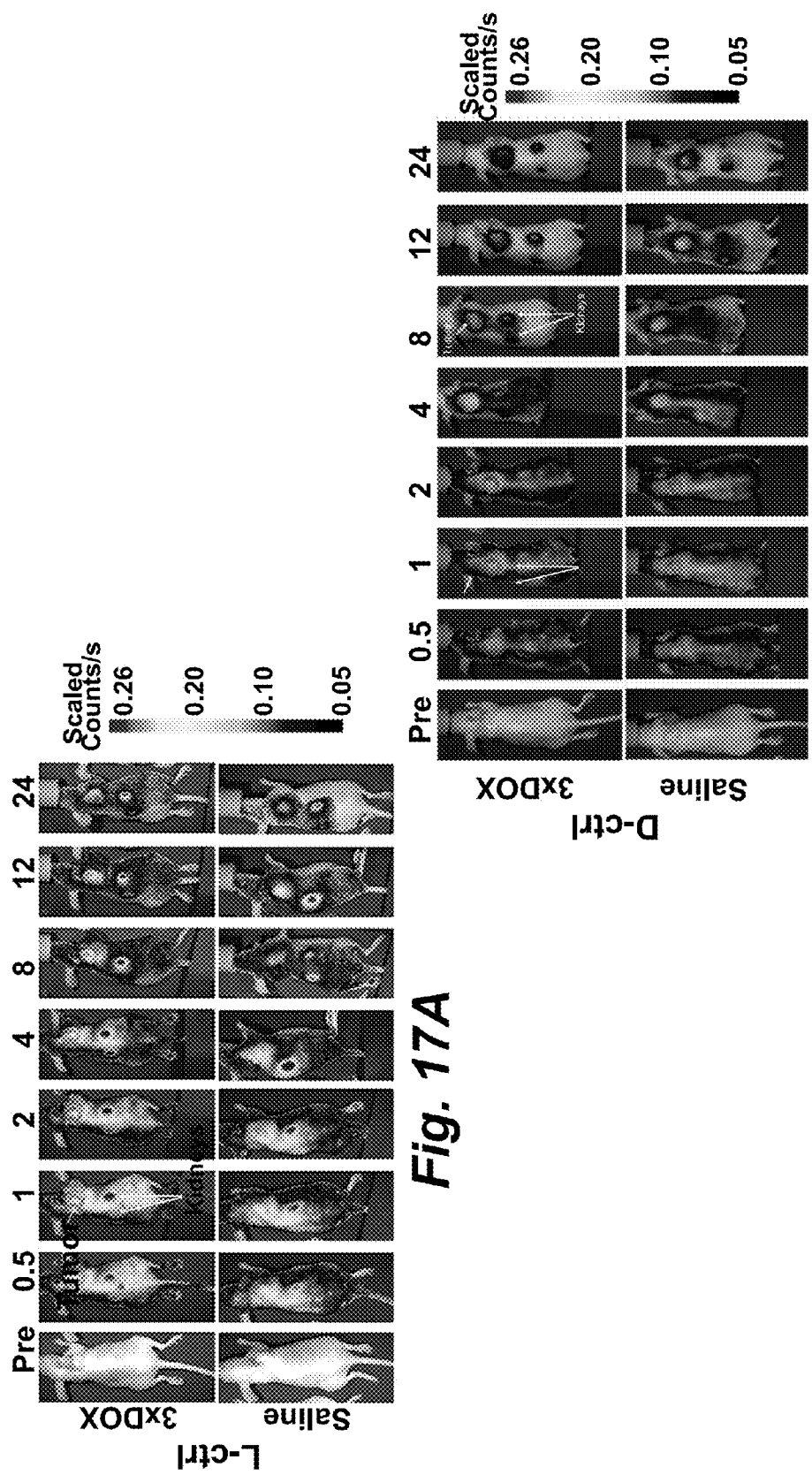

FIGS. 17A and 17B show a comparison of tumor fluorescence in saline- and DOX-treated mice with L-ctrl and D-ctrl. Representative longitudinal fluorescence imaging of 3×DOX- (top) and saline-treated (bottom) tumor-bearing mice following administration of 5 nmol L-ctrl (FIG. 17A) and D-ctrl (FIG. 17B), respectively. Anatomical locations of the tumor and kidneys are indicated. The results showed that only C-SNAF is able to produce higher tumor fluorescence with significant difference between DOX- and saline-treated mice.

FIGS. 18A-18D illustrate the correlation of enhanced C-SNAF macrocyclization and tissue retention with caspase-3 activation and tumor response to therapy.

Figure 18A:
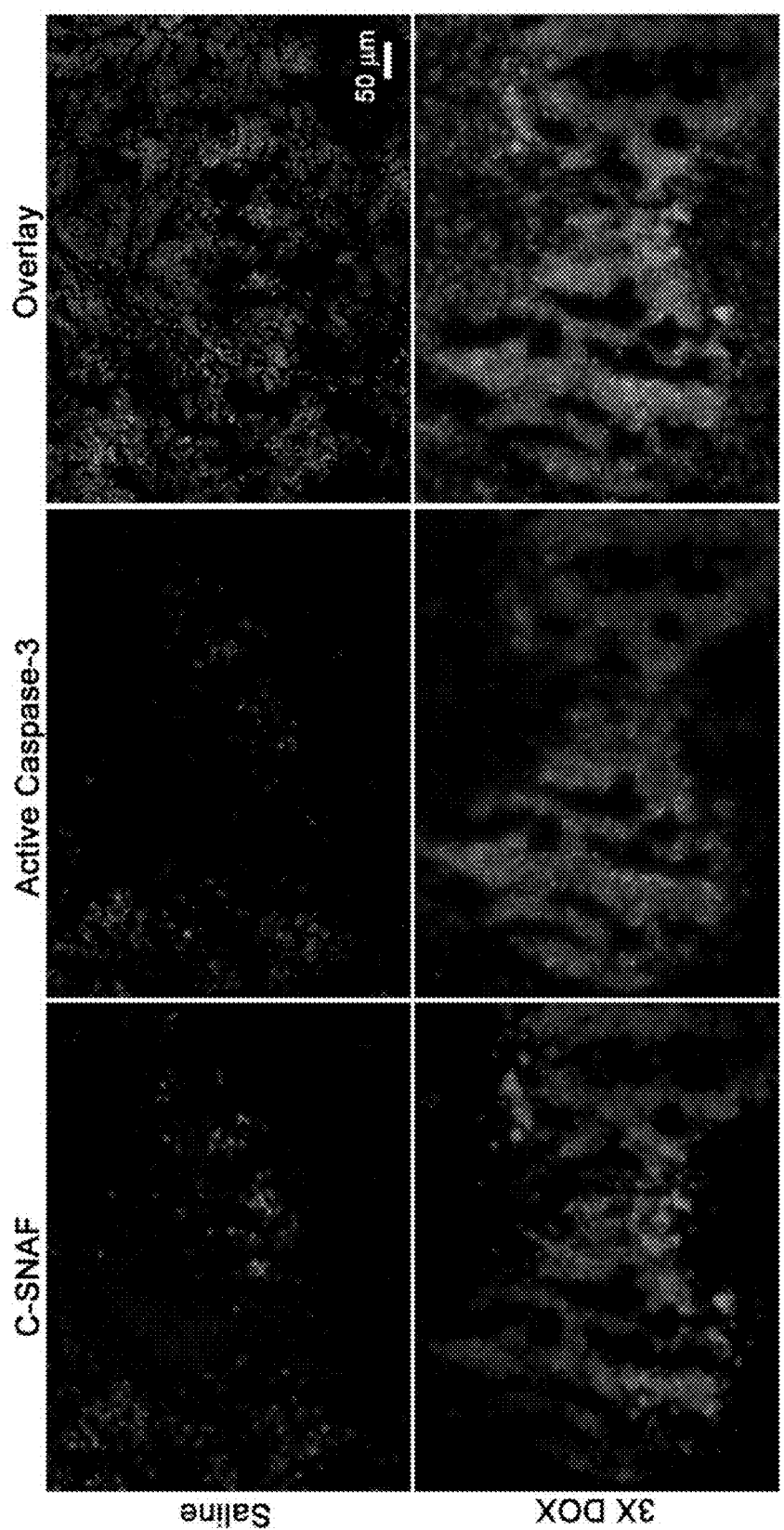

FIG. 18A is a series of digital images illustrating an immunohistochemical analysis of tumors resected from mice treated with saline (top) or 3×DOX (bottom) 4 h following administration of 5 nmol C-SNAF. Tissue sections were stained for nuclei and active caspase-3. Scale bars: 50 µm.

FIG. 18B illustrates HPLC traces of C-SNAF (5 µM) following 24 h incubation with tumor lysate from mice after treatment with saline (bottom), 3×DOX (middle), or saline with addition of recombinant human caspase-3 (top, 4.9× $10^{-3}$ U/mL). Peak # indicates C-SNAF-cycl.

FIG. 18C is a graph showing a plot of the maximum tumor fluorescence 1 h after C-SNAF administration versus the maximum tumor size change following 3×DOX chemotherapy or saline, revealing a correlation for DOX-treated mice (r=−0.9, p<0.05), but no correlation for saline-treated animals (p>0.05).

FIG. 18D illustrates the same plots of maximum tumor fluorescence as shown in FIG. 18B 1 h after control probe administration versus the maximum tumor size change following 3×DOX chemotherapy revealed no significant correlation (p>0.05) for both the L-ctrl and D-ctrl. The regression line (solid) and 95% confidence interval (dashed) are shown.

Figure 19:
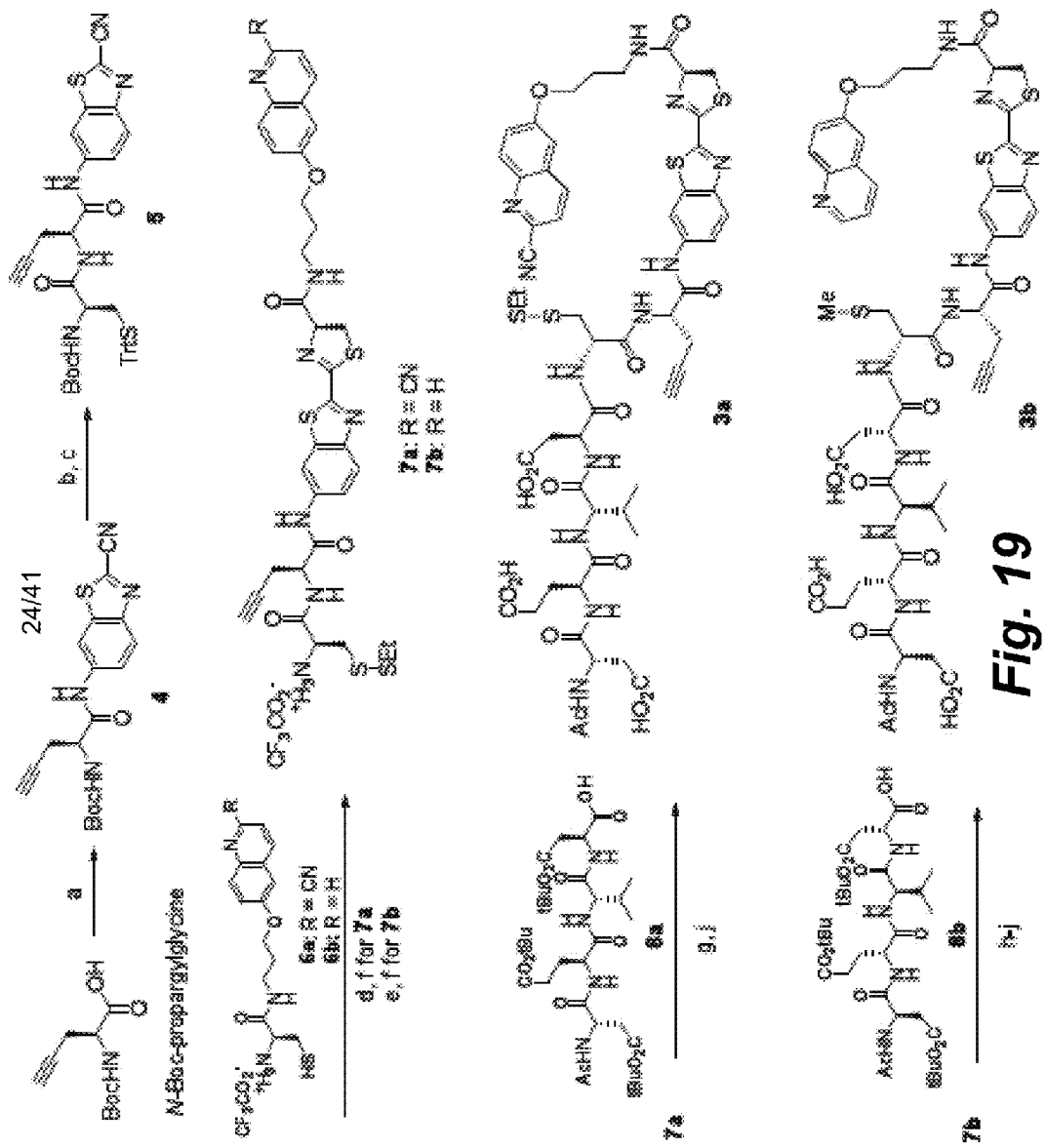

FIG. 19 illustrates a scheme for the synthetic procedure of precursors 3a and 3b: a) i-butyl chloroformate, 4-methylmorpholine, THF, 0° C., 2 h and then 6-amino-2-cyanobenzothiazole, THF, 0° C. to RT, 12 h; 85%; b) 60% TFA in DCM, room temperature, 1 h; c) N-Boc-S-Trt-D-Cysteine, HBTU, DIPEA, DMF, room temperature, 2 h; 80% from 4; d) 6a, DIPEA, DMF, room temperature, 30 min; e) 6b, DIPEA, DMF, 30 min; f) 60% TFA in DCM, room temperature, 1 h and then 2-(ethyldisulfanyl) pyridine, MeOH, room temperature, 2 h; 51% from 5 for (7a), 40% for 7b; g) Ac-DEVD-OH (8a), HBTU, DIPEA, THF, room temperature, 1 h; h) Ac-devd-OH (8b), HBTU, DIPEA, THF, RT, 1 h; i) CH$_3$I, TCEP.HCl, DIPEA, DMF, 1 h; and j) 50% TFA in DCM, room temperature, 2 h; 69% (3a) from 7a, 38% (3b) from 7b.

FIG. 20 illustrates a scheme for the radiosynthesis of 1 and 1-D: a) $^{18}$F/K$_{222}$/K$_2$CO$_3$, DMSO, 110° C., 20 min; b) 3a, Cu(CH$_3$CN)$_4$PF$_6$, BPDS, DMSO/water, 60° C., 30 min; c) 3b, CuSO$_4$, sodium ascorbate, DMSO/water, 40° C., 30 min; d) 11, 40° C., 30 min.

FIG. 21A illustrates an analytical radio-HPLC showing the radioactive signal composition: a) 1 in saline; b) 1 incubated with caspase-3 in solution for 1 h; c) extraction from 1 cellular uptake in apoptotic cell (4 h); d) extraction from 1 cellular uptake in healthy cell (4 h); e) 1-D in saline; and f) 1-D incubated with caspase-3 for 1 h. The cyclized product 2 was clearly observed in apoptotic cells, but not in healthy cells.

FIG. 21B is a graph illustrating in vitro uptake (fold over healthy cell±sem, n=3) of 1 in healthy HeLa cells, apoptotic HeLa cells (treated with 2 µM doxorubicin) and apoptotic HeLa cells with the caspase-3 inhibitor (50 µM of Z-VAD-FMK) added. There was a significant uptake increase in apoptotic cells compared with healthy cells (P=0.045).

Figure 22:
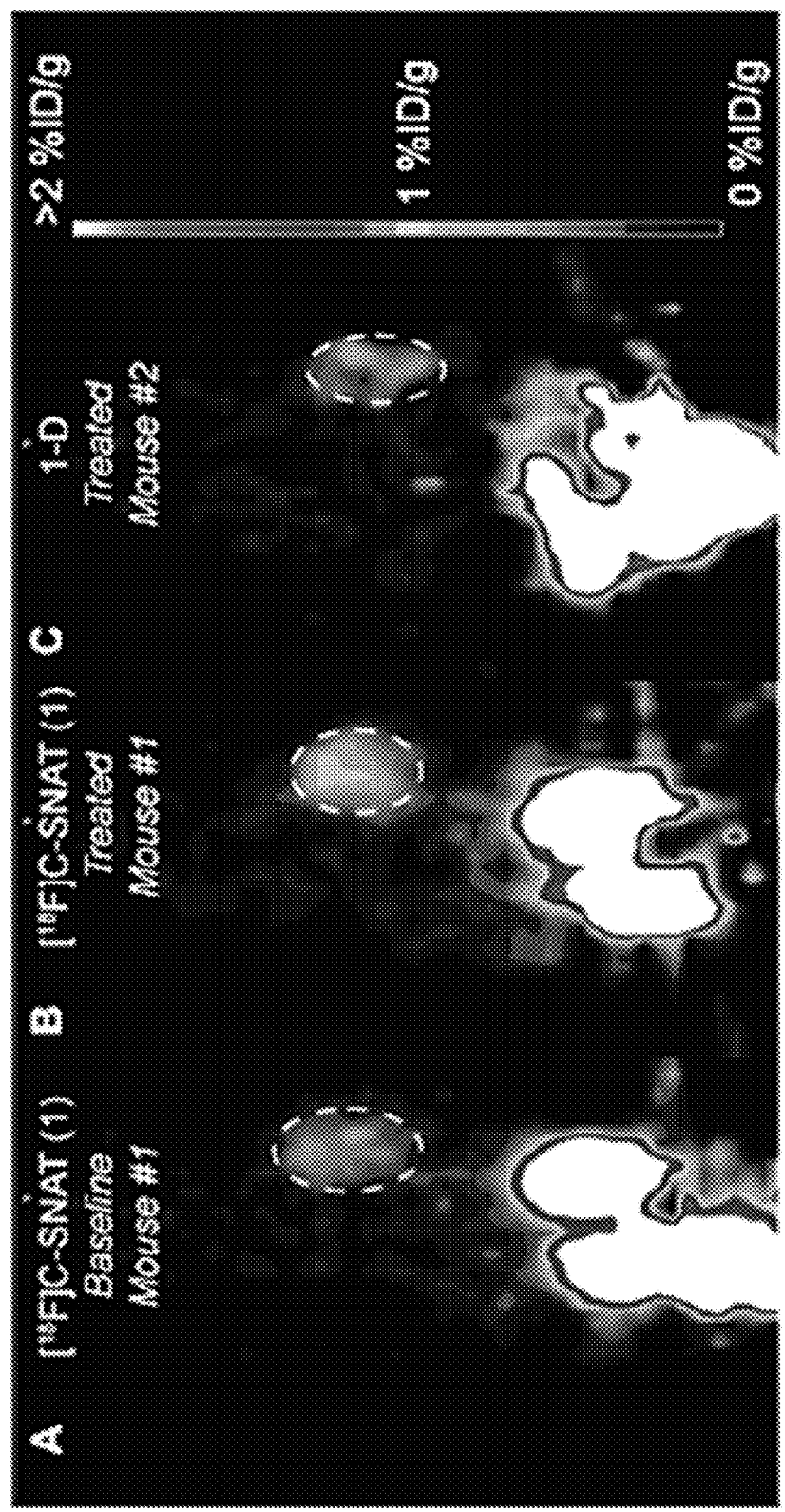

FIG. 22 shows representative PET images showing HeLa tumor xenografts (white dashed circles) on the right shoulder of mice 125 min after intravenous injection of tracer before (Panel A), and after (Panels B & C), doxorubicin treatment. Panel A: Mouse #1 before treatment imaged with 1 (7.8 MBq/211 µCi). Panel B: Mouse #1 after treatment imaged with 1 (12 MBq/324 µCi). Panel C: Mouse #2 after treatment imaged with 1-D (5.4 MBq/146 µCi). The images have been normalized to the same scale.

FIG. 23A is a graph illustrating the uptake of activatable tracer 1 and control tracer 1-D (% ID/g±sem) in xenograft HeLa tumor and muscle before and after treatment with intratumor injection of 0.2 mg of DOX 4 days prior to the imaging. Uptake is calculated based on 5 min static PET scans at 65, 125 and 182 min. The muscle region is on the left shoulder and corresponding to a muscle/bone mixture. The uptake of [$^{18}$F]C-SNAT in treated tumor is significantly higher than in untreated tumor (p=0.002) after 182 min.

FIG. 23B is a graph illustrating the effect of treatment on the uptake in tumor. [$^{18}$F]C-SNAT shows a significantly larger effect at 182 min compared with 1-D (p=0.0037).

FIG. 23C is a graph illustrating the ratio between tumor and muscle uptake in treated tumors, calculated based on the uptake (average uptake in tumor/average uptake in muscle region).

FIG. 24A illustrates an analytical HPLC (method E) chromatograph (UV at 254 nm) for monitoring click chemistry in 1-D synthesis.

FIG. 24B illustrates an analytical HPLC (method E) chromatograph (UV at 254 nm) for monitoring click chemistry in 1-D synthesis. Aliquot of reaction mixture 30 min after adding 11.

Figure 25:
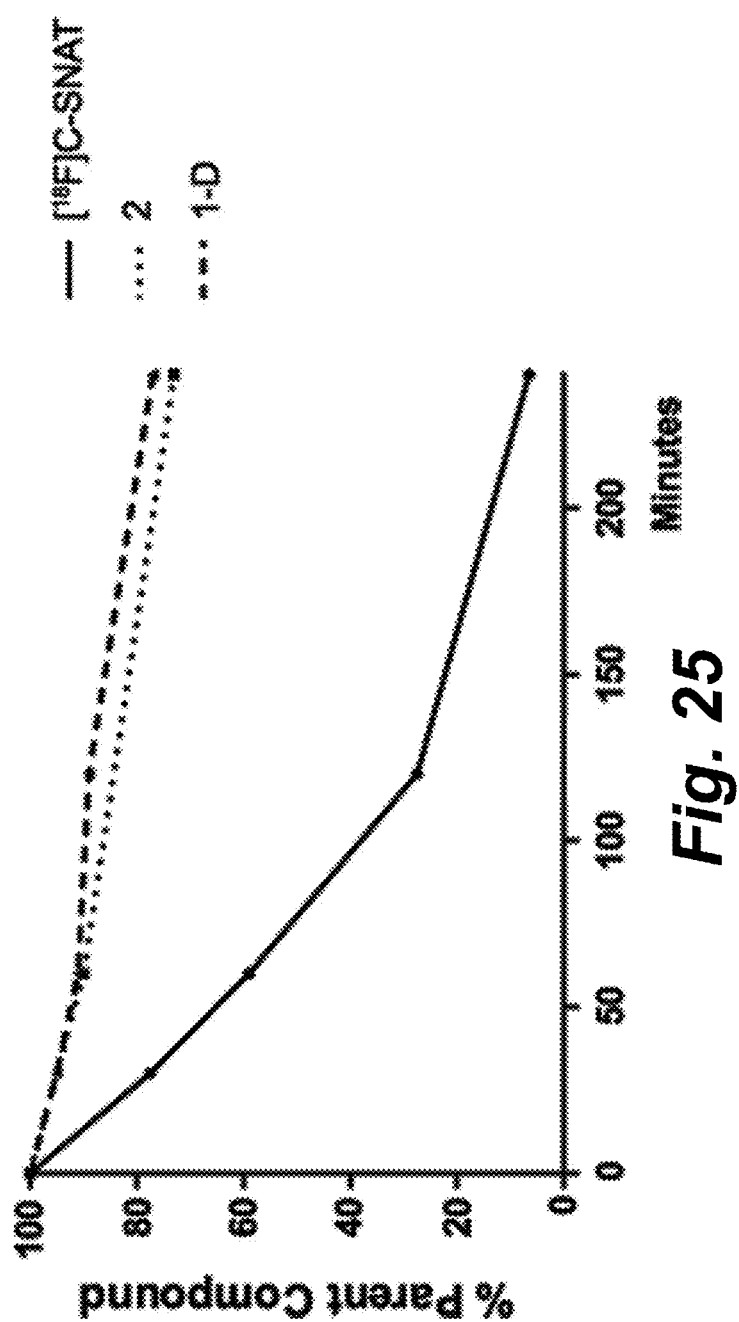

FIG. 25 is a graph illustrating the stability of [$^{18}$F]C-SNAT, 1-D and 2 in mouse serum.

FIG. 26A is a graph illustrating caspase-3 level in cell culture. Levels in treated cells are significantly higher than control (p=0.0014).

FIG. 26B is a graph illustrating caspase-3 level in tumor. Levels in treated tumor are significantly higher than control (p=0.0149).

FIG. 27A illustrates HPLC traces of probe 15 and the incubation solution of probe 15 (200 µM) with recombinant human caspase-3 (50 nM) in caspase buffer at 37° C. for 5 h.

FIG. 27B is a graph showing an enzymatic kinetics study of probe 15 (200 µM) using HPLC assay by longitudinal monitoring of % conversion of probe 15 to 2 after incubation with caspase-3 (50 nM).

FIG. 27C illustrates TEM images of GdNPs from the incubation solution of 1 (200 µM) with caspase-3 (50 nM) in caspase buffer.

FIGS. 27D and 27E, respectively, illustrate the T$_1$ values of the incubation solution of 1 (208 µM) with different proteases (50 nM) (FIG. 27D) or different concentration of casapase-3 (FIG. 27E) at 1 T.

FIG. 28A illustrates fluorescence images of viable (STS (−)) and apoptotic (STS (+)) HeLa cells with probe 1-FITC (22). Cells were stained with nuclear binding probe Hoechst 33342.

FIG. 28B illustrates ICP-MS results showing the uptake of gadolinium (Gd) in HeLa cells after incubation with different Gd-based MRI probes (250 µM) for 24 h.

FIGS. 28C and 28D illustrate $T_1$ values (1 T) (FIG. 28C) and $T_1$-weighted images (3 T) (FIG. 28D) of viable or apoptotic HeLa cell pellets after incubation with 1 or Dotarem (250 µM) for 24 h.

FIGS. 29A and 29B are representative $T_1$-weighted MR images of doxorubicin pre-treated (baseline) and post-treated (treated) HeLa tumors before (pre-contrast), 40 and 120 min after intravenous injection of 0.1 mmol $Kg^{-1}$ probe 15 (FIG. 29A) or 1-ctrl (FIG. 29B).

FIG. 29C is a graph illustrating the average SI enhancement in baseline and treated tumors 40 and 120 min after the administration of 1 (n=8) or 1-ctrl (n=4). *p<0.05.

FIG. 29D is a graph illustrating the % difference of SI enhancement between baseline and treated tumor after injection of probe 15 or 1-ctrl (19) at indicated time point.

Figure 30A:
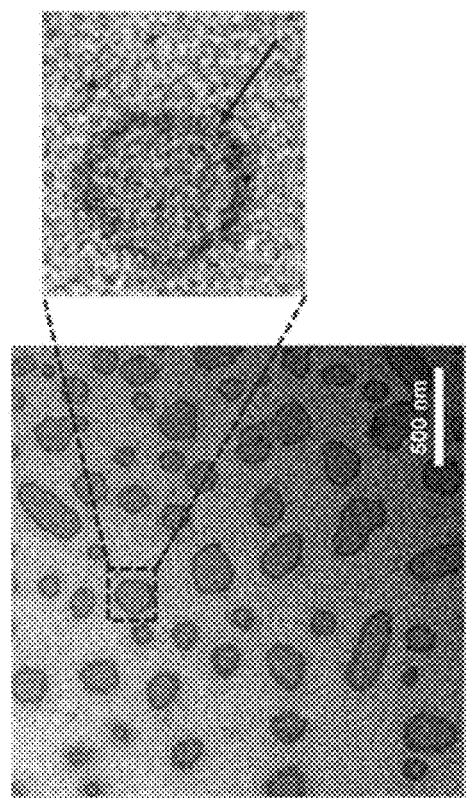
Figure 30B:
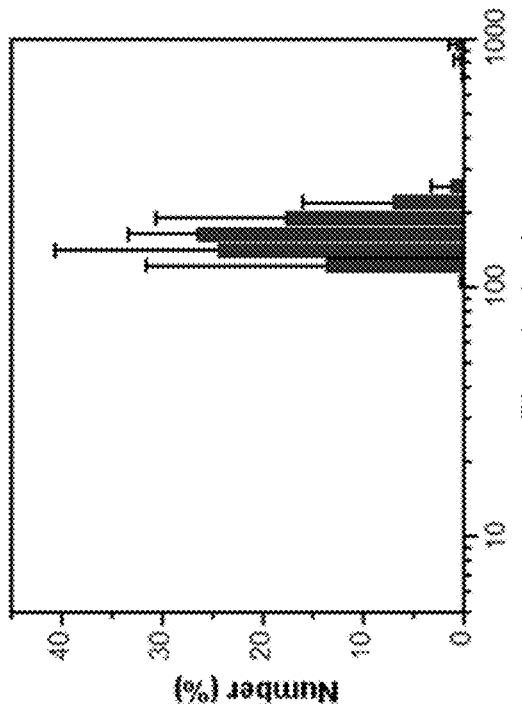

FIGS. 30A and 30B illustrate the nano-characterization of cyclized products of MRI probe 15 in vitro.

FIG. 30A illustrates dynamic light scattering (DLS) analysis of solution of probe 15 (200 µM) after incubation with caspase-3 (50 nM) in enzyme reaction buffer (pH 7.4) overnight. Error bars indicated standard deviation, coming from three repeated measurements.

FIG. 30B illustrates a transmission electron microscope (TEM) image of GdNPs from the solution as indicated in FIG. 30A. Enlarged image shows an individual GdNPs, which had a darker contrast at the edge, indicating a higher density of Gd ions at the surface (arrow indicates the surface of the nanoparticles).

Figure 31:
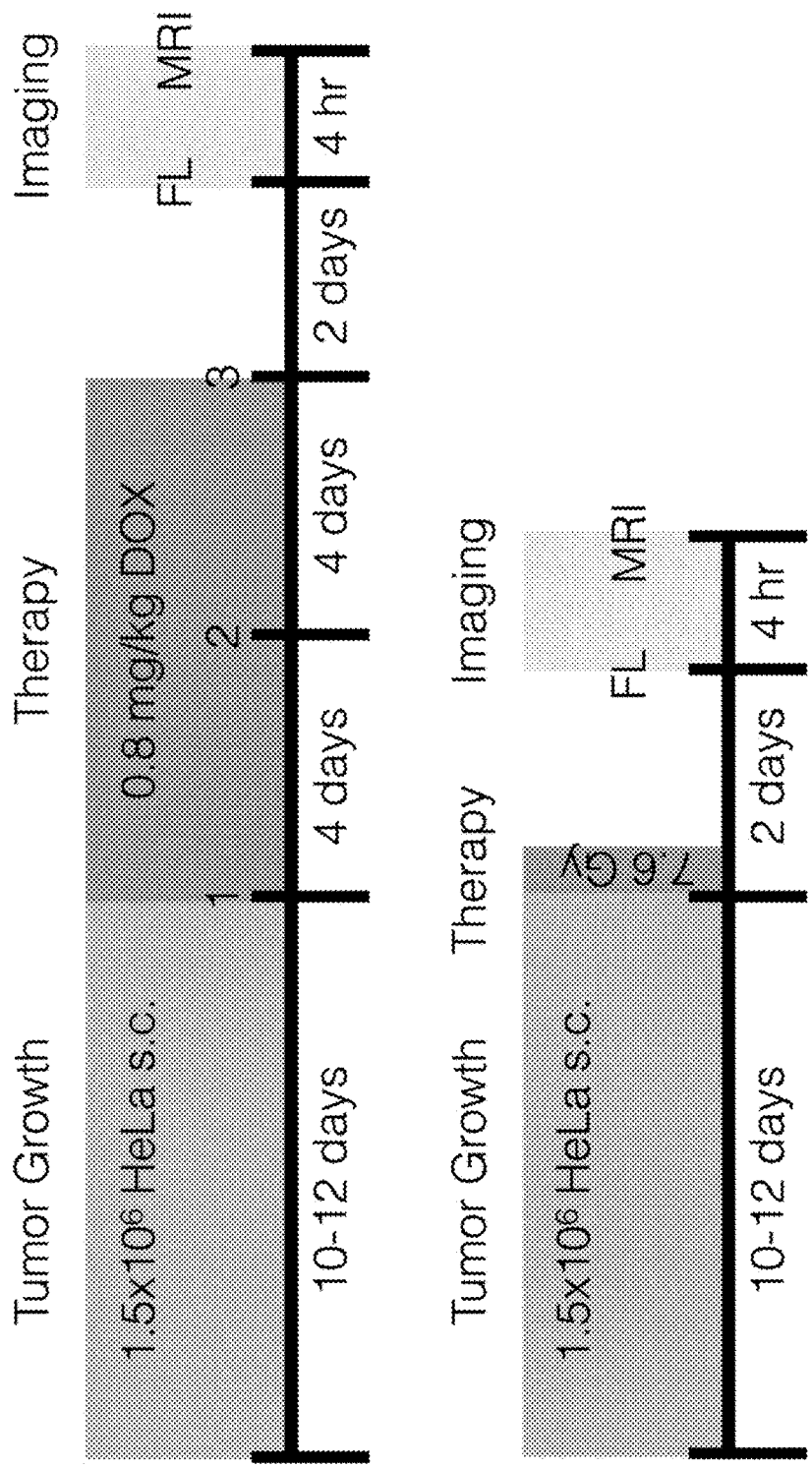

FIG. 31 illustrates treatment and imaging schemes for chemotherapy (top) and radiation therapy (bottom) of HeLa tumor-bearing mouse models. FL: fluorescence imaging; MRI: magnetic resonance imaging; s.c.: subcutaneous; DOX: doxorubicin.

Figure 32A:
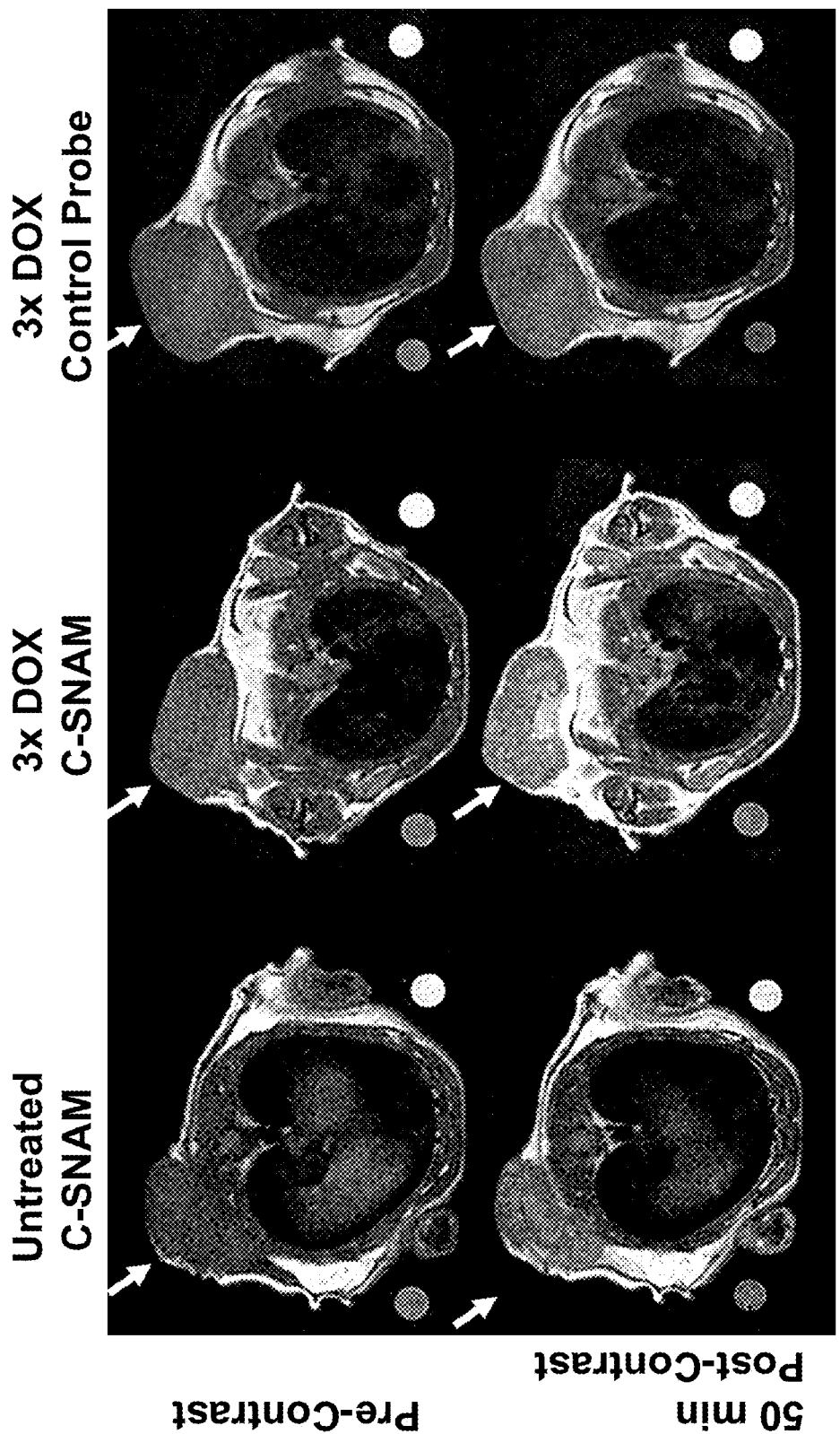
Figures 32B, 32C:
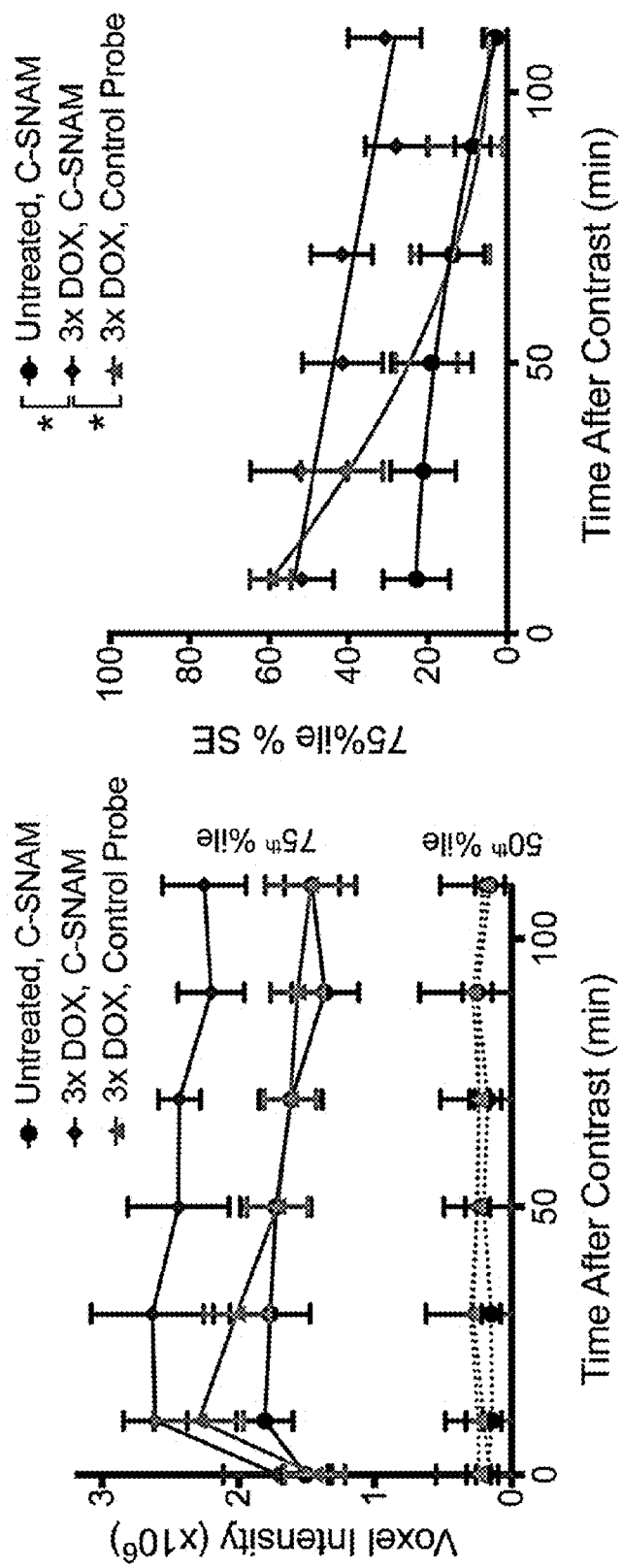

FIGS. 32A-32C illustrate in vivo imaging of tumor responses to chemotherapy.

FIG. 32A is a series of representative digital axial MR images of mice showings a tumor (indicated by arrow) 48 h after the final dose of chemotherapy, both before (top row) and 50 min after (bottom row) intravenous administration of the indicated contrast agent (0.1 mmol/kg, n=4 mice per group). Standard samples are shown on the bottom of each image with 100 µM (left) and 500 µM (right) DOTAREM® solutions.

FIG. 32B is a graph showing the quantitation of the entire tumor volume region of interest over 120 min of imaging. Voxel values for the $50^{th}$ (dashed lines) and $75^{th}$ (solid lines) intensity percentiles are shown. *p<0.05 by general linear model repeated measures analysis.

FIG. 32C is a graph showing the quantitation of the entire tumor volume region of interest over 120 min of imaging. The percent signal enhancement (SE) for the $75^{th}$ percentile is shown. *p<0.05 by general linear model repeated measures analysis.

Figure 33A:
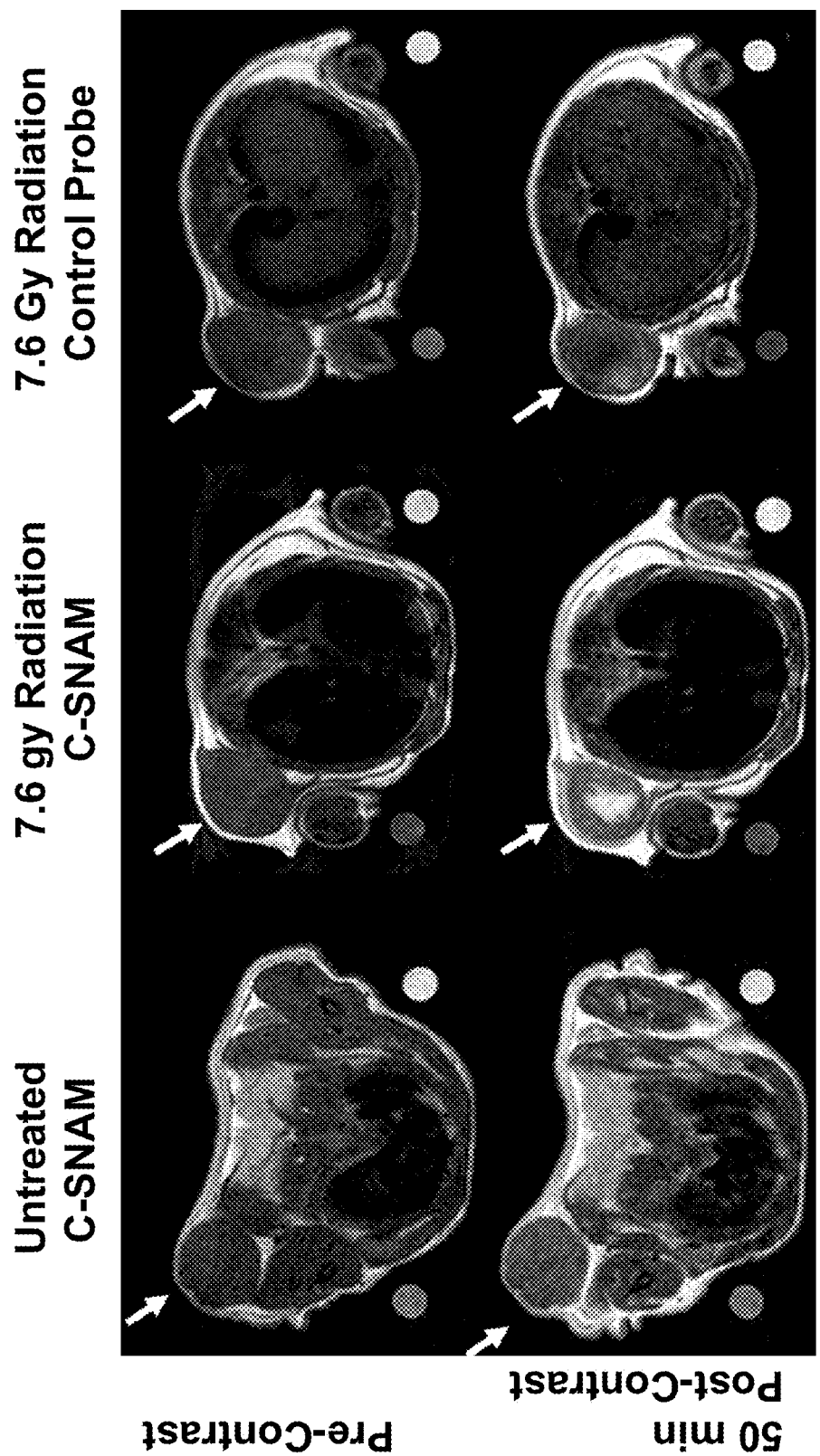
Figure 33C:
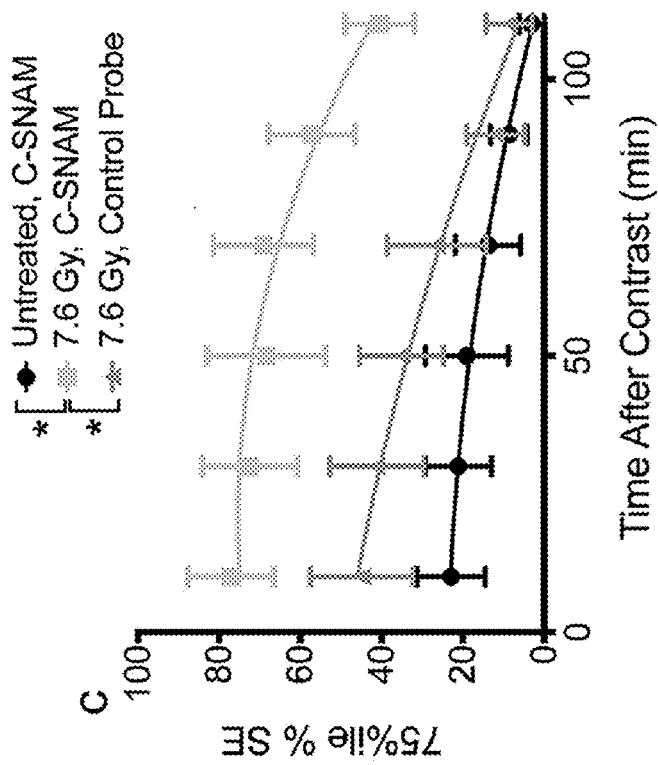
Figure 33B:
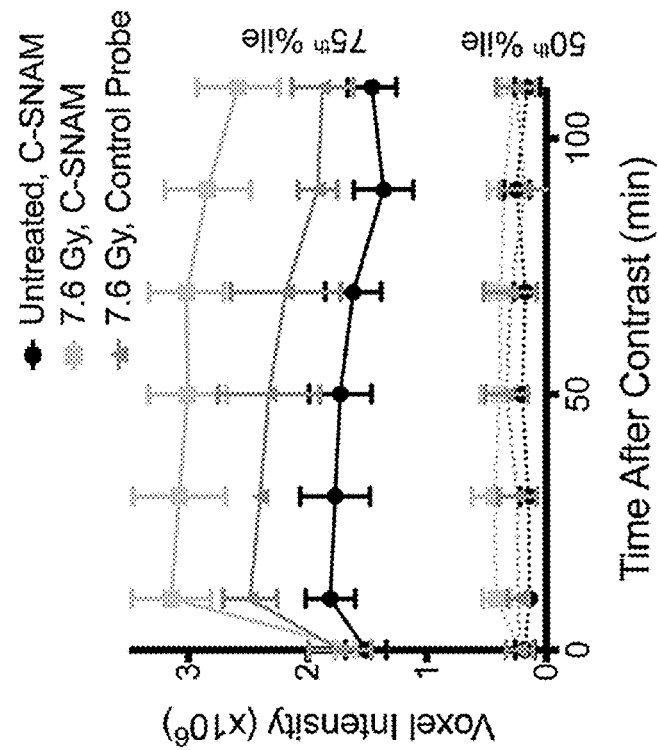

FIGS. 33A-33C illustrate in vivo imaging of a tumor response to a single dose radiation therapy (7.6 Gy).

FIG. 33A is a series of representative digital axial MR images of mice showing a tumor (indicated by arrow) 48 h after tumor irradiation, both before (top row) and 50 min after (bottom row) intravenous administration of the indicated contrast agent (0.1 mmol/kg, n=4 mice per group). Standard samples are shown on the bottom of each image with 100 µM (left) and 500 µM (right) DOTAREM® solutions.

FIG. 33B is a graph showing the quantitation of the entire tumor volume region of interest over 120 min of imaging. Voxel values for the $50^{th}$ (dashed lines) and $75^{th}$ (solid lines) intensity percentiles are shown. *p<0.05 by general linear model repeated measures analysis.

FIG. 33C is a graph showing the quantitation of the entire tumor volume region of interest over 120 min of imaging. The percent signal enhancement (SE) for the $75^{th}$ percentile is shown. *p<0.05 by general linear model repeated measures analysis.

FIGS. 34A and 34B illustrate the utility of C-SNAM for tumor therapy response monitoring by MRI molecular imaging.

FIG. 34A is a graph illustrating that contrast enhancement, measured as the value of the percent signal enhancement of the $75^{th}$ percentile intensity values 50 min post-contrast administration, correlates inversely to the fold-change in tumor volume 4 days after tumor irradiation (r=−0.95, p<0.05, n=9 mice).

FIG. 34B is a graph illustrating apoptosis monitored by C-SNAM MRI for 1, 2, and 3 days following tumor irradiation. Boxes: range; line: mean; error bars: s.d. of n=4 mice per group. *p<0.05 by one-way ANOVA.

Figure 35B:
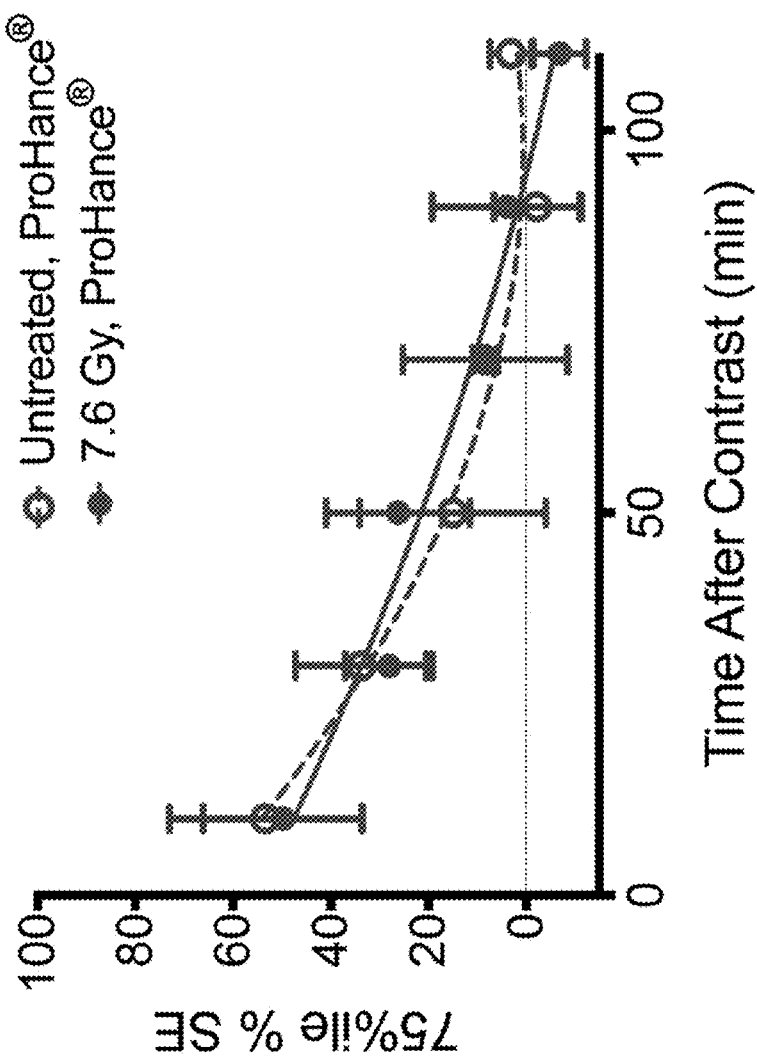
Figure 35A:
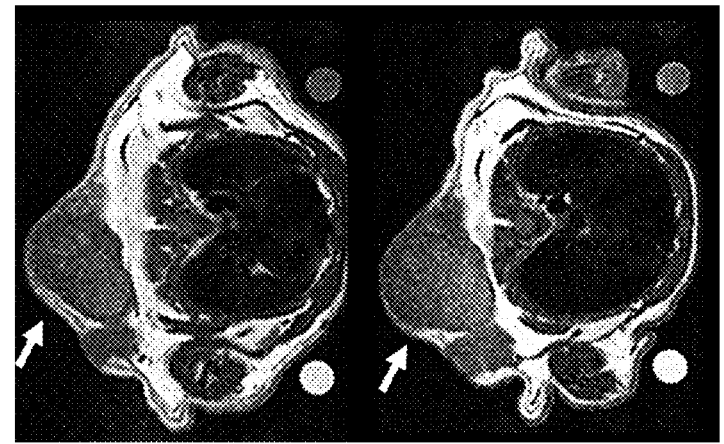

FIGS. 35A and 35B illustrate in vivo tumor radiation response monitoring with a clinical non-activatable contrast agent (PROHANCE®).

FIG. 35A shows representative digital axial MR images of the same animal showing a tumor (indicated by arrow) before (top) and 48 h after irradiation (bottom). Both images were 50 min after intravenous administration of PROHANCE® (0.2 mmol/kg, n=4 mice). Standard samples are shown on the bottom of each image with 500 µM (left) and 100 µM (right) DOTAREM® solutions.

FIG. 35B is a graph showing the quantitation of an entire tumor volume region of interest over 120 min of imaging. The percent signal enhancement (SE) for the $75^{th}$ percentile is shown for mice before (dashed line) and after (solid line) tumor irradiation.

The drawings are described in greater detail in the description and examples below.

The details of some exemplary embodiments of the methods and systems of the present disclosure are set forth in the description below. Other features, objects, and advantages of the disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, toxicology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein.

Prior to describing the various embodiments, the following definitions are provided and should be used unless otherwise indicated.

ABBREVIATIONS

C-SNAF: caspase-sensitive nano-aggregation fluorescent probe; C-SNAT: caspase-sensitive nano-aggregation tracer probe

DEFINITIONS

The term "positron emission tomography" as used herein refers to a nuclear medicine imaging technique that produces a three-dimensional image or map of functional processes in the body. The system detects pairs of gamma rays emitted indirectly by a positron-emitting radioisotope, which is introduced into the body on a metabolically active molecule. Images of metabolic activity in space are then reconstructed by computer analysis. Using statistics collected from tens-of-thousands of coincidence events, a set of simultaneous equations for the total activity of each parcel of tissue can be solved by a number of techniques, and a map of radioactivities as a function of location for parcels or bits of tissue may be constructed and plotted. The resulting map shows the tissues in which the molecular probe has become concentrated. Radioisotopes used in PET scanning are typically isotopes with short half-lives such as carbon-11 (about 20 min), nitrogen-13 (about 10 min), oxygen-15 (about 2 min), and fluorine-18 (about 110 min). PET technology can be used to trace the biologic pathway of any compound in living humans (and many other species as well), provided it can be radiolabeled with a PET isotope. The half-life of fluorine-18 is long enough such that fluorine-18 labeled radiotracers can be manufactured commercially at an offsite location.

The term "Magnetic Resonance Imaging" or (MRI) as used herein is a method to obtain an image representing the chemical and physical microscopic properties of materials, by utilizing a quantum mechanical phenomenon, named Nuclear Magnetic Resonance (NMR), in which a system of spins, placed in a magnetic field resonantly absorb energy, when applied with a certain frequency.

The term "activatable probe" as used herein refers to a probe monomer of the disclosure that includes a blocking, or capping, peptide that can be cleaved from the probe. Upon cleavage, the probe may then cyclize and aggregate to generate a non-aggregation probe structure. The term "activatable probe" may further refer to a probe of the disclosure that includes a detectable imaging moiety that is a fluorescence emitter and a detachable quencher moiety that may be, for example, attached to the capping moiety. Upon cleavage of the capping moiety from the probe, and hence activation of said probe, the quencher is displaced from the vicinity of the fluorophore imaging moiety and a detectable signal may be generated.

The term "detachable capping moiety" as used herein refers to a structure such as a peptide that when attached to the probe prevents self-cyclization of the probe and subsequent aggregation to form nano-aggregation probes.

The term "chelator" as used herein refers to a molecular moiety that may form ionic bonds to an anion and in particular to metallic ions that have at least two positive charges thereon. Chelating agents containing paramagnetic metals for use in magnetic resonance imaging can also be employed as ancillary agents. Typically, a chelating agent containing a paramagnetic metal is associated with a coating on the nanoparticles. The chelating agent can be coupled directly to one or more of components of the coating layer, such as a polyaspartate coat. Suitable chelating agents include a variety of multi-dentate compounds including EDTA, DPTA, DOTA, and the like. These chelating agents can be coupled directly to functional amino groups of a polyaspartate coat of the nanoparticles.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probe and pharmaceutically acceptable carriers can be sterile. Water is a useful carrier when the probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The term "nanoparticle" as used herein refers to a particle having a diameter of between about 1 and about 1000 nm. Similarly, by the term "nanoparticles" is meant a plurality of particles having an average diameter of between about 1 and about 1000 nm.

It will be understood by one of ordinary skill in the art that when referring to a population of nanoparticles as being of a particular "size", what is meant is that the population is made up of a distribution of sizes around the stated "size". Unless otherwise stated, the "size" used to describe a particular population of nanoparticles will be the mode of the size distribution (i.e., the peak size). By reference to the "size" of a nanoparticle is meant the length of the largest straight dimension of the nanoparticle. For example, the size of a perfectly spherical nanoparticle is its diameter.

The term "detectable signal emitter", for the purposes of the specification or claims, means a label molecule that is incorporated indirectly or directly into a nanoparticle, wherein the label molecule facilitates the detection of the nanoparticle in which it is incorporated. Thus, "detectable signal emitter" is used synonymously with "label molecule".

The term "detectable" refers to the ability to detect a signal over the background signal. The detectable signal is defined as an amount sufficient to yield an acceptable image using equipment that is available for pre-clinical use. A detectable signal maybe generated by one or more administrations of the probes of the present disclosure. The amount administered can vary according to factors such as the degree of susceptibility of the individual, the age, sex, and weight of the individual, idiosyncratic responses of the individual, the dosimetry, and the like. The amount administered can also vary according to instrument and digital processing related factors.

The term "in vivo imaging" as used herein refers to methods or processes in which the structural, functional, or physiological state of a living being is examinable without the need for a life-ending sacrifice.

The term "non-invasive in vivo imaging" as used herein refers to methods or processes in which the structural, functional, or physiological state of a being is examinable by remote physical probing without the need for breaching the physical integrity of the outer (skin) or inner (accessible orifices) surfaces of the body.

The term "optical energy" as used herein refers to electromagnetic radiation between the wavelengths of about 350 nm to about 800 nm and which can be absorbed by the dyes or cellulose-based nanoparticles of the embodiments of the photoacoustic probes of the disclosure. The term "optical energy" may be construed to include laser light energy or non-laser energy.

The term "detectable imaging moiety" or "label" as used herein refers to an atom, or radioactive atom detectable by such methods as γ-radiation detection, positron emission transmission, and the like, or to an inorganic or organic molecule that may be detected by an optical method, for example by fluorescence detection, light absorbance and the like. It should be noted that reference to detecting a signal from a probe also includes detecting a signal from a plurality of probes. In some embodiments, a signal may only be detected that is produced by a plurality of probes. Additional details regarding detecting signals (e.g., acoustic signals) are described below.

The "imaging moiety" may be detected either externally to a subject human or non-human animal body or via use of detectors designed for use in vivo, such as intravascular radiation or optical detectors such as endoscopes, or radiation detectors designed for intra-operative use. The imaging moiety is preferably chosen from, but is not limited to a positron-emitting radioactive non-metal or a reporter suitable for in vivo optical imaging. It is contemplated, however, that other detectable labels may be incorporated into the probes of the disclosure including, but not limited to a radioactive nuclide. When the imaging moiety is a radioactive metal ion, i.e. a radiometal, suitable radiometals can be either positron emitters such as $^{64}$Cu, $^{48}$V, $^{52}$Fe, $^{55}$Co, $^{94}$mTc or $^{68}$Ga or γ-emitters such as 99mTc, $^{111}$In, $^{113}$In, $^{67}$Ga. When the imaging moiety is a positron-emitting radioactive non-metal, suitable such positron emitters can include: $^{11}$C, $^{13}$N, $^{15}$O, $^{17}$F, $^{75}$Br, $^{76}$Br, or $^{124}$I.

The term "imaging moiety" as used herein may further refer to a reporter suitable for in vivo optical imaging and the reporter is any moiety capable of detection either directly or indirectly in an optical imaging procedure. The reporter can be a light scatterer (e.g. a colored or uncolored particle), a light absorber or a light emitter. More preferably the reporter is a dye such as a chromophore or a fluorescent compound. The dye can be any dye that interacts with light in the electromagnetic spectrum with wavelengths from the ultraviolet light to the near infrared. Most advantageously, the reporter has fluorescent properties.

Organic chromophoric and fluorophoric reporters suitable for use in the probes of the disclosure include groups having an extensive delocalized electron system, e.g. cyanines, merocyanines, indocyanines, phthalocyanines, naphthalocyanines, triphenylmethines, porphyrins, pyrilium dyes, thiapyrilium dyes, squarylium dyes, croconium dyes, azulenium dyes, indoaniline dyes, benzophenoxazinium dyes, benzothiaphenothiazinium dyes, anthraquinones, napthoquinones, indathrenes, phthaloylacridones, trisphenoquinones, azo dyes, intramolecular and intermolecular charge-transfer dyes and dye complexes, tropones, tetrazines, bis(dithiolene) complexes, bis(benzene-dithiolate) complexes, iodoaniline dyes, bis(S,O-dithiolene) complexes. Fluorescent proteins, such as green fluorescent protein (GFP) and modifications of GFP that have different absorption/emission properties are also useful.

Particular examples of chromophores which may be used include: fluorescein, sulforhodamine 101 (Texas Red), rhodamine B, rhodamine 6G, rhodamine 19, indocyanine green, Cy2, Cy3, Cy3B, Cy3.5, Cy5, Cy5.5, Cy7, Cy7.5, Marina Blue, Pacific Blue, Oregon Green 88, Oregon Green 514, tetramethylrhodamine, and Alexa Fluor 350, Alexa Fluor 430, Alexa Fluor 532, Alexa Fluor 546, Alexa Fluor 555, Alexa Fluor 568, Alexa Fluor 594, Alexa Fluor 633, Alexa Fluor 647, Alexa Fluor 660, Alexa Fluor 680, Alexa Fluor 700, and Alexa Fluor 750.

Particularly advantageous are dyes which have absorption maxima in the visible or near infrared (NIR) region, between 400 nm and 3 µm, particularly between 600 and 1300 nm. Optical imaging modalities and measurement techniques include, but are not limited to: luminescence imaging; endoscopy; fluorescence endoscopy; optical coherence tomography; transmittance imaging; time resolved transmittance imaging; confocal imaging; nonlinear microscopy; photoacoustic imaging; acousto-optical imaging; spectroscopy; reflectance spectroscopy; interferometry; coherence interferometry; diffuse optical tomography and fluorescence mediated diffuse optical tomography (continuous wave, time domain and frequency domain systems), and measurement of light scattering, absorption, polarization, luminescence, fluorescence lifetime, quantum yield, and quenching.

The term "fluorophore" as used herein refers to a component of a molecule that causes a molecule to be fluorescent. It is a functional group in a molecule which will absorb energy of a specific wavelength and re-emit energy at a different (but equally specific) wavelength. The amount and wavelength of the emitted energy depend on both the fluorophore and the chemical environment of the fluorophore. Fluorophores for use in the compositions of the disclosure include, but are not limited to, fluorescein isothiocyanate (FITC), a reactive derivative of fluorescein, which has been one of the most common fluorophores chemically attached to other, non-fluorescent, molecules to create new fluorescent molecules for a variety of applications.

Other historically common fluorophores are derivatives of rhodamine (TRITC), coumarin, and cyanine. Newer generations of fluorophores such as the ALEXA FLUORS® and the DYLIGHT FLUORS® are generally more photostable, brighter, and less pH-sensitive than other standard dyes of comparable excitation and emission.

The term "fluorescent acceptor molecule" as used herein refers to any molecule that can accept energy emitted as a result of the activity of a bioluminescent donor protein, and re-emit it as light energy.

The terms "fluorescence quencher", "quencher", or "quenching moiety" as used herein refer to a molecule that interferes with the fluorescence emitted by a fluorophore or bioluminescent polypeptide. This quencher can be selected from non-fluorescent aromatic molecules, to avoid parasitic emissions. Exemplary quenchers include, but are not limited to, Dabsyl or a BLACK HOLE QUENCHER® that are non-fluorescent aromatic molecules that prevent the emission of fluorescence when they are physically near a fluorophore. The quencher can also be, but is not limited to, a fluorescent molecule, for example TAMRA (carboxytetramethylrhodamine). A particularly advantageous quencher suitable for use in the compositions of the disclosure is a modified dye such as IR-775-COOH. When the quencher is a fluorescent dye, its fluorescence wavelength is typically substantially different from that of the reporter dye.

The terms "quench" or "quenches" or "quenching" or "quenched" as used herein refer to reducing the signal produced by a molecule. It includes, but is not limited to, reducing the signal produced to zero or to below a detectable limit. Hence, a given molecule can be "quenched" by, for example, another molecule and still produce a detectable signal, albeit the size of the signal produced by the quenched molecule can be smaller when the molecule is quenched than when the molecule is not quenched.

The term "contrast agent" as used herein refers to an agent that when delivered to an animal or human subject can improve the image obtained by a method such as magnetic resonance imaging (MRI). Such agents may include, but are not limited to gadolinium, iron oxide, manganese and magnesium salts, and the like that may be formulated into pharmaceutically acceptable compositions for administering in vivo with limited and acceptable degrees of undesirable side effects. One suitable MRI contrast agent for incorporation into the liposomal nanoparticle delivery vehicles of the disclosure is gadolinium (Gd), and derivatized variants thereof. A particularly useful such derivative, but not intended to be limiting, is Gadofluorine (GdF, Bayer Schering Pharma AG), a gadolinium analogue that is an amphiphilic, macrocyclic, gadolinium-containing complex. It is a derivative of Gd-DO3A containing a perfluorooctyl side chain and a mannose moiety. Other Gd derivatives for use as an MRI contrast agent are, but not limited to, Carbocyanine-labelled GdF (cc-GdF), Gd-DTPA (MAGNEVIST®, Bayer Schering Pharma, Berlin, Germany), Gd-DO3A and the like.

The term "selectively cleavable" as used herein refers to when a linker is not cleaved by certain reactions conditions, but selectively cleavable by different reaction conditions. The selectively cleavable peptide of the probes of the disclosure will include a peptide bond that can be cleaved by peptidase the activity of which is to be detected by the probe, but not cleaved by other peptidases. For example, but not intended to be limiting, the targeted peptidase can be a caspases 3 or 7 (hereinafter caspases 3/7) that is induced by the onset of apoptosis in a cell and cleaves a peptide bond at the C-terminus of the peptide L-aspartate-glutamate-valine-aspartate, whereas same peptide bond is not cleaved by a different peptidase.

The term "caspase" as used herein refers to a family of cysteine-aspartic proteases or cysteine-dependent aspartate-directed proteases that are a family of cysteine proteases that play essential roles in apoptosis (programmed cell death), necrosis, and inflammation. Failure of apoptosis is one of the main contributions to tumor development and autoimmune diseases; this, coupled with the unwanted apoptosis that occurs with ischemia or Alzheimer's disease, has stimulated interest in caspases as potential therapeutic targets. Effector caspases (e.g., CASP3, CASP6, and CASP7) cleave protein substrates within the cell to trigger the apoptotic process. The initiation of this cascade reaction is regulated by caspase inhibitors. Caspases are first synthesized as inactive pro-caspases that consist of a prodomain, a small subunit and a large subunit. Granzyme B (released by cytotoxic T lymphocytes and NK cells) is known to activate caspase-3 and -7.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present disclosure, suitable methods and materials are described herein.

DESCRIPTION

Figure 1A:
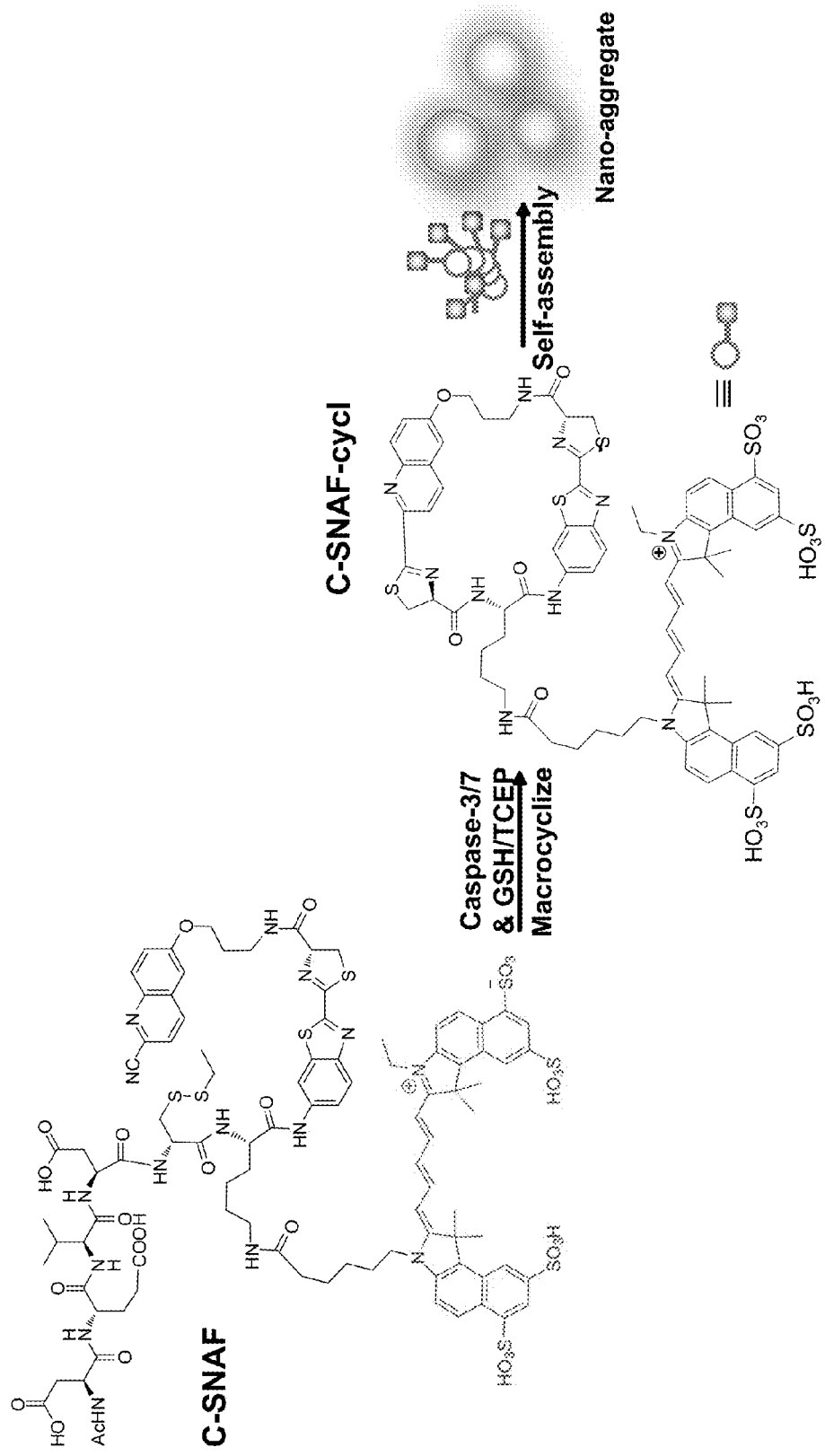
FIGS. 1A-1C illustrate the mechanism of in vivo imaging of caspase-3/7 activity in human tumor xenograft mouse models by C-SNAF.

The disclosure provides embodiments of an activatable probe, the synthesis, and biological applications thereof, that undergoes intramolecular cyclization and subsequent aggregation in apoptotic tumor cells upon peptidase initiated, and most advantageously caspase-3, activation. The caspase-sensitive nano-aggregation probes (C-SNAFs) of the disclosure are generally biocompatible, possess NIR spectral properties or may serve as PET or MRI imaging agents, and have a mechanism of target-mediated nanostructure self-assembly amenable to in vivo use. Generation of embodiments of the probes of the disclosure encompass, but are not intended to be limited to, biocompatible condensation chemistry products that may comprise D-cysteine and 2-cyano-6-hydroxyquinoline (CHQ) moieties linked to an amino-luciferin scaffold, and which can be activated by a two-step reaction requiring, most advantageously, both caspase-3/7-mediated cleavage of an aspartate-glutamate-valine-aspartate (L-DEVD) capping peptide and the free intracellular thiol-mediated reduction of the disulfide bond, as shown in FIG. 1A. The activatable probes of the disclosure can further include a detectable imaging moiety such as, but not limited to, an optically detectable label such as a fluorophore or a label detectable by an imaging method such as PET or MRI. The activatable probes of the disclosure are especially advantageous for the detection and imaging of cells and animal tissues that have a degree of apoptosis. The apoptosis may be induced as a result of being a tumorous or cancerous tissue, or therapeutically induced. Accordingly, the probes and methods of the disclosure are advantageous for the imaging of apoptotic tissues or for monitoring the effectiveness of a therapeutic regimen that can, for example, induce apoptosis in a target cell or tumor.

To generate the probes of the disclosure, an optimized CBT-like first-order condensation reaction (Ye et al., (2011) *Angew. Chem. Int. Ed.* 50: 2275-2279) was used to control self-assembly of a fluorescent small molecule. In vivo applicability is through imaging of chemotherapeutic efficacy of human tumor xenograft mouse models.

Imaging tumor apoptosis could provide invaluable predictive information regarding therapeutic efficacy and anti-cancer drug selection (Brindle, K. 2008) *Nat. Rev. Cancer* 8: 94-107; Blankenberg, F. G. (2008) *J. Nucl. Med.* 49 Suppl. 2; 81S-95S). Among the molecular events signalling cellular commitment to apoptosis, the effector caspases (e.g. caspase-3 and -7) (Nguyen et al., (2009) *Proc. Natl. Acad. Sci. U.S.A.* 106: 16375-16380; Johnson et al., (2012) *Bioconjugate Chem.* 23: 1783-1793) are the most attractive as apoptosis imaging targets. Using this model system, a series of in vitro and in vivo experiments demonstrated that a synthetic small molecule according to the disclosure can be controlled to self-assemble into nanoparticles, distinguishing negatively from positively responding tumors during the course of chemotherapy. Individual in situ assembled fluorescent nanoparticles have been imaged in apoptotic cells using three-dimensional structured illumination microscopy. This work represents the first synthetic small molecule capable of undergoing self-assembly in living mammalian organisms, proving the potential utility of in situ self-assembly for molecular imaging with this novel bioorthogonal cyclization chemistry.

Figure 1B:
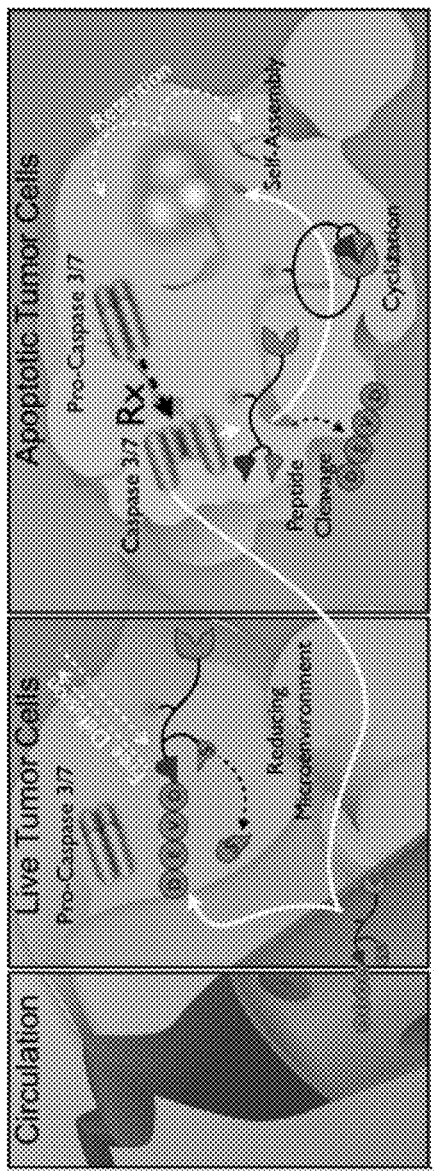

FIG. 1B illustrates mechanisms by which a C-SNAF according to the disclosure can report chemotherapy-induced tumor cell death in vivo. After intravenous administration, C-SNAF extravasates and penetrates into tumor tissue. In living tumor tissue that is unresponsive to applied therapy, the unactivated form of caspase-3 (pro-caspase-3) dominates, preventing the release of the L-DEVD capping peptide of C-SNAF (Thornberry et al., (1997) *J. Biol. Chem.* 272: 17907-17911) and allowing for rapid diffusion away from the tumor. In regions of tumor apoptosis, the increase in cell membrane permeability upon progression through apoptosis to cell death is well characterized, enhancing the ability of C-SNAF to partition into apoptotic tumor cells (Pozarowski et al., (2003) *Cytometry A* 55: 50-60; Park et al., (2011) *J. Am. Chem. Soc.* 133: 2832-2835; Pace et al., (2012) *Angew. Chem. Int. Ed.* 51: 8365-8368); Pro-caspase-3 is efficiently converted to active caspase-3 which cleaves the L-DEVD capping group from the C-SNAF and initiates intramolecular condensation to form the macrocyclic product C-SNAF-cycl.

C-SNAF-cycl, regardless of the nature of the attached labelling moiety, is more rigid and hydrophobic (log P: 3.06 for C-SNAF-cycl vs. −2.44 for C-SNAF) (Tetko et al., (2005) *J. Comput. Aided Mol. Des.* 19; 453-463), and is thus amenable to increased intermolecular interactions (i.e. hydrophobic interactions, π-π stack) relative to C-SNAF, promoting its in situ nano-aggregation. These nano-aggregates trap the activated probe in apoptotic cells and afford high imaging contrast for treatment response detection.

Figure 1C:
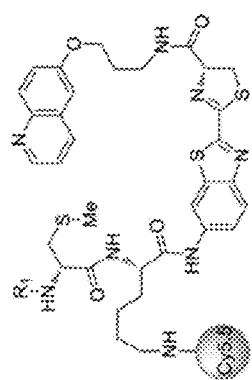

To demonstrate the caspase-3-triggered in situ self-assembly of C-SNAF in tumors, control compounds were synthesized with similar chemical structures, but with increasing degrees of inertness to activation. One control (designated Loth) comprised a methylated cysteine thiol and a quinolin-6-yl ring replacing the CHQ moiety, preventing intramolecular cyclization following L-DEVD peptide cleavage by caspase-3/7, as shown in FIG. 1C. Thus, the application of L-ctrl can interrogate the relative contribution of peptide cleavage versus triggered nano-aggregation to the mechanism of C-SNAF molecular imaging.

Figure 2A:
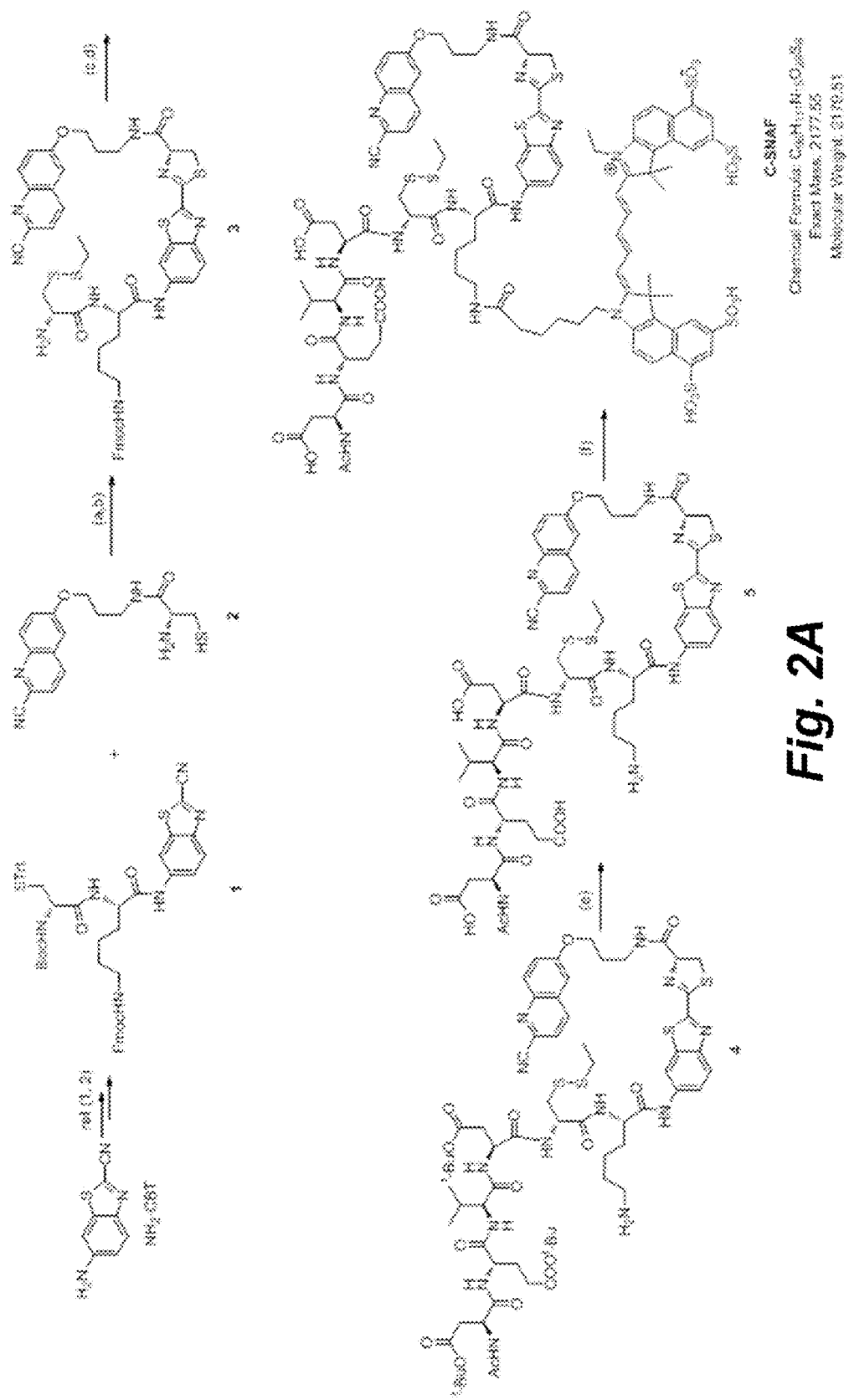
FIG. 2A illustrates a scheme for the synthesis of C-SNAF. Reaction conditions: (a) TCEP, DIPEA, DCM/MeOH, Ar, room temperature 1 h; (b) (i) 20% TFA/DCM; (ii) PySSEt, MeOH, 71%; (c) Ac-Asp(O$^t$Bu)-Glu(O$^t$Bu)-Val-Asp(O$^t$Bu)-COOH, HBTU, DIPEA, THF; (d) piperidine, DMF, 43% in two steps; (e) TFA/TIPSH/DCM (95%/2.5%/2.5%), 83%; (f) Cy 5.5-NHS, DMF, DIPEA, 53%.
Figure 2B:
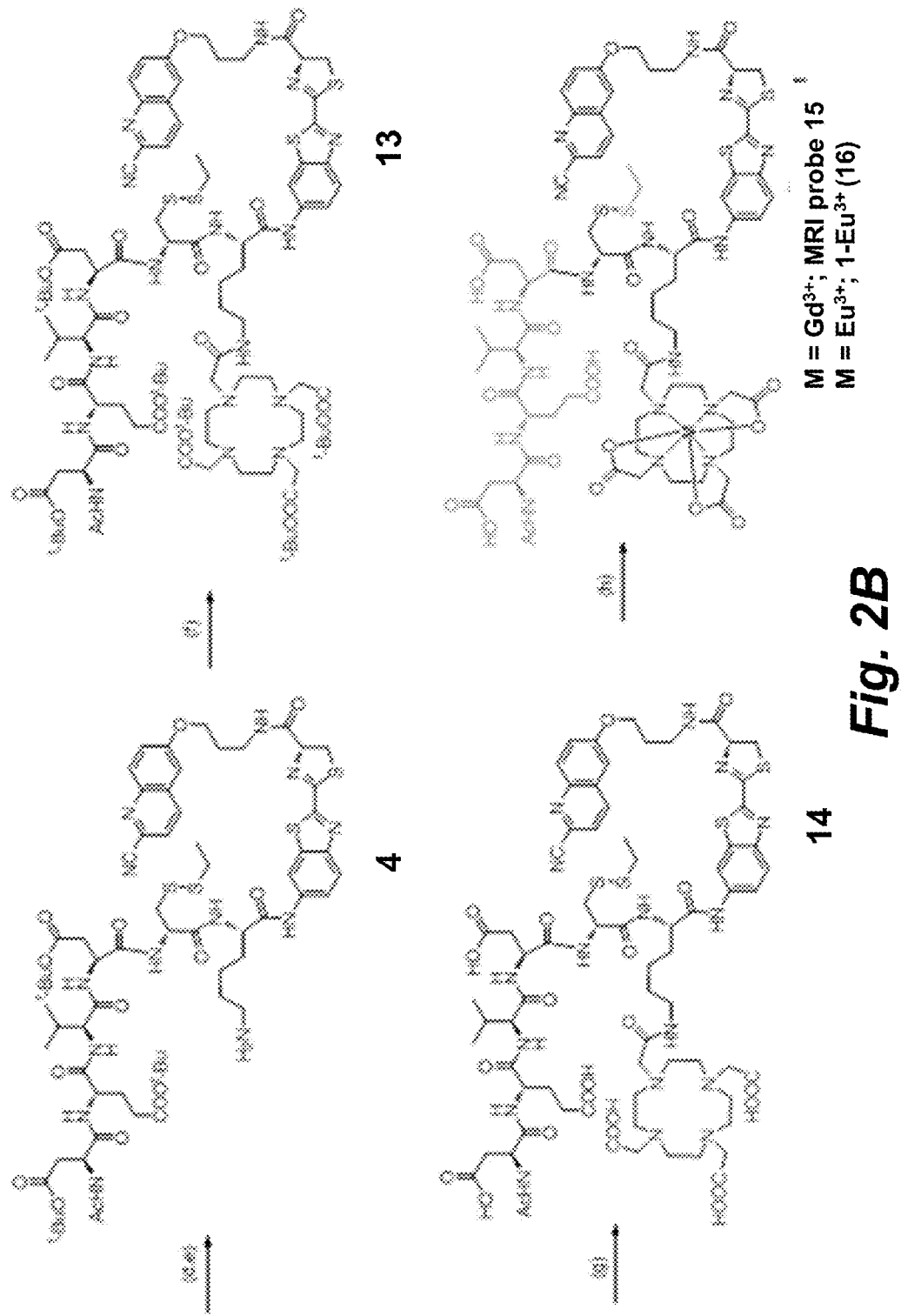
FIG. 2B illustrates a scheme for the synthesis of probes 15 and 16 from compound 4. (f) (t-BuO)$_3$DOTA-COOH, HBTU, DIPEA, DMF, 3 h; (g) TFA/TIPSH/DCM (95%/2.5%/2.5%); 56% in two steps; (h) GdCl$_3$.6H$_2$O or EuCl$_3$.6H$_2$O, NaHCO$_3$, pH 6-7, 75% for probe 15 and 79% for 1-Eu$^{3+}$ (16).
Figure 3A:
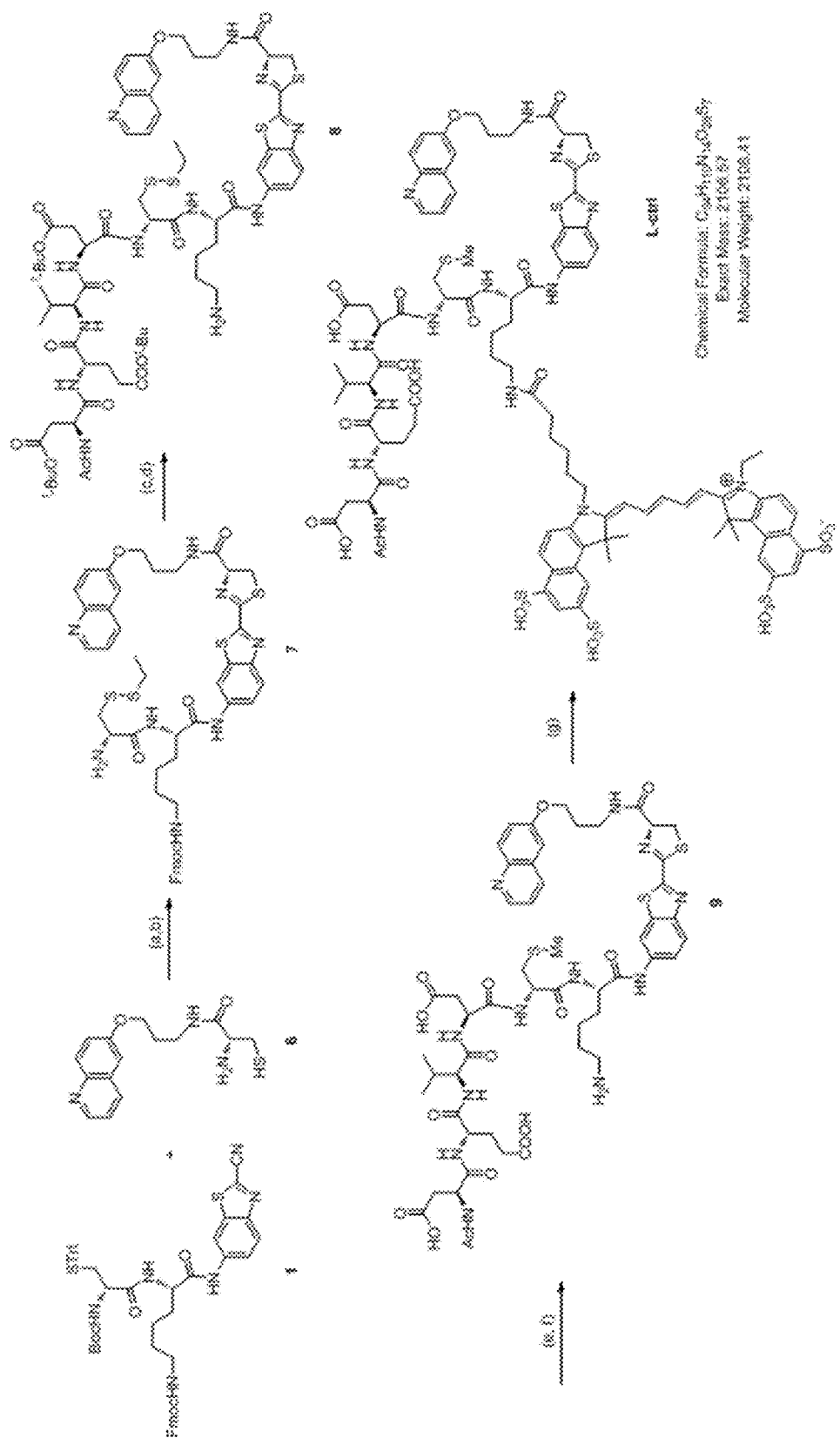
FIG. 3A illustrates a scheme for the synthesis of L-ctrl. Reaction conditions: (a) TCEP, DIPEA, DCM/MeOH, Ar, room temperature 1 h; (b) (i) 20% TFA/DCM; (ii) PySSEt, MeOH; (c) Ac-Asp(O$^t$Bu)-Glu(O$^t$Bu)-Val-Asp(O$^t$Bu)-COOH, HBTU, DIPEA, THF; (d) piperidine, DMF, 43% in two steps; (e) TFA/TIPSH/DCM (95%/2.5%/2.5%), 81%; (f) TCEP, NaHCO$_3$, MeI, 91%; (g) Cy 5.5-NHS, DMF, DIPEA, 51%.
Figure 3B:
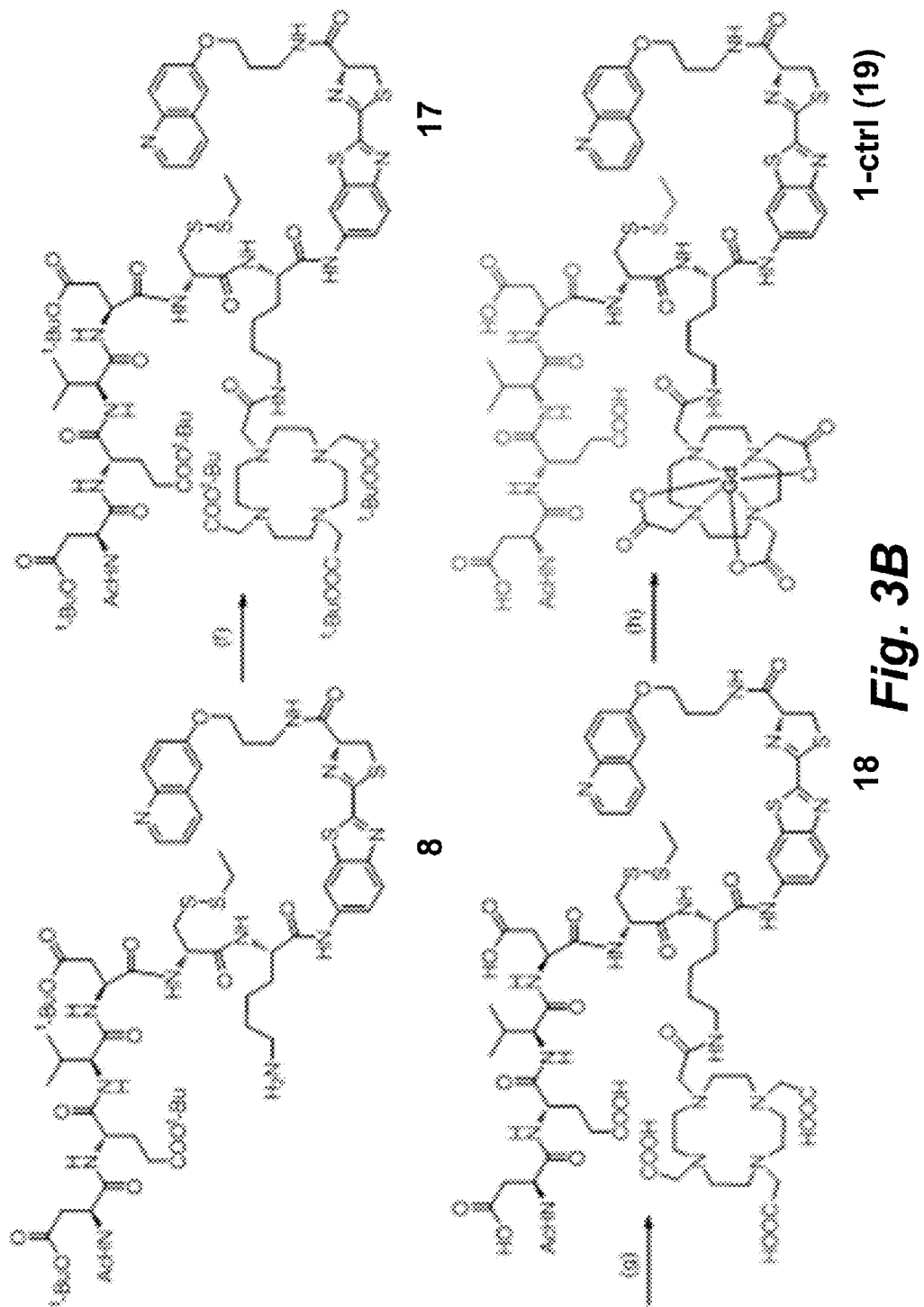
FIG. 3B illustrates a scheme for the synthesis of 1-ctrl (19) from (8): Reaction conditions: (f) (t-BuO)$_3$DOTA-COOH, HBTU, DIPEA, DMF, 3 h; (g) TFA/TIPSH/DCM (95%/2.5%/2.5%); 53% in two steps; (h) GdCl$_3$.6H$_2$O, pH 6-7, 82%.
Figure 4:
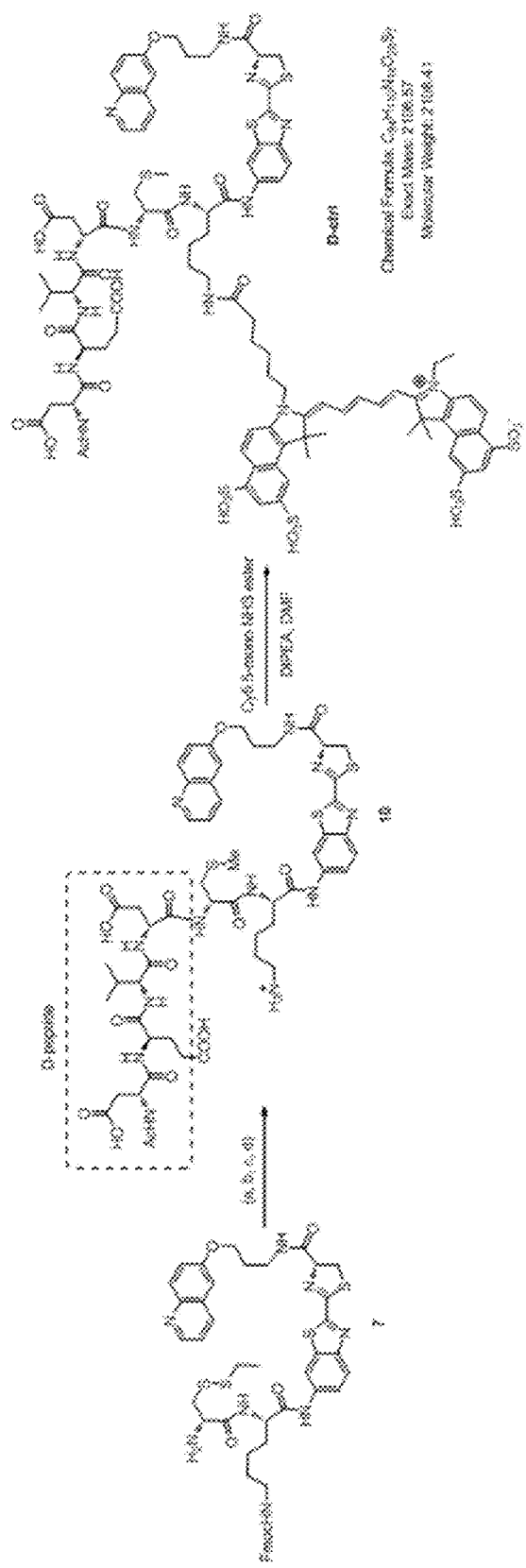
FIG. 4 illustrates a scheme for the synthesis of D-ctrl. Reaction conditions: (a) Ac-$_D$-Asp(O$^t$Bu)-$_D$-Glu(O$^t$Bu)-$_D$-Val-$_D$-Asp(O$^t$Bu)-COOH, HBTU, DIPEA, THF; (b) piperidine, DMF, 42% in two steps; (c) TFA/TIPSH/DCM (95%/2.5%/2.5%), 81%; (d) TCEP, NaHCO$_3$, MeI, 87%; (g) Cy 5.5-NHS, DMF, DIPEA, 47%.

A second control probe (D-ctrl), containing a D-DEVD sequence that is resistant to caspase-3/7 cleavage, allowed monitoring of the contribution of caspase-3-independent chemotherapy-induced tumor changes (i.e. perfusion changes) that could otherwise affect C-SNAF performance in vivo. These probes were synthesized and unambiguously characterized as outlined in the schemes as shown in FIGS. 2-4. An additional control, 1-ctrl (19) with an MRI contrast agent attached was also synthesised.

Caspase-3/7-Triggered Macrocyclization and Self-Assembly of C-SNAF In Vitro

Figures 8A, 8B:
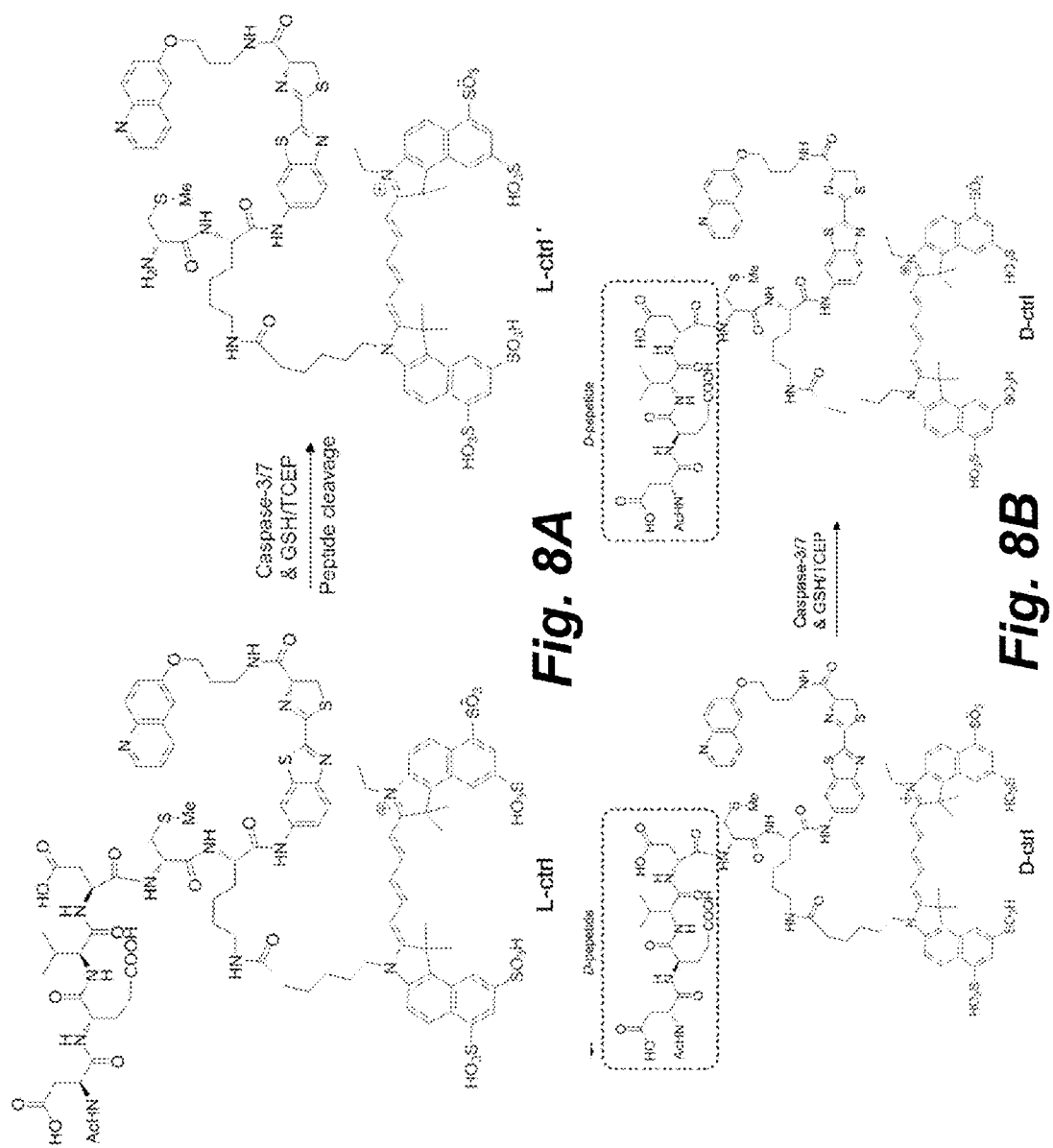
FIG. 8A is a scheme illustrating the molecular transformation of L-ctrl after incubation with caspase-3.
FIG. 8B is a scheme illustrating the molecular transformation of D-ctrl after incubation with caspase-3.

The progression of caspase-3-triggered macrocyclization of C-SNAF to form C-SNAF-cycl in solution was monitored using high-performance liquid chromatography (HPLC) following incubation of the probe (25 μM) with recombinant human caspase-3 (4.9×10$^{-3}$ μml). C-SNAF (TR=15.8 min) was efficiently converted to the pure cyclized product C-SNAF-cycl (TR=17.7 min) with fast reaction kinetics resulting in a half-life ($t_{1/2}$) of less than 1 h, as confirmed by HPLC (FIGS. 7A and 27A) and matrix-assisted laser desorption/ionization mass spectroscopic (MALDI-MS) analysis (FIG. 7B). C-SNAF and its disulfide bond-reduced intermediates were almost completely converted to C-SNAF-cycl after 6 h. Under the same conditions with L-ctrl, only the caspase-3-mediated DEVD-cleavage hydrolysis product (FIG. 8A) was observed. In contrast, when incubating D-ctrl with caspase-3, no new products were observed after 24 h (FIG. 8B).

Transmission electron microscope (TEM) images of C-SNAF-cycl from the reaction solution revealed that the Cy5.5-labeled macrocycles form nano-aggregates with an average diameter of 174±44 nm (FIG. 7C). No nano-aggregation was found in either of the control probe solutions after incubation with caspase-3. These in vitro results demonstrated that caspase-3 can induce C-SNAF to undergo intramolecular macrocyclization after proteolytic hydrolysis, resulting in nano-aggregation.

The specificity of C-SNAF towards other representative cysteine proteases such as caspase-7, caspase-9, cathepsin B, and legumain was examined. Monitoring the incubation of C-SNAF (25 µM) with equal masses of individual recombinant enzymes (0.735 µg/ml) using HPLC unambiguously revealed the high selectivity of the probe toward effector caspases-3 and -7, which share the same peptide substrate specificity (Johnson et al., (2012) *Bioconjugate Chem.* 23: 1783-1793; Maxwell et al., (2009) *Bioconjugate Chem.* 20: 702-709) (FIG. 7B). The initiator caspase-9 showed essentially no activity towards C-SNAF. Moreover, neither lysosomal cysteine proteases cathepsin B nor legumain could significantly activate C-SNAF, even in light of recent reports showing their potential to recognize the DEVD peptide sequence (Edgington et al., (2011) *Curr. Opin. Chem. Biol.* 15; 798-805; Edgington et al., (2009) *Nat. Med.* 15: 967-9730).

Imaging Caspase-3/7 Activity in Drug-Treated Cancer Cells in Culture

The intracellular accumulation and retention of caspase-3/7-activated C-SNAF was investigated in cultured HeLa human cervical cancer cells and MDA-MB-231 human breast cancer cells following treatment with either the broad-spectrum protein kinase inhibitor staurosporine (STS) (Stepczynska et al., (2001) *Oncogene* 20; 1193-1202) or the widely clinically used first-line chemotherapy agent, doxorubicin (DOX) (Wang et al. (2004) *J. Biol. Chem.* 279: 25535-25543).

After the validation of the apoptosis cell model, flow cytometry was employed to interrogate the capability of C-SNAF for specifically labeling apoptotic tumor cells in vitro. Co-labeling experiments were carried out in STS-treated HeLa cells incubated with C-SNAF, L-ctrl, or D-ctrl, followed by incubation with FLICA, a recognized standard marker of caspase-3-mediated apoptosis, as shown in FIG. 11A. The FLICA-positive apoptotic cells were also efficiently labeled by C-SNAF, but not by control probes, demonstrating a good correlation between C-SNAF and FLICA.

Figures 9A, 9B:
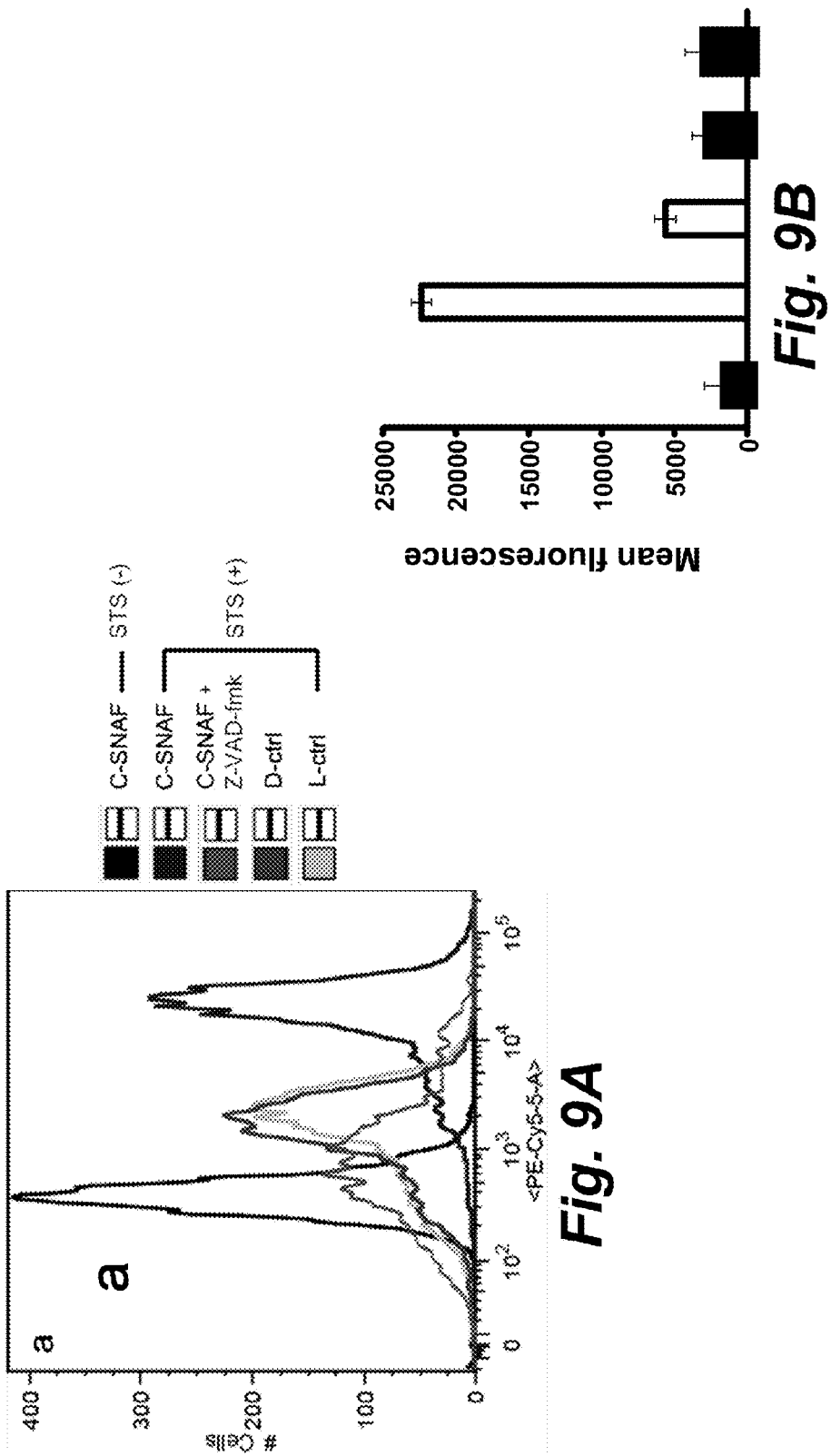
FIG. 9A illustrates overlay histograms from flow cytometry showing high Cy5.5 fluorescence in the apoptotic cells after incubation with 2 μM C-SNAF.
FIG. 9B illustrates the quantitation of the fluorescent intensity of Cy5.5 in cells as derived from the flow cytometry analysis shown in FIG. 9A, and shows that apoptotic cells labeled with C-SNAF have approximately a 13-fold increased intensity compared to viable cells incubated with C-SNAF. The increased fluorescence was inhibited by the caspase-3/7 inhibitor Z-VAD-fmk (50 μM). Apoptotic cells incubated with 2 μM control probes L-ctrl and D-ctrl showed much lower fluorescent intensity. Error bar comes from two separate experiments.

Labelling of apoptotic cells by both FLICA and C-SNAF was inhibited by the caspase-3 inhibitor Z-VAD-fmk, confirming the effector caspase-specific activation of C-SNAF. C-SNAF labeling of apoptotic cells resulted in a nearly 13-fold increase in the Cy5.5 fluorescence relative to viable cells, which was also inhibited by Z-VAD-fmk (as shown in FIGS. 9A and 9B). DOX-incubated HeLa cells gave similar results (FIGS. 10A and 10B).

Apoptotic HeLa cells labeled with C-SNAF were investigated by fluorescence microscopy. C-SNAF accumulated extensively in the cytosol of most of the apoptotic cells, while only negligible fluorescence was observed in either viable cells or apoptotic cells pre-treated with Z-VAD-fmk (FIG. 11B). The labeling of apoptotic cells by C-SNAF was both drug concentration- and incubation time-dependent, showing an approximately 4-fold enhancement in cell labeling efficiency (23 to 90%) with a paralleled 4-fold increase in STS dose level (0.5 to 2 µM).

This dose-dependence was recapitulated with DOX, resulting in an approximately 10-fold enhancement in cell labeling efficiency (9 to 92%) with a paralleled 5-fold increase in dose level (1 to 5 µM). Apoptotic cells incubated with L-ctrl or D-ctrl showed relatively weaker fluorescence as compared to C-SNAF (FIGS. 11B and 10B), which corroborates the results obtained from flow cytometry (FIG. 11A). Similar imaging results were observed in STS-treated MDA-MB-231 cells, demonstrating the cell type-independent nature of C-SNAF activation. Overall, these results demonstrate that C-SNAF can image tumor cell response to chemotherapy in a cell-type independent but caspase-3/7-dependent manner.

To confirm the formation of the caspase-3/7-triggered intramolecular cyclization product C-SNAF-cycl in apoptotic cells, C-SNAF (5 µM) was incubated with both cell lysates and whole cells, and the products were analyzed by HPLC. The incubation of C-SNAF with viable cell lysate resulted in the major products of glutathione (GSH)-induced disulfide reduction and some condensation products of CHQ with endogenous free cysteine. However, more than 90% of C-SNAF was converted to C-SNAF-cycl in the lysate of STS- and DOX-induced apoptotic HeLa (FIG. 12A) or MDA-MB-231 cells, indicating the efficient intramolecular condensation initiated by caspase-3/7 in a complex cellular environment. Moreover, HPLC analysis of whole HeLa cells induced to apoptosis by STS treatment prior to exposure to C-SNAF (50 µM) identified the cyclized C-SNAF-cycl after 24 h incubation, but this cyclic product was not detected from viable HeLa cell pellets (FIG. 12B). Collectively, these results provide evidence for the caspase-3/7 induced intramolecular macrocyclization of C-SNAF in apoptotic tumor cells, which results in enhanced probe retention.

Figure 5:
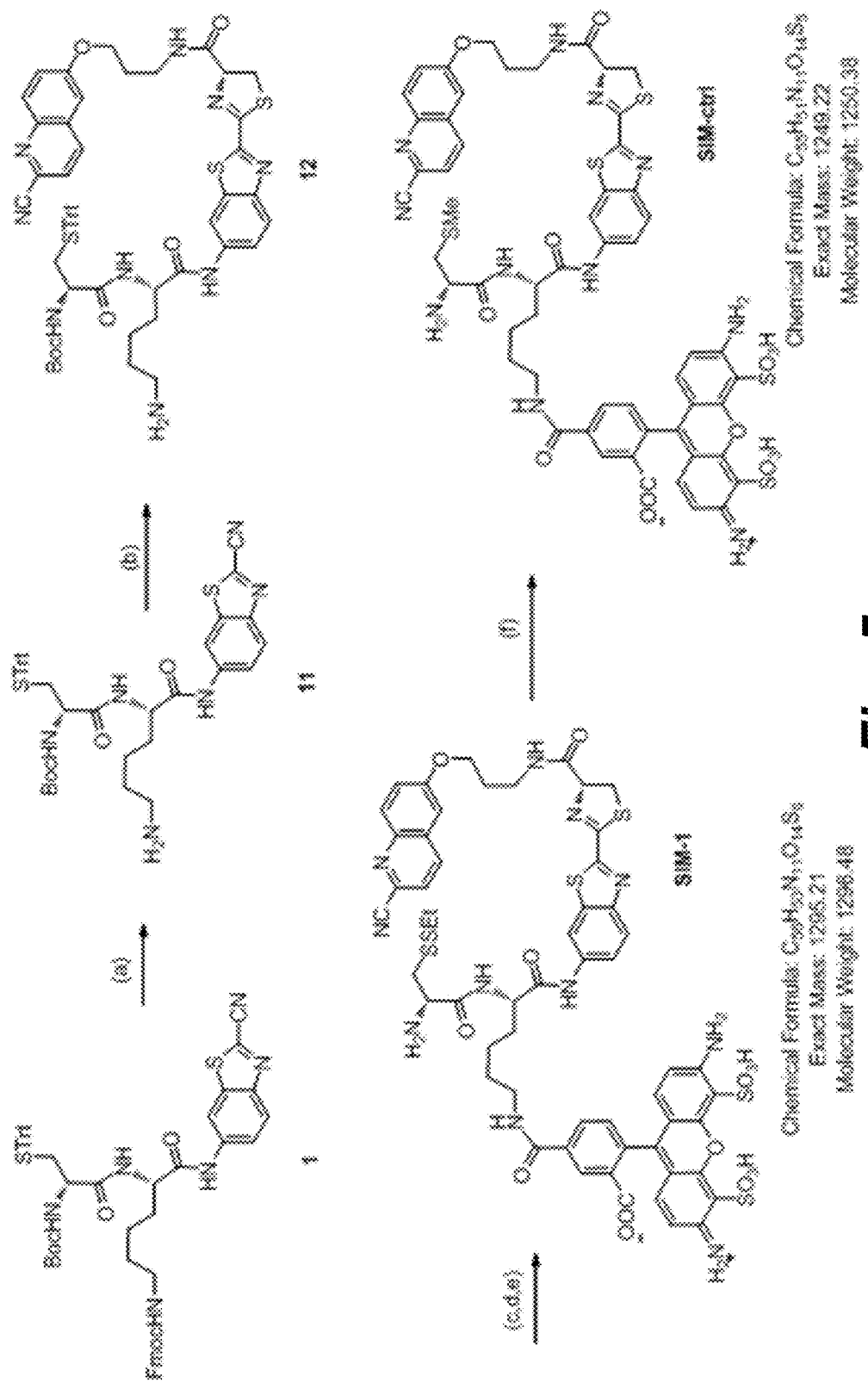
FIG. 5 illustrates a scheme for the synthesis of high-resolution imaging probe SIM-1 and control probe SIM-ctrl. Reaction conditions: (a) piperidine, DMF, 63%; (b) TCEP, DIPEA, DCM/MeOH, Ar, room temperature 1 h; (c) Alexa Fluor 488 5-TFP, DIPEA, DMF; (d) TFA/TIPSH/DCM (25%/72.5%/2.5%); (e) PySSEt, MeOH; (f) TCEP, NaHCO$_3$, MeI.

Direct Observation of In Situ Formed Nanoparticles in Cells by Super-Resolution Microscopy To provide direct evidence for the in situ nano-aggregation of C-SNAF inside cells, three-dimensional structured illumination microscopy (3D-SIM) was used to enable high-resolution imaging of these self-assembled products (Schermelleh et al., (2008) *Science* 320: 1332-1336; Westphal et al., (2008) *Science* 320: 246-249). An Alexa 488-labeled probe SIM-1, meeting the photostability requirements for SIM, was first synthesized (as schematically shown in FIG. 5) to undergo macrocyclization and nano-aggregation following intracellular GSH-reduction.

The incubation of SIM-1 (0.5 mM) with STS-treated HeLa cells resulted in strong and punctate fluorescence distributed throughout individual cells under SIM with an average aggregate size of about 180 nm on x-y plane (n=30). These fluorescent particles were not observed in apoptotic cells incubated with the non-cyclizable control probe SIM-ctrl. Furthermore, SIM imaging revealed the selective nano-aggregation of a caspase-3/7-sensitive probe, C-SNAF-SIM, following incubation with apoptotic cells, but not in viable cells. These fluorescent nanoparticles were distributed throughout both the cytosol and in emerging apoptotic bodies (FIG. 13).

Similar to SIM-1, the average nano-aggregate size for C-SNAF-SIM was approximately 150 nm on the x-y plane (n=50), which approximates the size of the nano-aggregates observed by TEM (about 170 nm). Therefore, direct SIM imaging confirmed the capacity of in situ nano-aggregation of C-SNAF in apoptotic cells.

Non-Invasive Monitoring of Apoptosis in Tumor-Bearing Mice Treated with DOX

The amenability of C-SNAF to in vivo molecular imaging was assessed in healthy nude mice. C-SNAF showed rapid clearance from the circulation with a blood half-life of 1.0±0.45 h, which was not significantly different from L-ctrl (0.5±0.28 h) (p>0.05) (FIG. 14A). This was in good agreement with the biodistribution data of C-SNAF (FIG. 14B). A high kidney uptake with little accumulation in other organs indicated predominantly renal clearance of the small molecule probe. Nearly complete elimination of C-SNAF occurred by 12 h after administration. An investigation of the integrity of C-SNAF, L-ctrl, and D-ctrl in mouse serum demonstrated a good stability amenable to in vivo imaging, with half-lives of more than 6 h.

To demonstrate the feasibility of C-SNAF to monitor tumor response to chemotherapy in vivo, female nude mice bearing subcutaneous HeLa tumors received either intravenous chemotherapy consisting of three doses of 8 mg/kg DOX (3×DOX)44 or saline (FIGS. 15A, 16A and 16B). C-SNAF or either of the control probes (5 nmol) was administered intravenously to tumor-bearing mice and whole animal fluorescence was longitudinally monitored using a Maestro fluorescence imager. C-SNAF showed significantly brighter signals in DOX-treated as compared to saline-treated tumors (FIG. 15B) (n=5, p<0.05).

The fluorescence in tumors reached a maximum 1 h after administration of C-SNAF, and at 4 h there was a significant 1.6-fold increase in fluorescence signal in DOX-treated tumors compared to saline-treated mice (FIG. 15C). In DOX-treated mice, both L-ctrl and D-ctrl produced tumor fluorescence at 1 h that was 18% and 10% lower than that of C-SNAF, respectively. Neither control probe resulted in a significant increase in fluorescent signal relative to their saline-treated counterparts (P>0.05) (FIGS. 15B, 17A, and 17B). 4 h after probe administration the average signal enhancement of L-ctrl and D-ctrl between DOX- and saline-treated tumors was only 0.24% and −12%, respectively.

Extensive ex vivo analyses were performed to investigate the association of caspase-3 activation as a marker for tumor chemotherapeutic response with enhanced tumor retention of C-SNAF. First, immunohistochemistry was performed on tumors treated with saline or 3×DOX and resected 4 h after probe injection, as shown in FIG. 18A. Both the levels of active caspase-3 and the degree of C-SNAF retention were lower in saline-treated mice relative to those receiving DOX. Additionally, the spatial pattern of enhanced probe retention in the tumors of DOX-treated animals matched well that of the distribution of active caspase-3 in tumor tissue. Second, HPLC analysis detected a significantly greater amount of C-SNAF-cycl in DOX-treated relative to saline-treated tumor lysates (FIG. 18C), confirming cyclization occurred in living mice.

These results indicated: (1) the accumulation of both control probes in tumors is treatment-independent, (2) only C-SNAF shows specific labeling of apoptotic tumors responding to chemotherapy, and (3) that the probe undergoes caspase-triggered macrocyclization and nano-aggregation to generate enhanced contrast for imaging apoptotic tumors in vivo.

To demonstrate the capability of C-SNAF to differentiate the degree of tumor response to chemotherapeutic intervention in the same individual mouse, C-SNAF was administered and fluorescence imaging was performed two days following both the first and the third treatment with DOX. Following a single dose of DOX (1×DOX), a moderate but not statistically significant increase in tumor fluorescence intensity relative to saline-treated mice could be detected (FIG. 15D). There was, however, a significant enhancement in fluorescence intensity following the third round of DOX therapy in the same group of animals relative to both saline and a single DOX treatment (p<0.05) (FIG. 15D). The significance of the imaging results paralleled that of the observed tumor size changes, where no significant difference in average tumor volume was noted after a single treatment of DOX, but a significant reduction in tumor growth rate in mice followed the third round of chemotherapy (3×DOX, FIG. 16A). There is a strong correlation (r=−0.9, p<0.05) between the maximum tumor fluorescence signal produced after the administration of C-SNAF and the maximum tumor volume change observed following chemotherapy (FIG. 18C). No such correlation was observed in saline-treated mice (FIG. 18C), nor for either control probe after 3×DOX treatment (FIG. 18D). These results suggest the ability of C-SNAF to provide information regarding the degree of response of an individual tumor to received therapy, and not just a binary indication of the induction of apoptosis.

The present disclosure shows the in situ self-assembly of small molecules in living mice through imaging tumor response to chemotherapeutics. The self-assembly chemistry of the disclosure is enabled by a biocompatible cyclization reaction between free cysteine and CHQ groups, which shows a concentration-independent and kinetically fast ($6 \times 10^{-3}$ s$^{-1}$) intramolecular condensation (Ye et al., (2011) *Angew. Chem. Int. Ed.* 50: 2275-2279). This first-order reaction allows for macrocyclization to proceed efficiently in physiological environments independent of local probe concentrations, which is advantageous for controlled self-assembly in vivo over the intermolecular reactions, including the originally reported condensation system based on CBT and cysteine (Liang et al., (2010) *Nat. Chem.* 2: 54-60). The cysteine concentration in human blood is generally around 10-100 mM (Brigham et al., (1960) *J. Clin. Invest.* 39: 1633-1638; Salemi et al., (2009) *Neurol. Sci.* 30: 361-364), which may additionally compromise the ability of the CBT-based system to undergo intermolecular condensation in vivo (Cao et al., (2013) *Sci. Rep.* 3: 1024). In contrast, the transition from inter- to intramolecular condensation between CHQ and cysteine moieties of the probes of the disclosure effectively outcompetes free cysteine and has resulted in efficient controlled self-assembly in vivo.

A set of control probes, D-ctrl and L-ctrl, were designed and evaluated to conclusively demonstrate the occurrence and requirement of macrocyclization for self-assembly. Since D-ctrl is inert to caspase activation and remains unchanged, its lack of efficacy precludes the significant contribution of changes to tumor physiology other than caspase-3/7 activation to the mechanism of C-SNAF action. The lack of successful imaging by L-ctrl, which can undergo enzyme cleavage but neither macrocyclization nor in situ nano-aggregation, clearly indicates (1) the necessity of macrocyclization, and (2) the inability of mere cleavage of the DEVD capping peptide to account for the mechanism of C-SNAF action. The direct super-resolution visualization of nano-aggregated fluorescent products of both a reduction-triggered SIM-1 probe, but not the non-cyclizable SIM-ctrl, and a caspase-3/7-targeted cyclizable probe C-SNAF-SIM in apoptotic cells, but not in viable cells supports this. Size matching of the particles inside cells observed by SIM with that found by TEM unambiguously establishes the mechanism of triggered nano-aggregation in cells.

Applying the self-assembly strategy to molecular imaging probe design offers significant advantages over existing strategies in that it combines the advantages of small molecules with those of nanomaterials. The small size of the probe ensures deeper tissue penetration and more extensive biodistribution (Wysocki & Lavis (2011) *Curr. Opin. Chem. Biol.* 15: 752-759). The in situ nano-aggregation affords the activated probe a longer residence time in the target tissue of interest (Merian et al., (2012) *Molecules* 17: 5564-5591) (e.g. apoptotic tumor tissue).

Finally, the proteolytic process of probe activation is bioorthogonal, permitting the continued activity of target enzymes to result in the activation of orders of magnitude more probe molecules per single enzyme activation event. This signal amplification occurs in contrast to inhibitor-based probes that otherwise shut down the target enzyme after the activation of a single probe molecule and concomitantly interrupt regular cell function (Edgington et al., (2011) *Curr. Opin. Chem. Biol.* 15; 798-805).

The high specificity of C-SNAF for caspase-3/7 relative to initiator caspases (i.e., caspase-9) and other off-target proteases (i.e., cathepsin B and legumain) (FIG. 7B) is an advantage over previously designed caspase-3 activity-based probes, which show strong cross-reactivity with legumain, a non-specific protease (Edgington et al., (2009) *Nat. Med.* 15: 967-973; Berger et al., (2006) *Mol. Cell* 23: 509-521). C-SNAF was also capable of differentiating the degree of tumor response in the same animal throughout the course of chemotherapy, with an increase in tumor fluorescence as mice progressed from the first (1×DOX) to the third (3×DOX) round of treatment, as shown in FIG. 15D. Moreover, the degree of maximum tumor fluorescence from C-SNAF strongly correlated with the maximum tumor size change at the end of chemotherapy. The capability to evaluate the degree of tumor response both longitudinally in a single mouse and relative to other mice receiving treatment provides valuable information regarding the response of an individual to applied therapy. This, in conjunction with the rapid, real-time, and non-invasive acquisition of this information suggests the possibility that C-SNAF may close a critical gap in the clinical delivery of personalized cancer medicine.

Similar to other fluorescent probes in the perpetually 'on' state regardless of activation, a high background signal in non-apoptotic tissues was observed with C-SNAF, resulting in comparable intensities of maximum fluorescence emission from tumors of mice administered C-SNAF, or L-ctrl or D-ctrl (FIGS. 15B, 17A, and 17B, respectively). This limitation can be overcome by introducing a fluorescent quencher moiety to the probe, initially silencing the probe prior to activation by the target enzyme.

Accordingly, through the design of a series of in vitro and in vivo experiments, we unambiguously demonstrate in situ self-assembly of a small-molecule probe enabled by a bioorthogonal cyclization reaction in living mice. This strategy provides an imaging probe that combines the advantages of small molecules with those of nanomaterials for imaging of caspase-3/7 activity in vivo. The enhanced accumulation and retention of the in situ formed nano-aggregates results in high tumor contrast for non-invasive, in vivo imaging of apoptosis and a potential for application to related diseases, such as neurodegenerative diseases and organ transplant rejection. The same strategy can be amenable to other enzyme targets and imaging modalities such as, but not limited to, positron emission tomography and magnetic resonance imaging.

PET Imaging Tracers

The biocompatible condensation reactions according to the disclosure that generate self-assembled nano-aggregation after enzyme activation are also advantageous as PET tracers for imaging enzymatic activity. In one embodiment, an $^{18}$F-labeled caspase-sensitive nano-aggregation PET tracer ([$^{18}$F]C-SNAT (1) includes a 2-cyano-6-hydroxyquinoline (CHQ) and a cysteine residue whose amino group is coupled to the peptide substrate of caspase-3, DEVD, and whose mercapto group of its side chain is converted to a disulfide bond.

[$^{18}$F]C-SNAT (1) compares favorably to known apoptosis PET tracers (Table 1) with the highest tumor/muscle ratio in apoptotic tumors, and the highest ratio of uptake value (% ID/g) between apoptotic and non-treated tumors.

TABLE 1

| Tracer | Species | Probe Mechanism | Origin of Apoptosis | % ID/g at target site | [a]Target/Background | Treated/Untreated | Ref.[g] |
|---|---|---|---|---|---|---|---|
| [$^{18}$F]C-SNAT | Mouse | Caspase-3 | Tumor treatment | 1.3 ± 0.1 | 7.0 | 1.9[b] | |
| [$^{18}$F]Annexin V | Mouse | PS binding | Tumor treatment | 1.56 ± 0.2 | 3.4 | 1.6[b] | [2] |
| [$^{18}$F]ICMT-11 | Mouse | Caspase-3 Inhibitor | Tumor treatment | N/A | 1.2[c] | 1.5[d] | [3] |
| [$^{18}$F]-CP18 | Mouse | Caspase-3 activated | Tumor endogenous apoptosis | 0.17 | 10.2 | N/A | [4] |
| [$^{18}$F]WC-IV-3 | Rat | Caspase-3 Inhibitor | Anti-Fas liver injury | 6.80 ± 3.0[e] | 4.3 | 3.2[d] | [4] |
| [$^{18}$F]ML-10 | Mouse | Membrane Potential | Cerebral stroke | 0.3 ± 0.1 | N/A | 2.3[f] | [5] |

[a]The maximum values reported at the apoptotic tissue.
[b]target uptake ratio between pre and post treatment in same animal.
[c]Tumor/blood.
[d]target uptake ratio between treated and untreated group in different animal.
[e]Quantified by ex vivo bio-distribution, other data in this column are quantified by PET imaging.
[f]target uptake ratio between stroke and non-stroke region in same animal; PS: phosphatidylserine.
[g][2] Hu et al., (2012) *Mol. Imaging Biol.* 14: 762-770
[3] Nguyen et al., (2009) *Proc. Natl. Acad. Sci. USA* 106: 16375-16380
[4] Xia et al., (2013) *Nucl. Med. Biol.* DOI: 10.1007/s11307-013-0646-7
[5] Chen et al., (2012) *Nucl. Med. Biol.* 39: 137-144
[6] Reshef et al., (2008) *J. Nucl. Med.* 49: 1520-1528

Consistent with the mechanism, [$^{18}$F]-C-SNAT showed a trend of increasing uptake over times (FIG. 23A) in aprptotic tumors and thus increases differences between treated apoptptoc and non-treated tumors at later time points. This trend has not been observed with other apoptosis PET tracers; for example, with [$^{18}$F]-ICMT-11, a PET tracer that binds active caspase-3, the uptake at the apoptotic tumors decreased over the time after injection (Nguyen et al., (2009) *Proc. Natl. Acad. Sci. USA* 106: 16375-16380).

Furthermore, it is contemplated as a general strategy for developing PET tracers for imaging the activity of other enzymes that the probe compositions of the disclosure are advantageous for use in detecting and imaging enzyme activities other than caspase-3 or caspase 7. For example, but not intended to be limiting, the capping moiety of the probes may be attached to the self-cyclizing moiety by a peptide or other bond that can be selectively cleaved by another protease or peptidase, such as, but not limited to, a furin, MMPs, and the like.

Caspase-Activated MRI Contrast Agents

The present disclosure further encompasses activatable MRI contrast agents based on the mechanism of enzyme-activated intramolecular cyclization and subsequent self-assembly into MRI-detectable nanoparticles (GdNPs). For example, but not intended to be limiting, the MRI-detectable labeling moiety attached to the caspase-activatable nanoparticles can be gadolinium, thulium, europium, or similar metal ion. Such metal ions may be attached to the activatable nanoparticles by a chelating agent linker covalently bonded the activatable composition.

Following caspase-3 activation, for example, GdNPs can show an increase in $r_1$ relaxivity relative to the unactivated probe due to an increased i$\tau_R$. One embodiment of an MRI contrast agent of the disclosure, the MRI probe 15 consists of: a 2-cyano-6-hydroxyquinoline (CHQ) and a D-cysteine residue for efficient biocompatible cyclization, a DEVD peptide recognized by active caspase-3, a disulfide bond reduced by intracellular glutathione, and a Gd-DOTA chelate as the MRI reporter.

After intravenous administration, the relatively small size of the probe 15 can rapidly extravasate and penetrate into tumor tissue. When in apoptotic tumor cells, active caspase-3 can cleave the DEVD capping group, and the reductive intracellular microenvironment would reduce the disulfide, the combination of which would initiate the intramolecular cyclization reaction. Unlike the flexible precursor probe, the macrocyclic product is more rigid and hydrophobic, and can further self-assemble into GdNPs. In addition to their enhanced $r_1$ relaxivity, the GdNPs have a prolonged retention in chemotherapy-responsive tumors due to their large size. Both of these features can enhance the resultant MRI contrast for in vivo applications.

The control probe 1-ctrl (19) was designed to have a similar structure to probe 15, but with a quinolin-6-yl ring replacing the CHQ moiety, preventing intramolecular cyclization following DEVD peptide cleavage by caspase-3 and abrogating GdNP formation. Therefore, 1-ctrl (19) can allow for the interrogation of the relative contribution of peptide cleavage versus triggered self-assembly to the mechanism of MR contrast enhancement.

The progression of caspase-3-triggered intramolecular cyclization of probe 15 in solution was investigated by incubation (200 µM) with recombinant human caspase-3 (50 nM) using high-performance liquid chromatography (HPLC). Probe 15 was shown to efficiently cyclize and form two cyclized isomers and with fast reaction kinetics, as confirmed by HPLC and high resolution mass spectroscopic (HRMS) analysis, as shown in FIG. 27A. More than 90% of probe 15 and its disulfide bond reduced intermediates could be converted after 5 h (FIG. 27B). In contrast, when incubating 1-ctrl (19) with caspase-3, only the DEVD peptide cleaved and disulfide reduced product was observed.

The formation of GdNPs in solution after caspase-3 activation was measured by dynamic light scattering (DLS), showing the aggregation of particles with a mean diameter of approximately 190 nm. Transmission electron microscopy (TEM) showed the shapes of separated GdNPs with diameters ranging from 50 to a few hundred nanometers. TEM images also showed a darker contrast at the edge of particles indicating a higher density of gadolinium ions at the surface. The exposure of Gd-chelates to the surface of formed GdNPs ensures solvent accessibility and water exchange to generate a more efficient relaxation of water protons.

Water proton $r_1$ relaxivities of probe 15 and 1-ctrl (19) before and after caspase-3 incubation were then measured at 1, 1.5 and 3 T. For comparison, the isolated cyclized products 2-I and 2-II were also measured.

The relaxivities of 15 and 1-ctrl (19) were similar and higher than Dotarem at all three magnetic fields. The larger relaxivities correspond to a larger molecular size of 15 and 1-ctrl (19) compared to Dotarem, resulting in a longer $\tau_R$. Upon caspase-3 incubation, enhanced relaxivity for probe 15 was observed, probably due to a further increase in $\tau_R$ resulting from the formation of GdNPs in solution. The $r_1$ value of probe 15 upon caspase-3 activation was approximately 29.3 mM$^{-1}$ s$^{-1}$ at 1 T, which is about 106% higher than that of probe 15 before activation (14.2 mM$^{-1}$ s$^{-1}$), and about 510% higher than Dotarem (4.8 mM$^{-1}$ s$^{-1}$). In contrast, after incubation with caspase-3, 1-ctrl (19) gave slightly reduced relaxivities (14% at 1 T), which is expected given the decreased size of the cleaved, but non-cyclized, products. Thus, caspase-3 activated self-assembly of cyclized products from probe 15 into GdNPs, but not cleaved products from 1-ctrl (19), generates higher per Gd relaxivity at lower magnetic field strengths. The higher relaxivity of probe 1 after caspase-3 activation was further demonstrated. Moreover, the isolated cyclized products 2-I and 2-II gave similar relaxivities compared to probe 15 upon caspase-3 incubation, indicating a high efficacy for capase-3 activation.

The enzyme specificity of probe 15 was studied by measuring the $T_1$ value resulting from probe incubation (208 µM) with any of five relevant subcellular proteases (caspase-3, -7, -9, cathepsin B and legumain) in enzyme buffer. As shown in FIG. 27D, a similar reduced $T_1$ value was observed for caspases-3 and -7, which are activated during cell apoptosis and capable of cleaving the same DEVD peptide sequence. The reduced $T_1$ value in solution was inhibited by the caspase inhibitor Z-VAD-fmk (50 µM). No reduced $T_1$ value was observed for initiator caspase-9, or off-target lysosomal proteases (cathepsin B and legumain), indicating a selectivity of probe 15 for cell apoptosis imaging.

A $T_1$-weighted image (1 T) of probe 15 with these enzymes showed brighter signal following incubation with caspase-3 and -7. Additionally, probe 15 (200 µM) can detect as low as 5 nM of caspase-3 in solution according to $T_1$ value measurements (FIG. 27E), which is comparable to reported results with the PARACEST® MRI probe.

To image apoptotic cells with probe 15, the cytotoxicity of 15 was first evaluated by incubation of viable HeLa cells at 250 µM for 24 h, which showed no adverse effects on cell viability. Apoptotic HeLa cell models were obtained by treating HeLa cells with staurosporine (STS, 2 µM) for 4 h, followed by further incubation in blank medium for another 24 h. Caspase-3 assays confirmed that the lysates of STS-treated cells showed approximately a 10.5-fold higher caspaes-3 activity than that of non-treated cells, which can efficiently convert probe 15 to 23.

The enhanced caspase-3 activity was further confirmed by incubation of STS-treated and non-treated HeLa cells with a fluorescent probe 1-FITC (22), in which an FITC fluorophore was introduced to replace the Gd-DOTA chelate in probe 1. Caspase-3 can trigger 1-FITC (22) to form similar cyclized products and subsequent nano-aggregation, which can result in a brighter fluorescence signal retained inside apoptotic cells. As shown in FIG. 28A, an intense fluorescence was observed only in STS-treated cells, indicating a higher caspase-3 activity in these cells.

The cellular uptake of Gd was studied by inductively-coupled plasma mass spectrometry (ICP-MS) analysis of the amount of Gd in viable and apoptotic cells after incubation with probe 15 (50-250 μM) for 24 h. As shown in FIG. 28B, the cellular uptake of Gd in STS-treated cells was 6.6-fold that of non-treated cells with 250 μM of probe 15. This uptake enhancement was inhibitable by Z-VAD-fmk (50 μM), confirming the caspase-3-dependent accumulation of probe 15 in apoptotic cells. As a control, the incubation of STS-treated cells with either 1-ctrl (19) or Dotarem gave much lower uptake of Gd. The cellular uptake of probe 15 was also confirmed directly by two-photon laser confocal microscopy imaging of its europium analogue (1-$Eu^{3+}$ (16)) under the same conditions, producing a strong fluorescent signal in apoptotic cells.

An MRI study of the cell pellets at 1 T showed a significantly (about 3-fold) reduced $T_1$ value in STS-treated cells after incubation with probe 15 as compared to non-treated cells. There was no significant reduction in $T_1$ between STS-treated and non-treated cells incubated with Dotarem. The much shorter $T_1$ value was consistent with the results of $T_1$-weighted images of cell pellets, as shown in FIG. 28D, where STS-treated cells appeared brighter than non-treated cells after incubation with probe 15. Thus, higher caspase-3 activity in apoptotic cells can trap probe 15 inside cells, resulting in higher MRI contrast for cell apoptosis imaging.

Evaluation of activatable contrast agent probe 15 for MR imaging of caspase-3 activity in vivo was performed in nude mice bearing subcutaneous HeLa tumors. Tumors were implanted and grown for 10-15 days before receiving intratumoral injections of two doses of 0.2 mg doxorubicin separated by 2 days. Probe 15 or 1-ctrl (19) (0.1 mmol $kg^{-1}$) was injected intravenously the day before treatment (baseline) and four days post-treatment (treated). Spin-echo $T_1$-weighted multislice MR images at 1 T were recorded before (pre-contrast) and every 4 min after contrast agent administration (post-contrast), and scanning was carried out for 4 h post-contrast for each mouse. Much brighter MR signals ($T_1$ contrast) were observed 40 and 120 min after injection with probe 15 in treated tumors as compared to that in baseline tumors (FIG. 29A), or in treated tumors with 1-ctrl (19) (FIG. 29B). The signal intensity (SI) enhancement in treated tumors reached a maximum 40 min after administration of probe 15, which was significantly higher than that of baseline tumors (n=8, p<0.05, FIG. 29C).

In contrast, there was no significant difference in SI enhancement during the time-course imaging (up to 4 h) between treated and baseline tumors after 1-ctrl (19) administration (n=4, p>0.05, FIG. 29C). The SI enhancement in treated mice 120 min after injection with probe 15 was 77% higher than that with 1-ctrl (19). Moreover, the analysis of % difference in tumor SI enhancement after administration of probe 15 revealed a prolonged accumulation of contrast material in treated tumor compared to baseline tumor; the % difference increased from 62% at 20 min to 169% after 120 min (FIG. 29C). These findings are consistent with the formation of GdNPs triggered by caspase-3 resulting in prolonged retention in regions of apoptosis relative to inactivated contrast agent. This is also supported by the results of ICP-MS analysis of Gd uptake in tumors, showing a higher Gd level in treated tumors after injection of probe 15. The SI enhancement in treated tumors with probe 15 correlated well with the caspase-3 level detected in tumors, suggesting the advantageous use of MR-mediated detection of caspase-3 activity in tumors responsive to chemotherapy.

Accordingly, the disclosure provides embodiments of a novel caspase-3-activatable Gd-based MRI probe for imaging chemotherapy-induced tumor apoptosis in mice. This activatable MRI probe undergoes intramolecular cyclization and subsequent self-assembly into GdNPs upon caspase-3 activation, resulting in enhanced $r_1$ relaxivity (106%) and longer retention in apoptotic tumors. The use of small-size contrast agents to achieve higher $r_1$ relaxivity value (29.3 $mM^{-1}$ $s^{-1}$) upon caspase-3 activation and significant SI enhancement in apoptotic tumor makes this an advantageous strategy for the high-resolution MR monitoring of cancer therapy response.

One aspect of the disclosure, therefore, encompasses embodiments of an activatable probe comprising a detachable capping moiety conjugated to a self-cyclizing molecule comprising a cysteine moiety, a 2-cyano-6-hydroxyquinoline moiety, an amino luciferin scaffold, and a detectable imaging moiety.

In embodiments of this aspect of the disclosure, the detachable capping moiety can be a peptide selectively cleavable from the cysteine by at least one peptidase.

In some embodiments of this aspect of the disclosure, the peptidase can be caspase-3, caspase-7, or both caspase-3 and caspase-7.

In some embodiments of this aspect of the disclosure, the detachable capping moiety has the amino acid sequence L-aspartate-glutamate-valine-aspartate.

In some embodiments of this aspect of the disclosure, the self-cyclizing composition has the formula I:

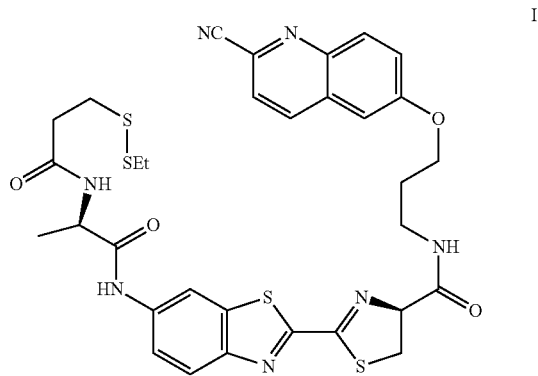

In some embodiments of this aspect of the disclosure, the detectable probe can be an optically detectable label, a detectable by positron electron transmission, or detectable by magnetic resonance imaging (MRI).

In some embodiments of this aspect of the disclosure, the detectable imaging moiety is a fluorophore.

In some embodiments of this aspect of the disclosure, the detectable imaging moiety detectable by positron electron transmission can be selected from the group consisting of: $^{11}C$, $^{13}N$, $^{15}O$, $^{17}F$, $^{18}F$, $^{75}Br$, $^{76}Br$, and $^{124}I$.

In some embodiments of this aspect of the disclosure, the activatable probe can have the formula II, III or IV:

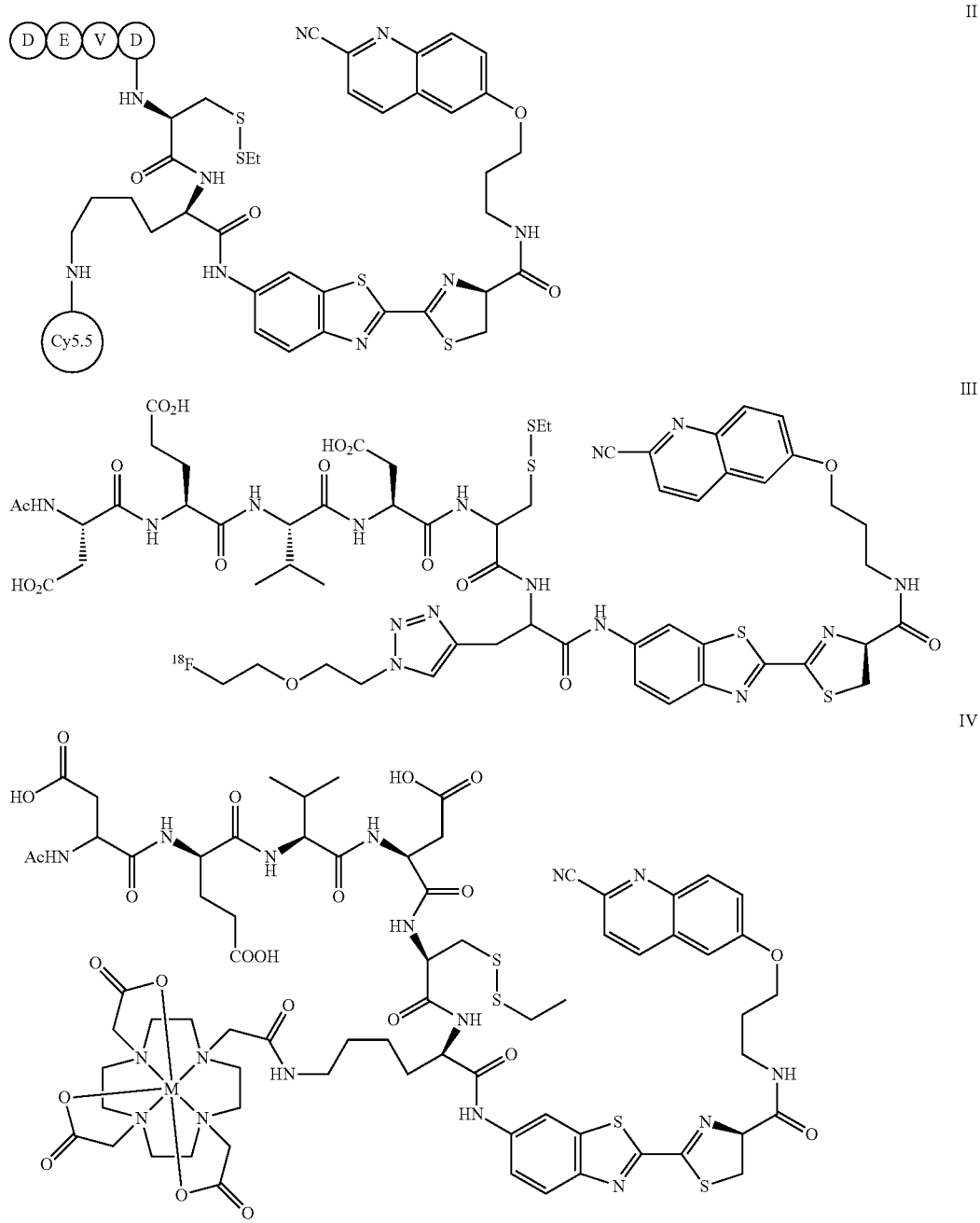

In some embodiments of this aspect of the disclosure, the activatable probe can further comprise a chelating agent and the detectable imaging moiety detectable by magnetic resonance imaging (MRI) can be gadolinium (Gd), thulium (Tm), or europium (Eu), or a combination thereof.

In some embodiments of this aspect of the disclosure, the activatable probe can further comprise a quenching moiety attached to the detachable capping moiety, wherein said quenching moiety is selected to quench the fluorescence from the fluorophore when the detachable capping moiety is conjugated to the self-cyclizing molecule.

In embodiments of this aspect of the disclosure, in formula IV, M can be gadolinium (Gd), thulium (Tm), or europium (Eu), or a combination thereof.

In some embodiments of this aspect of the disclosure, the activatable probe can be admixed with a pharmaceutically acceptable carrier.

Yet another aspect of the disclosure encompasses embodiments of a nano-aggregation probe, wherein said nano-aggregation probe is an aggregate of an activated probe, wherein said activated probe comprises a self-cyclized molecule having the formula V:

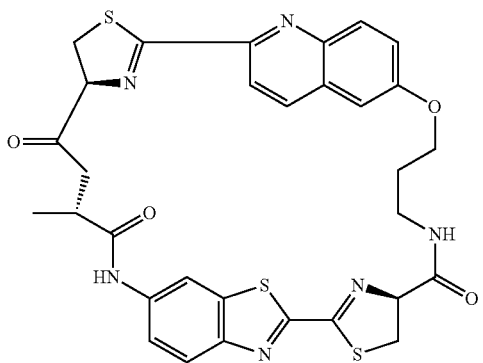

and a detectable imaging moiety attached thereto.

In some embodiments of this aspect of the disclosure, the detectable imaging moiety can be an optically detectable label, detectable by positron electron transmission, or detectable by magnetic resonance imaging (MRI).

Still another aspect of the disclosure encompasses embodiments of a method of forming a nano-aggregation probe comprising delivering to an apoptotic cell a pharmaceutically acceptable composition comprising an activatable probe, wherein said activatable probe can comprise a detachable capping moiety conjugated to a self-cyclizing molecule, said self-cyclizing molecule comprising a cysteine moiety, a 2-cyano-6-hydroxyquinoline moiety, an amino luciferin scaffold, and a detectable imaging moiety, wherein the detachable capping moiety has the amino acid sequence L-aspartate-glutamate-valine-aspartate and is selectively cleavable from the self-cyclizing molecule by caspase 3/7, whereupon the activatable probe can enter the apoptotic cell, an apoptotically-induced caspase 3/7 cleaves the detachable capping moiety from the activatable probe, and said probe aggregates to form the nano-aggregation probe. In some embodiments, the activatable probe can have the formula II, III, or IV:

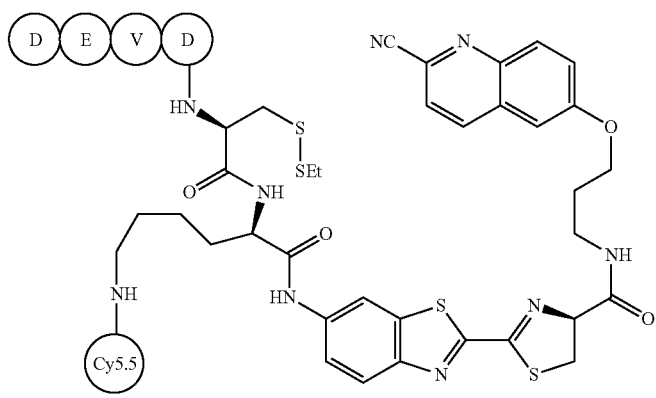

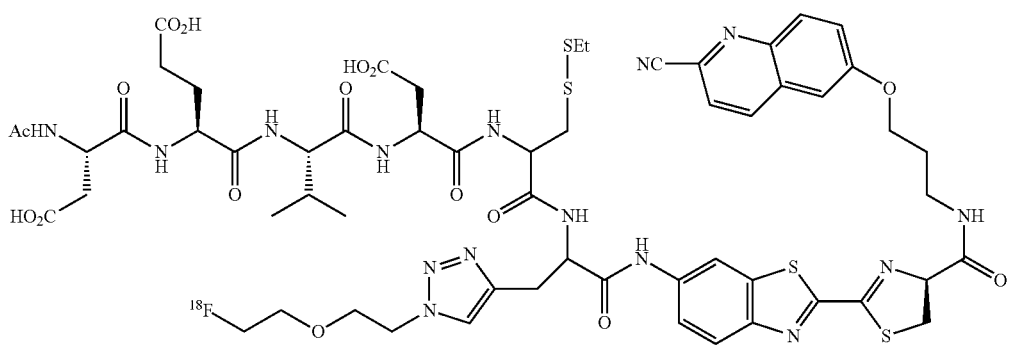

-continued

IV

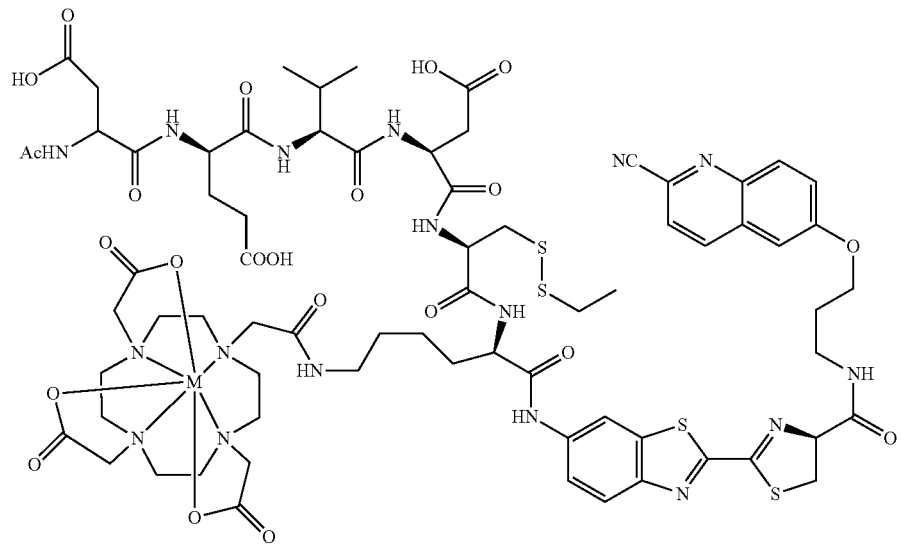

In embodiments of this aspect of the disclosure, in formula IV, M can be, but is not limited to, gadolinium (Gd), thulium (Tm), or europium (Eu), or a combination thereof.

In some embodiments of this aspect of the disclosure, the detectable imaging moiety can be a fluorophore and the activatable probe can further comprise a quenching moiety attached to the detachable capping moiety, wherein said quenching moiety can be selected to quench the fluorescence from the fluorophore when the detachable capping moiety is conjugated to the self-cyclizing molecule.

In some embodiments of this aspect of the disclosure, the pharmaceutically acceptable composition further comprises a pharmaceutically acceptable carrier.

Still yet another aspect of the disclosure encompasses embodiments of a method of detecting an apoptotic cell, the method comprising the steps of: (i) delivering to the cytoplasm of an animal cell a pharmaceutically acceptable composition comprising an activatable probe, wherein said activatable probe comprises a detachable capping moiety conjugated to a self-cyclizing molecule, said self-cyclizing molecule comprising a cysteine moiety, a 2-cyano-6-hydroxyquinoline moiety, an amino luciferin scaffold, and a detectable imaging moiety, wherein the detachable capping moiety has the amino acid sequence L-aspartate-glutamate-valine-aspartate and is selectively cleavable from the self-cyclizing molecule by caspase 3/7, whereupon the activatable probe enters the apoptotic cell, an apotopically-induced caspase 3/7 cleaves the detachable capping moiety from the activatable probe, and said probe aggregates to form a nano-aggregation probe; and (ii) detecting the nano-aggregation probe, thereby determining that the animal cell recipient of the activatable probe is apoptotic.

In some embodiments of this aspect of the disclosure, the detectable imaging moiety is a fluorophore and step (ii) can further comprise irradiating the recipient cell with an incident excitation energy, optically detecting an emitted fluorescence, measuring the intensity of said emission, and optionally generating an image of the fluorescence.

In some embodiments of this aspect of the disclosure, the detectable imaging moiety is detectable by positron electron transmission and step (ii) can further comprise detecting the nano-aggregation probe by PET imaging.

In some embodiments of this aspect of the disclosure, the detectable imaging moiety is detectable by magnetic resonance imaging and step (ii) further comprises detecting the nano-aggregation probe by MRI imaging.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLE

Example 1

Methods

Analytical TLC was performed with 0.25 mm silica gel 60F plates with fluorescent indicator (254 nm). Plates were visualized by ultraviolet light. The ¹H and ¹³C NMR spectra were acquired on a Bruker 400 MHz magnetic resonance spectrometer.

Data for ¹H NMR spectra are reported as follows: chemical shifts are reported as δ in units of parts per million (ppm) relative to chloroform-d (δ 7.26, s); multiplicities are reported as follows: s (singlet), d (doublet), t (triplet), q (quartet), dd (doublet of doublets), m (multiplet), or br (broadened); coupling constants are reported as a J value in Hertz (Hz); the number of protons (n) for a given resonance is indicated nH, and based on the spectral integration values.

MALDI-MS and High Resolution Mass spectrometric analyses were performed on a Dionex HPLC System (Dionex Corporation) equipped with a GP50 gradient pump and an inline diode array UV-Vis detector. A reversed-phase C18 (Phenomenax, 5 μm, 4.6×250 mm, 5 μm, or 21.2×250 mm) column was used in analysis and semi-preparation.

UV absorbance of the probe was recorded on Agilent 8453 UV detector. TEM micrographs were obtained on a JEM 1230 Electron Microscope. Flow cytometry analysis of cells was run on the BD FACScan analyzer. Fluorescent microscopy images were acquired on an Olympus inverted fluorescence microscope (IX2-UCB) equipped with a Nuance multispectral imaging camera. Relaxivity was measured at 1 T (Bruker Icon, Bruker BioSpin Corp.), 1.5 and 3 T (Signa HDx, GE Healthcare). Inductively-coupled plasma mass spectrometry (ICP-MS) analysis was performed on Nu Plasma AttoM high-resolution ICP-MS.

Example 2

Synthesis of C-SNAF (Scheme 1, FIG. 2)

Synthesis of Compound 1

Starting from $NH_2$-CBT, compound 1 was obtained as a white solid according to the methods reported previously (Ye et al., (2011) *Angew. Chem. Int. Ed.* 50: 2275-2279; Liang et al., (2010) *Nat. Chem.* 2: 54-60, incorporated herein by reference in their entireties).

¹H NMR (400 MHz, CDCl₃) δ 9.71 (s, 1H), 8.48 (s, 1H), 7.87 (d, J=9.0 Hz, 1H), 7.64 (d, J=7.5 Hz, 2H), 7.54 (m, 2H), 7.47 (d, J=7.2 Hz, 2H), 7.35-7.23 (m, 8H), 7.22-7.05 (m, 11H), 4.44 (m, 1H), 4.25 (d, J=6.9 Hz, 2H), 4.11-4.01 (m, 1H), 3.84 (m, 3H), 3.01 (m, 2H), 2.52 (m, 2H), 1.87 (s, br, 1H), 1.65 (m, 1H), 1.42 (m, 1H), 1.32 (s, 9H); ¹³C NMR (101 MHz, CDCl₃) δ 171.87, 171.07, 157.30, 155.97, 148.56, 144.40, 144.01, 141.37, 139.00, 136.66, 135.18, 129.59, 128.20, 127.83, 127.18, 127.10, 125.13, 125.02, 121.40, 120.08, 113.20, 111.71, 80.70, 67.25, 66.71, 54.21, 54.12, 49.77, 49.56, 49.34, 49.13, 48.92, 48.70, 48.49, 40.33, 33.74, 31.39, 29.40, 28.70, 28.31, 22.68. MS: calcd. for $C_{56}H_{55}N_6O_6S_2$ [(M+H)⁺]: 971.4. found MALDI-MS: m/z 971.

Synthesis of Compound 3

To a solution of 1 (0.3 mmol), tris(2-carboxyethyl) phosphine hydrochloride (TCEP, 0.3 mmol), and DIPEA (1.8 mmol) in 20 ml $CH_2Cl_2$/MeOH (1/1) under $N_2$ at room temperature was added a solution of 2 (0.33 mmol) in MeOH dropwise, and the mixture was kept stirring at room temperature for a further 30 min. After the reaction was completed, the solvent was removed under vacuum, and the residue was dissolved in ethyl acetate (EA, 30 ml). The solution was washed with water (2×20 ml), brine, and dried with $Na_2SO_4$. After removal of EA, the residue was directly dissolved in 20% TFA/$CH_2Cl_2$, and the mixture was kept stirring at room temperature for another 1 h to completely deprotect the Boc and Trt groups. The solvent was removed, and cold $Et_2O$ (35 ml) was added to precipitate the intermediate. After centrifugation (2500 rpm), the precipitate was dissolved in MeOH, to which was added PySSEt (0.4 mmol), and continued reaction for another 20 min. After the reaction, MeOH was removed, and the residue was precipitated out with cold $Et_2O$ (35 ml), followed by purification with silica gel chromatography with eluent of $CH_2Cl_2$/MeOH (40/1 to 20/1) to afford compound 3 as light yellow foam.

¹H NMR (400 MHz, DMSO-d₆) δ 10.63 (s, 1H), 9.10 (d, J=7.5 Hz, 1H), 8.54 (s, 1H), 8.41 (m, 4H), 8.31 (t, J=5.6 Hz, 1H), 8.06 (d, J=8.9 Hz, 1H), 7.97 (d, J=9.3 Hz, 1H), 7.90 (d, J=8.5 Hz, 1H), 7.84 (d, J=7.5 Hz, 2H), 7.68 (d, J=9.1 Hz, 1H), 7.63 (d, J=7.4 Hz, 2H), 7.53 (dd, J=9.3, 2.6 Hz, 1H), 7.44 (d, J=2.6 Hz, 1H), 7.37 (t, J=7.4 Hz, 2H), 7.28 (m, 3H), 5.32 (t, J=9.3 Hz, 1H), 4.51 (dd, J=13.6, 7.4 Hz, 1H), 4.24 (d, J=6.9 Hz, 2H), 4.21-4.10 (m, 5H), 3.74-3.61 (m, 2H), 3.10-3.24 (m, 2H), 2.97 (m, 3H), 2.75 (q, J=8 Hz, 2H), 2.08-1.96 (m, 2H), 1.70 (m, 3H), 1.41 (m, 3H), 1.25 (t, J=8 Hz, 3H). MS: calcd. for $C_{50}H_{52}N_9O_6S_4$ [(M+H)⁺]: 1002.3. found ESI-MS: m/z 1002.7.

Synthesis of 4

A solution of 3 (0.1 mmol), Ac-Asp(O$^t$Bu)-Glu(O$^t$Bu)-Val-Asp(O$^t$Bu)-COOH (1.05 equiv.), HBTU (1.1 equiv.), and DIPEA (2.0 equiv.) in dry THF (20 ml) was kept stirring at room temperature for 2-3 h. After the reaction was completed, THF was removed. The residue was purified with a short silica gel column with the eluent of $CH_2Cl_2$/MeOH (15/1), which was followed by deprotection of the Fmoc-group with 5% piperidine in DMF at room temperature for 10 min. The reaction was quenched with 1 N HCl, and purified by HPLC to furnish compound 4 after lyophilization (combined yield of 43% for two steps).

¹H NMR (400 MHz, DMSO-d₆) δ 10.42 (s, 1H), 8.60 (dd, J=7.9, 1.8 Hz, 1H), 8.43 (d, J=8.5 Hz, 2H), 8.31 (m, 2H), 8.19 (m, 2H), 8.06 (d, J=8.9 Hz, 1H), 8.01-7.86 (m, 3H), 7.80-7.60 (m, 5H), 7.53 (dd, J=9.3, 2.7 Hz, 1H), 7.45 (d, J=2.1 Hz, 1H), 5.31 (t, J=9.2 Hz, 1H), 4.62-4.47 (m, 3H), 4.42 (s, br, 1H), 4.32 (s, br, 1H), 4.19 (t, J=6.1 Hz, 2H), 4.14-4.02 (m, 1H), 3.84-3.61 (m, 10H), 3.06 (m, 1H), 2.99-2.90 (m, 1H), 2.81-2.73 (m, 2H), 2.69 (m, 2H), 2.59 (dd, J=15.9, 5.3 Hz, 1H), 2.44-2.35 (m, 1H), 2.13 (m, 2H), 2.02 (m, 2H), 1.92-1.79 (m, 5H), 1.67 (s, br, 2H), 1.54 (m, 2H), 1.46-1.26 (m, 29H), 1.21 (t, J=8.0 Hz, 3H), 0.84-0.68 (m, 6H). ¹³C NMR (101 MHz, DMSO-d6) δ 172.44, 171.66, 171.44, 171.29, 171.03, 170.20, 170.06, 169.96, 169.80, 164.89, 159.84, 159.38, 159.14, 158.81 (TFA), 149.33, 144.30, 138.74, 137.20, 136.96, 131.38, 131.00, 130.58, 125.38, 124.87, 124.79, 120.37, 118.60, 112.15, 106.86, 80.92, 80.77, 80.20, 79.96, 66.78, 63.74, 58.27, 54.06, 53.06, 52.46, 50.38, 50.13, 41.27, 39.35, 37.99, 36.71, 35.27, 32.26, 31.90, 31.28, 29.12, 28.31, 27.86, 27.30, 23.15, 23.02, 19.76, 18.72, 14.93. MS: calcd. for $C_{67}H_{94}N_{13}O_{15}S_4$ [(M+H)⁺]: 1448.6. found MALDI-MS: m/z 1449.1.

Synthesis of 5

Compound 4 was deprotected using a solution of TFA/$CH_2Cl_2$/TIPSH (95/2.5/2.5) at room temperature for 3 h. After the solvent was removed, cold $Et_2O$ was added, and the precipitate was dried under vacuum to give compound 5 in 83% yield without further purification.

$^1$H NMR (400 MHz, DMSO-d6) δ 10.37 (s, 1H), 8.59 (d, J=9.7 Hz, 1H), 8.43 (d, J=8.0 Hz, 2H), 8.36-8.13 (m, 4H), 8.12-7.86 (m, 5H), 7.66 (m, 5H), 7.53 (d, J=9.2 Hz, 1H), 7.46 (s, 1H), 5.30 (t, J=9.0 Hz, 1H), 4.66-4.27 (m, 5H), 4.18 (s, br, 2H), 4.13-4.04 (m, 1H), 3.36 (m, 3H), 3.15-3.02 (m, 1H), 2.96 (m, 1H), 2.85-2.64 (m, 5H), 2.56 (m, 2H), 2.44 (m, 1H), 2.16 (m, 2H), 2.09-1.63 (m, 11H), 1.54 (s, br, 2H), 1.37 (m, 2H), 1.21 (t, J=6.9 Hz, 3H), 0.77 (m, 6H); 13C NMR (101 MHz, DMSO) δ 174.81, 172.40, 172.36, 171.82, 171.70, 171.42, 170.31, 169.81, 164.92, 159.87, 159.39, 149.32, 144.30, 138.72, 137.22, 136.99, 131.39, 131.01, 130.58, 125.40, 124.89, 124.81, 120.39, 118.62, 112.18, 106.87, 79.94, 66.76, 58.39, 54.10, 53.19, 52.65, 50.48, 50.29, 39.38, 36.70, 36.64, 36.48, 35.30, 32.28, 31.75, 31.11, 30.73, 29.11, 27.51, 27.30, 23.17, 23.05, 19.76, 18.71, 14.96. MS: calcd. for $C_{55}H_{70}N_{13}O_{15}S_4$ [(M+H)$^+$]: 1280.4. found MALDI-MS: m/z 1280.8.

Synthesis of C-SNAF

To a solution of 5 (4 mg) in dry DMF (0.3 ml) was added Cy5.5-mono NHS ester (1.5 mg) and DIPEA (5 μl), and the mixture was kept stirring at room temperature further for 1 h. After the reaction was completed, the mixture was purified by HPLC to afford C-SNAF in 53% yield. >99% purity after purification. MS: calcd. for $C_{66}H_{112}N_{15}O_{28}S_8$ [(M+H)$^+$]: 2178.6. found MALDI-MS: m/z 2178.7.

Example 3

Scheme S2. Synthesis of L-Ctrl (Scheme 2, FIG. 3A)

Synthesis of 7

A solution of 1 (0.3 mmol), 6 (0.33 mmol), tris(2-carboxyethyl) phosphine hydrochloride (TCEP, 0.3 mmol), and DIPEA (1.8 mmol) in 20 ml CH$_2$Cl$_2$/MeOH (1/1) was stirred at room temperature for 30 min. After the reaction was completed, the solvent was removed under vacuum, and the residue was dissolved in ethyl acetate (EA, 30 ml). The solution was washed with water (2×20 ml), brine, and dried with Na$_2$SO$_4$. After removal of EA, the residue was directly dissolved in 20% TFA/CH$_2$Cl$_2$, and the mixture was kept stirring at room temperature for another 1 h to completely deprotect the Boc and Trt groups. The solvent was removed, and cold Et$_2$O (35 ml) was added to precipitate the intermediate. After centrifugation (2500 rpm), the precipitate was dissolved in MeOH, to which was added PySSEt (0.4 mmol), and continued reaction for another 20 min. After the reaction, MeOH was removed, and the residue was precipitated out with cold Et$_2$O (35 ml), followed by purified with silica gel chromatography with eluent of CH$_2$Cl$_2$/MeOH (30/1 to 15/1) to afford compound 7 as light yellow foam.

$^1$H NMR (400 MHz, DMSO-d6) δ 10.64 (s, 1H), 9.13 (d, J=7.3 Hz, 1H), 8.94 (d, J=4.3 Hz, 1H), 8.63 (d, J=8.3 Hz, 1H), 8.54 (s, 1H), 8.44 (s, br, 2H), 8.34 (t, J=5.5 Hz, 1H), 8.06 (dd, J=9.0, 2.3 Hz, 2H), 7.83 (d, J=7.5 Hz, 2H), 7.75 (m, 1H), 7.62 (m, 4H), 7.53 (d, J=2.5 Hz, 1H), 7.36 (t, J=7.4 Hz, 2H), 7.28 (m 3H), 5.33 (t, J=9.2 Hz, 1H), 4.51 (m, 1H), 4.31-4.07 (m, 6H), 3.79-3.60 (m, 2H), 3.18 (m, 2H), 2.98 (m, 2H), 2.74 (m, 2H), 2.13-1.95 (m, 2H), 1.75 (m, 2H), 1.54-1.24 (m, 6H), 1.24 (t, J=7.2 Hz, 3H); $^{13}$C NMR (101 MHz, DMSO) δ 171.30, 169.80, 167.60, 164.92, 159.88, 159.52, 159.19 (TFA), 158.29, 156.76, 149.38, 145.20, 144.55, 141.37, 141.03, 138.71, 138.46, 136.95, 130.47, 128.23, 127.67, 126.34, 125.92, 125.76, 124.91, 122.69, 120.76, 120.41, 112.24, 107.49, 79.96, 66.73, 65.87, 54.63, 51.86, 47.41, 39.54, 36.72, 35.30, 32.34, 31.93, 29.74, 29.14, 23.34, 14.76. MS: calcd. for $C_{49}H_{53}N_8O_6S_4$ [(M+H)$^+$]: 977.3. found ESI-MS: m/z 978.1.

Synthesis of 8

A solution of 7 (0.1 mmol), Ac-Asp(O$^t$Bu)-Glu(O$^t$Bu)-Val-Asp(O$^t$Bu)-COOH (1.05 equiv.), HBTU (1.1 equiv.), and DIPEA (2.0 equiv.) in dry THF (20 ml) was kept stirring at room temperature for 2-3 h. After the reaction was completed, THF was removed. The residue was purified with a short silica gel column with the eluent of CH$_2$Cl$_2$/MeOH (15/1), which was followed by deprotection of the Fmoc-group with 5% piperidine in DMF at room temperature for 10 min. The reaction was quenched with 1 N HCl, and purified by HPLC to furnish compound 8 after lyophilization (51% yield in two steps).

$^1$H NMR (400 MHz, DMSO-d6) δ 10.43 (s, 1H), 8.90 (d, J=4.7 Hz, 1H), 8.64-8.52 (m, 2H), 8.46 (m, 1H), 8.31 (m, 2H), 8.21 (m, 2H), 8.10-7.91 (m, 3H), 7.89-7.62 (m, 6H), 7.56 (dd, J=9.2, 2.5 Hz, 1H), 7.51 (d, J=2.3 Hz, 1H), 5.31 (t, J=9.2 Hz, 1H), 4.54 (m, 3H), 4.42 (s, br, 1H), 4.34 (m, 1H), 4.17 (t, J=6.1 Hz, 2H), 4.13-4.06 (m, 1H), 3.78-3.58 (m, 2H), 3.47 (t, J=5.3 Hz, 1H), 3.15-3.03 (m, 1H), 2.95 (m, 1H), 2.84-2.64 (m, 5H), 2.60 (dd, J=15.8, 5.1 Hz, 1H), 2.48-2.35 (m, 2H), 2.24-2.08 (m, 2H), 2.02 (m, 2H), 1.95-1.76 (m, 6H), 1.70 (s, br, 2H), 1.55 (m, 2H), 1.50-1.26 (m, 30H), 1.25-1.17 (m, 3H), 0.75 (m, 6H); $^{13}$C NMR (101 MHz, DMSO) δ 172.44, 171.67, 171.46, 171.30, 171.04, 170.23, 170.08, 169.96, 169.81, 164.89, 159.82, 159.77, 159.44, 159.10, 158.76 (TFA), 158.11, 149.32, 145.79, 140.09, 139.48, 138.76, 136.96, 130.35, 127.15, 125.41, 124.86, 122.63, 120.38, 118.59, 115.66, 112.16, 107.45, 80.98, 80.91, 80.80, 80.76, 80.18, 79.96, 72.95, 66.69, 60.93, 58.31, 54.10, 53.09, 52.49, 50.41, 50.25, 50.17, 41.29, 39.33, 37.99, 37.88, 36.73, 35.28, 32.27, 31.91, 31.80, 31.27, 29.17, 28.33, 28.30, 27.85, 27.29, 23.13, 23.04, 19.76, 18.72, 14.91. MS: calcd. for $C_{66}H_{95}N_{12}O_{15}S_4$ [(M+H)$^+$]: 1423.6. found MALDI-MS: m/z 1424.2.

Synthesis of 9

Compound 8 was deprotected using a solution of TFA/CH$_2$Cl$_2$/TIPSH (95/2.5/2.5) at room temperature for 3 h. After the solvent was removed, cold Et$_2$O was added. The precipitate was dissolved in MeOH, to which was added TCEP (1.1 equiv.), and the solution stirred at room temperature for 10 min. NaHCO$_3$ was added into the solution to adjust the pH value to 7, then the free thiol group was methylated with MeI (5 equiv.) at room temperature. for 2 h. The mixture was purified by HPLC to afford compound 9 (72% yield in two steps).

$^1$H NMR (400 MHz, DMSO-d$_6$) $^1$H NMR (400 MHz, DMSO) δ 10.41 (s, 1H), 8.89 (d, J=4.7 Hz, 1H), 8.63-8.52 (m, 2H), 8.48 (d, J=7.5 Hz, 1H), 8.32 (m, 2H), 8.21 (d, J=7.5 Hz, 1H), 8.07 (d, J=8.9 Hz, 1H), 7.99 (m, 2H), 7.80-7.61 (m, 5H), 7.60-7.47 (m, 2H), 5.31 (t, J=9.1 Hz, 1H), 4.63-4.47 (m, 5H), 4.42 (m, 1H), 4.28 (m, 1H), 4.17 (t, J=5.9 Hz, 2H), 4.12-4.06 (m, 1H), 3.68 (m, 2H), 2.82-2.72 (m, 3H), 2.72-2.50 (m, 3H), 2.46-2.40 (m, 1H), 2.18 (m, 2H), 2.11-1.96 (m, 4H), 1.90 (m, 2H), 1.84-1.61 (m, 5H), 1.53 (m, 2H), 1.38 (m, 2H), 0.76 (m, 6H).

Synthesis of L-Ctrl

To a solution of 9 (4 mg) in dry DMF (0.3 ml) was added Cy5.5-mono NHS ester (1.5 mg) and DIPEA (5 μl), and the mixture was kept stirring at room temperature further for 1 h. After the reaction was completed, the mixture was purified by HPLC to afford L-ctrl in 51% yield. >99% HPLC purity. MS: calcd. For $C_{94}H_{110}N_{14}O_{28}S_7$ [(M+H)$^+$]: 2107.6. found MALDI-MS: 2108.5.

Example 4

Scheme 3, FIG. 4

Synthesis of D-Ctrl

Synthesis of 10

Starting from compound 7, 10 was synthesized according to the methods as described for compound 9 with replacement of Ac-Asp(O$^t$Bu)-Glu(O$^t$Bu)-Val-Asp(O$^t$Bu)-COOH with Ac-D-Asp(O$^t$Bu)-D-Glu(O$^t$Bu)-D-Val-D-Asp(O$^t$Bu)-COOH.

$^1$H NMR (400 MHz, DMSO-d$_6$) δ 10.23 (s, 1H), 8.86 (d, J=4.3 Hz, 1H), 8.64-8.53 (m, 2H), 8.48 (m, 1H), 8.36 (d, J=6.3 Hz, 1H), 8.29 (s, br, 1H), 8.22 (d, J=7.7 Hz, 1H), 8.13-7.91 (m, 4H), 7.66 (m, 5H), 7.58-7.43 (m, 2H), 5.31 (t, J=9.2 Hz, 1H), 4.59-4.48 (m, 2H), 4.46-4.36 (m, 2H), 4.26 (m, 1H), 4.19-4.11 (m, 4H), 3.68 (m, 2H), 3.28 (m, 1H), 2.82-2.55 (m, 6H), 2.47-2.40 (m, 1H), 2.20 (m, 2H), 2.07 (s, 3H), 2.03-1.89 (m, 3H), 1.81 (s, 3H), 1.75-1.63 (m, 2H), 1.53 (d, J=6.5 Hz, 2H), 1.36 (s, 2H), 0.79 (m, 6H). MS: calcd. for $C_{63}H_{69}N_{12}O_{15}S_3$ [(M+H)$^+$]: 1209.4. found MALDI-MS: m/z 1209.8.

Synthesis of D-Ctrl

To a solution of 10 (3 mg) in dry DMF (0.3 ml) was added Cy5.5-mono NHS ester (1.1 mg) and DIPEA (5 μl), and the mixture was kept stirring at room temperature for further 1 h. After the reaction was completed, the mixture was purified by HPLC to afford D-ctrl in 47% yield (>99% HPLC purity after purification). MS: calcd. For $C_{94}H_{110}N_{14}O_{28}S_7$ [M$^+$]: 2106.6. found MALDI-MS: 2106.2.

Example 5

Synthesis of High-Resolution Imaging Probe SIM-1 and Control Probe SIM-Ctrl (Scheme 4, FIG. 5)

Synthesis of Compound 11

Compound 1 was dissolved in 5% piperidine/DMF to completely remove Fmoc group. The reaction was then quenched with 1N HCl, and purified by HPLC to afford compound 11 as a white powder after lyophilization.

$^1$H NMR (400 MHz, CD$_3$OD) δ 8.60 (s, 1H), 7.99 (d, J=9.0 Hz, 1H), 7.77 (d, J=8.9 Hz, 1H), 7.34 (m, 6H), 7.26 (m, 6H), 7.20 (m, 3H), 4.55 (dd, J=9.6, 4.3 Hz, 1H), 3.96 (t, J=6.8 Hz, 1H), 2.88-2.76 (m, 2H), 2.54 (m, 2H), 2.05 (s, br, 1H), 1.83-1.24 (m, 14H); $^{13}$C NMR (101 MHz, DMSO-d$_6$) δ 171.57, 171.18, 159.52, 159.18, 155.79, 148.43, 144.93, 139.83, 137.28, 135.77, 129.65, 128.71, 127.44, 125.40, 121.63, 118.63, 115.70, 114.19, 112.21, 79.26, 66.61, 54.16, 54.02, 34.44, 31.74, 28.73, 27.29, 23.00. MS: calcd. for $C_{41}H_{45}N_6O_4S_2$ [(M+H)$^+$]: 749.3. found LC-MS: m/z 749.7.

Synthesis of Compound 12

To a solution of 11 (0.1 mmol) from last step, tris(2-carboxyethyl) phosphine hydrochloride (TCEP, 0.1 mmol), and DIPEA (0.6 mmol) in 15 ml CH$_2$Cl$_2$/MeOH (1/1) under N$_2$ at room temperature was added a solution of 2 (0.12 mmol) in MeOH dropwise, and the mixture was kept stirring at room temperature for further 30 min. After the reaction was completed, the solvent was removed under vacuum, and the residue was purified by HPLC to afford compound 12 as a light yellow powder after lyophilization.

$^1$H NMR (400 MHz, DMSO-d$_6$) δ 10.20 (s, 1H), 8.53 (s, 1H), 8.42 (d, J=8.6 Hz, 1H), 8.31 (m, 2H), 8.06 (d, J=9.0 Hz, 1H), 7.98 (d, J=9.2 Hz, 1H), 7.91 (d, J=8.5 Hz, 1H), 7.78 (s, br, 3H), 7.66 (d, J=8.8 Hz, 1H), 7.53 (dd, J=9.3, 2.7 Hz, 1H), 7.45 (d, J=2.7 Hz, 1H), 7.35-7.24 (m, 15H), 7.13 (d, J=7.3 Hz, 1H), 5.31 (t, J=9.2 Hz, 1H), 4.38 (m, 1H), 4.18 (t, J=6.1 Hz, 4H), 4.01 (m, 1H), 3.76-3.62 (m, 2H), 2.69 (m, 2H), 2.32 (d, J=6.8 Hz, 2H), 2.09-1.94 (m, 2H), 1.80 (s, 1H), 1.67-1.49 (m, 3H), 1.29 (m, 11H); $^{13}$C NMR (101 MHz, DMSO-d$_6$) δ 171.29, 171.18, 169.75, 164.88, 159.91, 159.38, 155.84, 144.91, 144.30, 137.19, 136.89, 131.38, 131.00, 130.58, 129.74, 129.62, 128.94, 128.75, 127.47, 125.40, 124.87, 124.81, 118.62, 112.30, 106.86, 79.95, 79.30, 66.76, 66.61, 54.19, 53.90, 39.28, 36.70, 35.27, 34.27, 31.71, 29.09, 28.74, 27.33, 23.00. MS: calcd. for $C_{57}H_{60}N_9O_6S_3$ [(M+H)$^+$]: 1062.4. found ESI-MS: m/z 1062.5.

Synthesis of Compound SIM-1

To a solution of 12 (3 mg) in dry DMF was added ALEXA FLUOR® 488 5-TFP ester (1 mg) and DIPEA (2 μL), and the mixture was kept stirring at room temperature for 2 h. After the reaction, cold Et$_2$O was added to precipitate the product, which was directly dissolved in a solution of TFA/TIPSH/DCM (25%/72.5%/2.5%) for 1 h. The solvent was removed, and the residue was precipitated with cold Et$_2$O, following by reaction with PySSEt in MeOH to afford SIM-1 after purification by HPLC (52% yield from ALEXA FLUOR® 488 5-TFP ester). MS: calcd. for $C_{56}H_{53}N_{11}O_{14}S_6$ [M$^+$]: 1295.2. found MALDI-MS: m/z 1295.7.

Synthesis of Compound SIM-Ctrl

SIM-1 from last step was dissolved in a solution of CH$_3$CN/H$_2$O (1/1), to which was added TCEP and MeI. The pH value of the reaction solution was adjusted to 6 with NaHCO$_3$, and the reaction was kept stirring at room temperature for another 2 h, following by purification with HPLC to produce SIM-ctrl (83% yield). MS: calcd. for $C_{55}H_{51}KN_{11}O_{14}S_5$ [(M+K$^+$)]: 1288.2. found MALDI-MS: m/z 1289.2.

Example 6

Synthesis of Probe C-SNAF-SIM (Scheme 5, FIG. 5)

To a solution of 5 (3 mg) in dry DMF was added Alexa Fluor 488 5-TFP ester (1 mg) and DIPEA (2 μL), and the mixture was kept stirring at room temperature for 2 h. After the reaction was completed, the mixture was purified by HPLC to afford C-SNAF-SIM in 42% yield based on Alexa Fluor 488 5-TFP ester. MS: calcd. For $C_{78}H_{80}N_{15}NaO_{25}S_6$ [M+Na]$^+$:1817.4. found MALDI-MS: 1817.2.

Example 7

In Vitro HPLC Assay of Enzymatic Reaction

Caspase (human, recombinant from E. coli) assays were performed for caspase-3 (4.9×10$^{-3}$ U; 7.35×10$^{-4}$ mg, Sigma), -7 (18.3 U; 7.35×10$^{-4}$ mg, Calbiochem), and -9 (0.3 U; 7.35×10$^{-4}$ mg, Calbiochem). All caspase assays were conducted in caspase buffer with 50 mM HEPES, 100 mM NaCl, 1 mM EDTA, 10 mM TCEP, 10% glycerol, and 0.1% CHAPS at pH 7.4. Cathepsin B (human liver; 0.27 U; 7.35×10$^{-4}$ mg, Calbiochem) and Legumain (human, recombinant from mouse myeloma cell line; >250 pmol/min/μg; 7.35×10$^{-4}$ mg, R&D Systems) were conducted in reaction buffer with 50 mM sodium acetate, 50 mM NaCl, 0.5 mM EDTA and 10 mM TCEP at pH 5.5. C-SNAF was diluted in the respective enzyme reaction buffer (25 μM, 1 mL) and remained at room temperature for 10 min, to which was then added the respective enzymes. Reactions were performed at 37° C., and monitored by HPLC hourly. The percentage conversion of the reaction was calculated based on the percentage of peak area of C-SNAF-cycl in the HPLC trace at 675 nm UV detection, which indicated the efficacy of enzyme cleavage of C-SNAF.

Example 8

Cell Staining and Epifluorescence Microscopy Imaging

HeLa (or MDA-MB-231) cells in #1.5 borosilicate 8-well chambered coverslips (Nunc) with 70% confluence were either non-treated or treated with 2 μM STS for 4 h. After removal of the medium, the cells were incubated with C-SNAF, L-ctrl, or D-ctrl at 2 μM for 24 h. Some cells were first incubated with caspase inhibitor (Z-VAD-fmk, 50 μM) for 30 min, followed by incubating with 2 μM C-SNAF for 24 h. The cells were carefully washed with PBS (1×) three times, and stained with Hoechst 33342 (2 μM) at 37° C. for 30 min. After rinses with PBS (1×) several times, the medium was replaced and the fluorescence images were acquired with DAPI and Cy5.5 filters. The images were processed using the standard CRi Nuance software, analyzed using Image J software package (NIH), and presented at the same intensity scale for comparison.

Example 9

Super-Resolution Imaging of Self-Assembling Products in Cells Using 3D-SIM

HeLa cells on micro cover glass slides (22×22 mm) were either untreated or treated with STS (2 μM) for 4 h, following by incubation with C-SNAF-SIM (2 μM) for 24 h.

After removal of the medium, cells were carefully washed with PBS (1×) three times, fixed with 2% paraformaldehyde (PFA) at 37° C. for 10 min, washed with PBS a further three times and then permeabilized with 0.1% Triton X-100 at 37° C. for 10 min. After three further washes with PBS, the glass slides were mounted with mounting medium (with DAPI). The super-resolution images were acquired by 3D-SIM using a DeltaVision OMX imaging system (Applied Precision) with simultaneous excitation at 408 nm for DAPI and 488 nm for Alexa 488, according to the standard procedure in the manufacturer instructions. The structured illumination images were analyzed with an API DeltaVision OMX soft-WoRx image processing software and the size of self-assembling particles was analyzed using Image J software package.

Example 10

Chemotherapy Mouse Model

To establish tumors in 6-week-old female nu/nu mice, 2×10$^6$ HeLa cells suspended in 50 μL of a 50% v/v mixture of Matrigel in supplemented DMEM (10% FBS, 1% pen-strep) were injected subcutaneously in the shoulders of the mouse. Tumors were grown until a single aspect was 0.7 to 0.9 cm (approximately 10-15 days), and then treatment consisting of 8 mg/kg DOX or saline was initiated. Treatments were administered intravenously once every 4 d for a total of three times. Total mouse body weight and tumor size (width and length by caliper) was measured every other day. Tumor volumes were calculated assuming ellipsoid shape with the formula $(l \times w^2)/2$.

Example 11

In Vivo Fluorescence Imaging

Two days following the final treatment, 5 nmol probe in saline was injected intravenously and fluorescence imaging began immediately on a Maestro hyperspectral fluorescent imaging system (PerkinElmer, Mass., USA) using a 635±25 nm excitation filter and a 675 nm long-pass emission filter, with images acquired from 670 to 900 nm. Tissue autofluorescence and Cy5.5 fluorescence were deconvolved, and tumor fluorescence intensity was quantified by region of interest measurement using Nuance v.3.0.1.2 software (Perkin Elmer, Mass., USA).

Example 12

Synthesis of the Compound 4

To a solution of N-Boc-propargylglycine (384 mg, 1.8 mmol) in THF (3 mL) was added to 4-methylmorpholine (330 mL, 3.0 mmol) and isobutyl chloroformate (195 mL, 1.5 mmol) at 0° C. The resulting mixture was stirred for 2 h at 0° C. 6-amino-2-cyanobenzothiazole (175 mg, 1.0 mmol) in THF (5 mL) was added to the reaction mixture at 0° C. The resulting solution was stirred for 12 h at room temperature. The reaction was quenched by adding aqueous 1 M HCl (3 mL). The resulting solution was partitioned with EtOAc (40 mL) and H$_2$O (40 mL) and the organic phase was washed with water and aqueous NaHCO$_3$ (40 mL). The combined organic phase was dried with MgSO$_4$, filtered and evaporated under reduced pressure. The crude product was purified with silica gel chromatography (Hexane: EtOAc=1: 1) to give the product compound 4 (296 mg, 85%).
$^1$H-NMR (CDCl, 400 MHz) δ 9.45 (s, 1H), 8.44 (s, 1H), 7.85 (d, 1H, J=8.4), 7.27 (d, 1H, J=8.4), 5.82 (d, 1H, J=7.6), 4.57 (m, 1H), 2.75 (m, 2H), 2.11 (t, 1H, J=2.4), 1.45 (s, 9H); $^{13}$C-NMR (CDCl$_3$, 100 MHz) δ 170.1, 156.6, 148.5, 138.5, 136.6, 135.3, 125.2, 120.8, 113.2, 111.4, 81.6, 78.8, 72.5, 54.1, 28.6, 22.4; ESI-MS calcd for C$_{18}$H$_{19}$N$_4$O$_3$S+ ([M+H]+) 371.43. found 371.20.

Example 13

Synthesis of the Dipeptide 5

To a solution of the compound 4 (300 mg, 0.81 mmol) in DCM (3 mL) was added anhydrous TFA (3 mL) at room temperature. The resulting solution was stirred for 1 h and then the solvent was evaporated under reduced pressure. The remaining TFA in crude product was removed under vacuum. Dried crude product was dissolved in DMF (5 mL) and N-Boc-S-Trt-D-cysteine (394 mg, 0.85 mmol), HBTU (323 mg, 0.85 mmol) and DIPEA (442 mL, 2.5 mmol) was added at room temperature. The resulting solution was stirred for 1 h and diluted with EtOAc (30 mL). The resulting organic solution was washed with water (40 mL) and brine (40 mL×2). The combined organic phase was dried with MgSO$_4$, filtered and evaporated under reduced pressure. The crude product was purified with silica gel chromatography (Hexane: EtOAc=1:1) to give the dipeptide 5 (464 mg, 80%).

$^1$H-NMR (CDCl, 400 MHz) δ 9.12 (s, 1H), 8.66 (s, 1H), 8.00 (d, 1H, J=8.8), 7.71 (d, 1H, J=8.8), 7.42 (d, 6H, J=7.2), 7.23-7.34 (m, 9H), 6.57 (d, 1H, J=8.4), 5.02 (d, $^1$H, J=5.2), 4.70 (m, 1H), 3.23 (m, 1H), 3.02-3.08 (m, 1H), 2.93 (dd, 1H, J=13.2, 8.4), 2.62-2.69 (m, 2H), 2.02 (t, 1H, J=2.4), 1.40 (s, 9H); $^{13}$C-NMR (CDCl, 100 MHz) δ 171.5 168.6, 156.1, 149.0, 144.3, 138.6, 136.8, 135.5, 129.7, 128.5, 127.4, 125.2, 121.6, 113.3, 112.0, 81.4, 78.9, 72.5, 67.8, 54.9, 52.2, 33.3, 28.5, 21.4; ESI-MS calcd for C40H37N5NaO4S2 ([M+Na]$^+$) 738.22. found 738.19.

Example 14

Synthesis of the Compound 7a

To a solution of the compound 5 (143 mg, 0.2 mmol) in DMF (5 mL) was added the quinolone 6a 1 (89 mg, 0.2 mmol), TCEP.HCl (115 mg, 0.4 mmol) and DIPEA (418 mL, 2.4 mmol). The resulting solution was stirred for 30 min and then the solvent was evaporated under reduced pressure. To remove both N-Boc and S-Trt group, the crude product was dissolved in DCM:TFA:TIPS (1:1:0.05) mixture and the resulting solution was stirred at room temperature. After 1 h, the solvent was evaporated under reduced pressure and the remaining TFA was further removed under vacuum. The dried product was re-dissolved in MeOH (5 mL) and 2-(ethyldisulfanyl)pyridine (68 mg, 0.4 mmol) was added. The resulting solution was stirred for 2 h at room temperature. The crude product was purified with preparative HPLC to give the desired product 7a (88 mg, 51% from 5).

$^1$H-NMR (CD OD, 400 MHz) δ 8.30 (d, 1H, J=2.0), 8.12 (d, 1H, J=8.8), 7.86 (d, 1H, J=8.8), 7.78 (d, 1H, J=9.2), 7.61 (d, 1H, J=8.8), 7.51 (dd, 1H, J=9.2, 2.4), 7.39 (dd, 1H, J=9.2, 2.4), 7.15 (d, 1H, J=2.4), 5.30 (t, 1H, J=9.2), 4.77 (t, 1H, J=7.2), 4.32 (dd, 1H, J=8.8, 4.8), 4.12-4.18 (m, 2H), 3.68-3.78 (m, 2H), 3.64 (m, 1H), 3.48 (m, 1H), 3.35 (dd, 1H, J=14.4, 4.8), 3.09 (dd, 1H, J=14.4, 8.8), 2.76-2.93 (m, 4H), 2.52 (t, 1H, J=2.4), 2.04-2.18 (m, 2H), 1.37 (t, 1H, J=7.6); $^{13}$C-NMR (CD OD, 100 MHz) δ 172.7, 170.4, 168.8, 167.2, 160.9, 160.5, 150.6, 145.2, 138.9, 137.9, 137.5, 131.8, 131.6, 131.4, 126.0, 125.3, 125.0, 121.0, 118.9, 113.0, 106.9, 80.6, 79.9, 73.1, 67.5, 54.7, 53.3, 39.8, 37.9, 35.9, 32.9, 29.3, 22.9, 14.6; MALDI-TOF calcd. for C$_{34}$H$_{34}$N$_8$NaO$_4$S$_4^+$ ([M+Na]$^+$) 769.934. found 770.139.

Example 15

Synthesis of the Compound 7b

To a solution of the compound 5 (72 mg, 0.1 mmol) in DMF (3 mL) was added the quinolone 6b 1 (42 mg, 0.1 mmol), TCEP.HCl (58 mg, 0.2 mmol) and DIPEA (209 mL, 1.2 mmol). The resulting solution was stirred for 30 min and then the solvent was evaporated under reduced pressure. The crude product was dissolved in DCM:TFA:TIPS (1:1:0.05) solution to remove both N-Boc and S-Trt group, and then the resulting solution was stirred at room temperature. After 1 h, the solvent was evaporated under reduced pressure and the remaining TFA was removed under vacuum. The dried product was re-dissolved in MeOH (3 mL) and 2-(ethyldisulfanyl)pyridine (34 mg, 0.2 mmol) was added. The resulting solution was stirred for 1 h at room temperature. The crude product was purified with preparative HPLC to give the desired product 7b (33 mg, 40% from 5).

$^1$H-NMR (CD OD, 400 MHz) δ 8.87 (dd, 1H, J=5.6, 1.6), 8.75 (d, 1H, J=8.8), 8.23 (d, 1H, J=1.6), 7.99 (d, 1H, J=8.8), 7.82-7.87 (m, 2H), 7.64 (dd, 1H, J=9.2, 2.8), 7.55 (dd, 1H, J=8.8, 2.0), 5.33 (t, 1H, J=9.2), 4.73 (t, 1H, J=7.6), 4.35 (dd, 1H, J=8.4, 4.8), 4.12-4.25 (m, 2H), 3.74 (d, 2H, J=9.2), 3.65 (m, 1H), 3.47 (m, 1H), 3.35 (dd, 1H, J=14.4, 4.8), 3.12 (dd, 1H, J=14.4, 8.0), 2.76-2.88 (m, 4H), 2.54 (t, 1H, J=2.4), 2.06-2.22 (m, 2H), 1.36 (t, 1H, J=7.2); MALDI-TOF calcd for C$_{33}$H$_{36}$N$_7$O$_4$S$_4^+$ ([M+H]$^+$) 722.943. found 722.770.

Example 16

Synthesis of Ac-Asp(tBu)-Glu(tBu)-Val-Asp(tBu)-OH (Ac-DEVD-OH, 8a)

The protected caspase-3 substrate (Ac-DEVD-OH) was prepared by solid phase peptide synthesis. MALDI-TOF calcd. for C$_{32}$H$_{54}$N$_4$NaO$_{12}$ ([M+Na]$^+$) 709.364. found 709.007.

Example 17

Synthesis of Ac-Asp(tBu)-Glu(tBu)-Val-Asp(tBu)-OH (Ac-devd-OH, 8b)

The peptide 8b (Ac-devd-OH), control peptide probe, was prepared by using D-amino acids. MALDI-TOF calcd. for C$_{32}$H$_{54}$N$_4$NaO$_{12}$ ([M+Na]$^+$) 709.364. found 709.213.

Example 18

Synthesis of the Activatable Probe 3a

To a solution of 7a (15 mg, 17.4 mmol) in THF (2 mL) was added 8a (18 mg, 26.1 mmol), HBTU (10 mg, 26.4 mmol) and DIPEA (16 mL, 87 mmol). The resulting solution was stirred for 1 h at room temperature and then it was diluted with EtOAc (30 mL). The resulting organic solution was washed with brine (30 mL×2). The combined organic phase was dried with MgSO$_4$, filtered and evaporated under reduced pressure. To remove t-Bu groups, the resulting product was dissolved in DCM:TFA:TIPS (1.0:1.0:0.05) solution. After 1 h, the solvent was evaporated under reduced pressure and the crude product was purified with preparative HPLC to give the probe 3a (15 mg, 12.0 mmol, 69% from 7a). MALDI-TOF calcd. for C$_{54}$H$_{63}$N$_{12}$O$_{15}$S$_4$ ([M+H]$^+$) 1248.409. found 1248.735.

Example 19

Synthesis of the Control Probe 3b

To a solution of 7b (13 mg, 15.6 mmol) in THF (1.5 mL) was added to 8b (22 mg, 31.2 mmol), HBTU (12 mg, 31.2 mmol) and DIPEA (13.5 mL, 78 mmol). The resulting solution was stirred for 1 h at room temperature. After the reaction was completed, the solvent was evaporated under reduced pressure. The crude product was purified with preparative HPLC to give 11 mg (7.9 mmol) of protected product. MALDI-TOF calcd for C$_{65}$H$_{88}$N$_{11}$O$_{15}$S$_4$ ([M+H]+) 1391.718. found 1392.723.

The purified product (11 mg, 7.9 mmol) was dissolved in DMF (1 mL) and then TCEP.HCl (4.5 mg, 16 mmol), DIPEA (20 mL, 0.1 mmol) and methyl iodide (1.9 mL, 30 mmol) was added at room temperature. The resulting solution was stirred for 40 min and then the solvent was evaporated under reduced pressure. To remove t-Bu groups, the resulting product was dissolved in DCM:TFA:TIPS (1.0:1.0:0.05) solution. After 1 h, the solvent was evaporated under reduced pressure and the crude product was purified with preparative HPLC to give the control probe 3b (7 mg, 6.0 mmol, 38% from 7b). MALDI-TOF calcd. for $C_{52}H_{62}N_{11}O_{15}S_3$ ([M+H]+) 1176.358. found 1176.431.

Example 20

2-(2-(2-(2-azidoethoxy)ethoxy)ethoxy)ethyl 4-methylbenzenesulfonate (9)

$^1$H-NMR (CDCl, 400 MHz) δ 7.80 (d, 2H, J=8.4), 7.34 (d, 2H, J=8.4), 4.16 (t, 2H, J=4.8), 3.55-3.71 (m, 12H), 3.38 (t, 2H, J=5.2), 2.45 (s, 3H); $^{13}$C-NMR (CDCl, 100 MHz) δ 145.0, 133.2, 130.1, 128.2, 71.0, 70.9, 70.8, 70.3, 69.5, 68.9, 50.9, 21.9; ESI-MS calcd. for $C_{15}H_{24}N_3O_6S^+$ ([M+H]$^+$) 374.14. found 374.18.

Example 21

Cell Culture

HeLa human cervical adenocarcinoma epithelial cells and MDA-MB-231 human breast adenocarcinoma epithelial cells from the ATCC were cultured in Dulbecco's modified eagle medium (GIBCO) supplemented with 10% fetal bovine serum (FBS, GIBCO), 100 U mL$^{-1}$ penicillin and 100 μg mL$^{-1}$ streptomycin (GIBCO). For CASPASE-GLO® 3/7 assays, HeLa and MDA-MB-231 cells were plated onto 96-well plates (Costar) and allowed to reach approximately 70% confluence. For epifluorescence microscopy experiments, cells were plated onto #1.5 borosilicate 8-well chambered coverslips (Nunc) and grown to approximately 70% confluence. For flow cytometry experiments, HeLa cells were plated onto 12-well clear plates and grown to approximately 70% confluence. For super-resolution microscopy experiments, HeLa cells were plated on micro cover glass (20×20 mm) and grown to approximately 70% confluence.

Example 22

CASPASE-GLO® 3/7 Assays to Measure the Caspase-3/7 Activity in Drug-Induced Apoptotic Cells HeLa cells (approximately 4×10$^6$) were seeded onto cell culture dish. After cell growth to about 70% confluence, medium was removed and 8 ml of fresh medium containing a different concentration of STS (0, or 2 μM) was added to the dishes and incubated for 4 h (STS). Then, the medium was replaced with 8 ml of fresh medium with further incubation for 24 h. The medium was removed, trypsinized, centrifuged (1200 rpm), and washed with PBS twice. The obtained cell pellets were lysed with RIPA buffer (200 μl per dish), and the protein concentration was measured using Bradford assay with BSA as standard.

The caspase-3/7 activity in lysates were measured using the CASPASE-GLO® 3/7 assay (Promega) according to the standard protocol. In general, cell lysates were diluted in 100 μL of 2× Caspase buffer (100 mM HEPES, 200 mM NaCl, 2 mM EDTA, 20 mM TCEP, 20% glycerol, and 0.2% CHAPS, pH 7.4), to which 100 μL of CASPASE-GLO® 3/7 reagent was added to each solution. The mixture was gently mixed, and incubated in dark at room temperature for 1 h, followed by measuring luminescence (RLU) with a luminometer (Turner Biosystems) as directed by the luminometer manufacturer. Data were then background subtracted, normalized by ms of protein, and the caspase-3/7 activity was expressed as normalized luminescence per mg of protein.

Example 23

CASPASE-GLO® 3/7 Assays to Measure the Caspase-3/7 Activity in Saline- and 3×DOX-Treated Tumor Lysates HeLa tumor xenografted mice were treated with saline or 3×DOX (8 mg/Kg). After treatment, the mice were sacrificed, and the tumors were resected and lysed with RIPA buffer (1 g tissue/1 ml buffer). The solution was homogenized for 1 min on ice, three times. The lysed solution was kept on ice for another 30 min, and centrifuged at 14,000×g for 30 min at 4° C. The supernatant was collected, and the protein concentration was measured using Bradford assay with BSA as standard. The caspase-3/7 activity in the lysed solution was measured by CASPASE-GLO® 3/7 assay, and normalized to the protein concentration.

Example 24

Analysis of the Reaction of C-SNAF in Viable and Apoptotic HeLa (or MDA-MB-231) Cell Lysates Adherent HeLa (or MDA-MB-231) cells (approximately 8×10$^6$) were either non-treated or treated with STS (2 μM) for 4 h (or 2 μM DOX for 24 h). After replacing the medium containing STS with blank medium, the cells were kept growing for another 24 h. The culture medium was carefully removed and the cells were washed with cold 1×PBS. The cells were trypsinized to form cell pellets, and RIPA (RadioImmuno Precipitation Assay, sigma) buffer was added to cells using 100 μL of buffer per 4×10$^6$ cells. Then the cells were kept on ice for 0.5 h. The cell lysate was gathered, centrifuged at 14,000×g for 15 min at 4° C. The supernatant of the cell lysate was collected, and the caspase-3/7 activity in the lysate was determined by CASPASE-GLO® 3/7 assay. The cell lysate was diluted with caspase reaction buffer (2×, 1:1 diluted), and incubated with C-SNAF (5 μM) at 37° C. overnight and then injected into an HPLC system (Dionex) for analysis.

Example 25

Analysis of the Reaction of C-SNAF in Viable and Apoptotic HeLa Cells

Adherent HeLa cells (about 8×10$^6$) were either non-treated or treated with STS (2 μM) for 4 h. After replacing the medium containing STS with blank medium, the cells were kept growing for another 24 h. The culture medium was removed and the cells were washed with cold PBS (1×). The cells were trypsinized to form cell pellets, and RIPA® (RadioImmuno Precipitation Assay, Sigma, Inc.) buffer was added to cells using 200 μL of buffer per 4×10$^6$ cells. The cells were kept on ice for 0.5 h. The cell lysate was gathered, centrifuged at 14,000×g for 10 min at 4° C. The supernatant of the cell lysate was collected, and the caspase-3/7 activity in the lysate was determined by CASPASE-GLO® 3/7 assay. The cell lysate was diluted with caspase reaction buffer (2×, 1:1 diluted), and incubated with probe 15 (100 µM) at 37° C. overnight and then injected into an HPLC system (Dionex) for analysis.

Example 26

Epifluorescence Microscopy Imaging of DOX-Treated HeLa Cells

HeLa cells in #1.5 borosilicate 8-well chambered coverslips (Nunc) were either incubated with C-SNAF (2 µM) alone or co-incubated with DOX (1, 2, and 5 µM) and 2 µM C-SNAF, 2 µM C-SNAF together with caspase inhibitor (Z-VAD-fmk, 50 µM), or control probes D-ctrl and L-ctrl at 2 µM for 24 h. Then the medium was removed, the cells were carefully washed with PBS (1×) three times, and stained with nuclear binding probe Hoechst 33342 (2 µM) at 37° C. for 30 min. After several rinses with PBS (1×), the medium was replaced and the fluorescence images were acquired with DAPI and FITC filters.

Example 27

Flow Cytometry Analysis of Anti-Cancer Drug-Induced Apoptotic HeLa Cells

Approximately $10^5$ HeLa cells in 1 mL DMEM medium were seeded onto 12-well plates. The following day, the medium was replaced with 500 µL fresh medium containing STS (0, and 2 µM). After 4 h incubation, the medium containing STS was removed, and the cells were kept growing for 0 or 24 h to induce different level of apoptosis. After gentle wash with PBS (1×), the cells were detached from the plates with trypsin (100 µL per well), and the cell pellets were collected after centrifugation at 2000 rpm at 4° C. for 2 min. After wash with PBS (1×), the pellets were resuspended in 300 µL PBS (1×), and stained with Alexa Fluor Annexin V and PI using the ALEXA FLUOR 488 ANNEXIN V/DEAD CELL APOPTOSIS® Kit (Invitrogen: V13241) for flow cytometry. For the FLICA staining experiment, the cell pellets were resuspended in 1× wash buffer, and stained with FLICA (FAM) and PI using the VYBRANT® FAM Caspase-3 and -7 Assay Kit (Invitrogen: V35118). All assays were performed according to the manufacturer instructions, and the cell population was analyzed by FACScan analyzer using FITC (Annexin V and FLICA) and PI channels. The cell number for each flow cytometry analysis was approximately $5 \times 10^3$ to $10^4$, and the data was processed using FlowJo software.

For the DOX-induced apoptotic cells, HeLa cells in 12-well plates were treated with DOX (0, 1, and 5 µM) for 24 h, stained with Alexa Fluor Annexin V and PI or FLICA (FAM) and PI according to the aforementioned procedure, and applied for flow cytometry analysis.

Example 28

Flow Cytometry Analysis of Apoptotic HeLa Cells Labeling with C-SNAF

Approximately $10^5$ HeLa cells in 1 mL DMEM medium were seeded onto 12-well plates. The following day, the medium was replaced with 500 µL fresh medium containing STS (0, and 2 µM). After 4 h incubation, the medium containing STS was removed, and 500 µL fresh medium containing 2 µM C-SNAF, L-ctrl and D-ctrl was added to respective wells. For the inhibitor blocking experiment, the STS-treated cells were first incubated with the caspase inhibitor Z-VAD-fmk (50 µM, R&D Systems) for 30 min, and then 2 µM C-SNAF was added. All cells incubations were 24 h, followed by staining with FLICA (FAM) after trypsinization. After washing with PBS (1×) three times, the cell pellets were resuspended in 300 µL PBS and applied for flow cytometry analysis using the FITC and Cy5.5 channels. The cell number for each flow cytometry analysis was approximately 5000 to 10000, and the data was processed using FlowJo software.

For the DOX-induced apoptotic cells, HeLa cells in 12-well plates were co-incubated with DOX (5 µM) and 2 µM C-SNAF, L-ctrl and D-ctrl, or 2 µM C-SNAF together with 50 µM Z-VAD-fmk for 24 h. After washing with PBS (1×) three times, the cells pellets were resuspended in 300 µL PBS, and applied for flow cytometry analysis using the Cy5.5 channels. The cell number for each flow cytometry analysis was approximately $5 \times 10^3$ to $10^4$, and the data was processed using FlowJo software.

Example 29

Active Caspase-3 Immunohistochemistry Assay

Following fluorescence imaging studies at 4 h, tumor tissues were excised, frozen in Optimal Cutting Temperature medium (OCT) and sectioned into 10 µm slices. For active caspase-3 staining, the sections were fixed with cold acetone, blocked with avidin/biotin blocking kit and DAKO blocking, and immunostained with primary cleaved caspase-3 antibody (Asp175, 1:100, Cell signalling 9661) overnight at 4° C., followed by incubation for 30 min with biotinylated anti-rabbit IgG (1:300, Vector Labs) and 30 min with Cy3-conjugated streptavidin (1:300, Jackson ImmunoResearch). Then the sections were mounted in Vectashield mounting media containing DAPI (Vector Labs). The images were captured using an Olympus inverted fluorescence microscope (IX2-UCB) equipped with a Nuance multispectral imaging camera after excited and acquired at respective filters for DAPI, Cy3 and Cy5.5. The images were processed using the standard CRi Nuance software, analyzed using Image J software package (NIH), and showed at the same intensity scale for comparison.

Example 30

Statistical Analysis

Results are expressed as the mean±standard deviation unless otherwise stated. Statistical comparisons between two groups were determined by t-test, and between 3 or more groups by one-way ANOVA followed by a post-hoc Tukey's HSD test. Time course analysis between groups was performed by general linear model repeated-measures analysis. Correlation analyses were performed by one-tailed Spearman r (non-parametric). For all tests, $p < 0.05$ was considered statistically significant. All statistical calculations were performed using GraphPad Prism v. 5 (GraphPad Software Inc., CA, USA).

Example 31

Radiosynthesis

General

All chemicals unless otherwise stated were commercially available and used without further purification. Purification of 10 was carried on a high-performance liquid chromatograph (HPLC) equipped with Dionex 680 pump (Dionex Corporation, USA) and KNAUER UV detector K-2001 (KNAUER, Germany) using a Phenomenex Gemini C18 column (250×10 mm, 5 μm) and gradient conditions (method A): A: $H_2O+0.1\%$ TFA, B: $CH_3CN+0.1\%$ TFA; 0-2 min 5% B, 2-30 min 5-65% B, 30-40 min 60-95% B; 5.0 mL/min.

1 and 1-D were purified on a Dionex Ultimate 3000 chromatography system with a UVD 340U absorbance detector (Dionex Corporation, USA) and model 105S single-channel radiation detector (Carroll & Ramsey Associates, USA) using a Phenomenex Gemini C18 column (250× mm, 5 μm) and gradient conditions: for 1 (method B), A: $H_2O+0.1\%$ TFA, B: $CH_3CN+0.1\%$ TFA; 0-2 min 10% B, 2-40 min 10-60% B, 40-50 min 95% B, 50-60 min 10% B; 5.0 mL/min; for 1-D (method C), A: $H_2O+0.1\%$ TFA, B: $CH_3CN+0.1\%$ TFA; 0-2 min 10% B, 2-40 min 10-40% B, 40-50 min 95% B, 50-60 min 10% B; 5.0 mL/min. Analytical HPLC were performed on an Agilent 1200 Series HPLC system (Agilent Technology, USA) with ChemStation software (version B.04.02) equipped with a quaternary pump, UV diode array detector and model 105S single-channel radiation detector using a Phenomenex Gemini C18 column (250×4.6 mm, 5 μm) and gradient conditions: for 1 (method D), A: $H_2O+0.1\%$ TFA, B: $CH_3CN+0.1\%$ TFA; 0-2 min 20% B, 2-25 min 20-80% B, 25-28 min 95% B, 28-32 min 20% B; 1.0 mL/min; for 1-D (method E), A: $H_2O+0.1\%$ TFA, B: $CH_3CN+0.1\%$ TFA; 0-2 min 10% B, 2-10 min 10-15% B, 10-25 min 15-25% B, 25-28 min 95% B, 28-32 min 10% B; 1.0 mL/min with UV chromatograms recorded at 214 and 254 nm. The identity of the $^{18}F$-labeled products was confirmed by comparison with the analytical HPLC retention time of their non-radioactive reference molecule or by co-injection before administration to animal.

Example 32

Synthesis of [18F]Azide (10)

10 was fully-automated synthesized in a Tracerlab FX-FN module (GE Healthcare, USA). Briefly, no-carrier added [$^{18}F$]-fluoride was produced via the $^{18}O(p,n)^{18}F$ nuclear reaction by irradiation of enriched [$^{18}O$]$H_2O$ in a PETtrace cyclotron (GE Healthcare, USA). [$^{18}F$]Fluoride was trapped on an anion-exchange resin cartridge (Macherey-Nagel Chromafix 30-PS-HCO3 pre-conditioned with 1 mL of EtOH, 1 mL of $H_2O$ and then blown dry). The cartridge was eluted with a solution of Kryptofix K2.2.2® (15 mg) and potassium carbonate (3 mg) in $H_2O$ (0.1 mL) and $CH_3CN$ (0.9 mL). Following azeotropic drying, compound 9 (3.0 mg in 1.0 mL dry DMSO) was added to the K[$^{18}F$]/K2.2.2. complex and the mixture was heated for 20 min at 110° C. to yield 10.

After cooling to room temperature, the reaction mixture was loaded on semi-prep HPLC (method A). The fraction corresponding to the peak of the desired product (retention time approximately 21 min) was collected in a round bottom flask containing sterile water (20 mL), and then transferred to an adjacent customized module for solid phase extraction (SPE) using a C-18 Sep-Pak. 10 trapped on C-18 cartridge was eluted with diethyl ether (2 mL) through a $Na_2SO_4$ cartridge into a 5 mL V-vial with stirrer bar in the customized module. The diethyl ether was removed under helium stream at ambient temperature and the dried labeling agent was reconstituted with THF (50 μL) for further click chemistry.

Example 33

Synthesis of the Activatable Tracer 1 ([$^{18}F$]C-SNAT)

Click chemistry assisted by $Cu(CH_3CN)_4PF_6$ and BPDS: To a solution of 10 in THF (50 mL) was added DMF solution (25 mL) of the active probe 3a (0.6 mg, 0.5 mmol), $Cu(CH_3CN)_4PF_6$ (50 mL, 200 mM in MeCN) and BDPS (bathophenanthrolinedisulfonic acid disodium salt trihydrate, 100 mL, 50 mM in PB buffer, pH=7), and the reaction mixture was kept at 60° C. for 30 min. Crude product was diluted with 2 mL water and injected on semi-prep for purification (method B). The fraction corresponding to the peak of the desired product (retention time at approximately 26 min) was collected and diluted with 20 mL of water; this solution was loaded on the C-18 light cartridge and eluted out first with 1 mL saline/water (50/50) and then another 4 mL of saline. Both eluted solutions were combined as final product 1.

Click Chemistry Assisted by $CuSO_4$ and Sodium Ascorbate

To a solution of 10 in THF (50 mL) was added 1 M HEPES solution (100 mL) of the active probe 3a (1.2 mg, 1 mmol), $CuSO_4$ (300 mM, 10 μL) and sodium ascorbate (300 mM, 10 μL) and reaction mixture was kept at 40° C. for 20 min. Crude product was diluted with 2 mL of water and injected on semi-prep for purification (method B). Final product 1 was formulated in saline with 10% ethanol by SPE.

Example 34

Synthesis of the Control Tracer 1-D

Click chemistry assisted by $CuSO_4$ and sodium ascorbate: To a THF solution of 10 in THF (50 mL), 1 M HEPES/DMSO (=1:1) solution (50 mL) of the control probe 3b (0.5 mg, 0.4 mmol), $CuSO_4$ (300 mM, 14 μL) and sodium ascorbate (300 mM, 14 μL) were added and reaction mixture was kept at 40° C. for 20 min. An acetonitrile solution of 11 (250 mM, 200 mL) was added into reaction mixture and kept at 40° C.; the reaction was monitored by checking an aliquot of reaction sample by analytical HPLC. When 3b was consumed based on HPLC chromatograph under UV 254 nm, crude product was diluted with 2 mL water and injected on semi-prep for purification (method D). Product fraction was eluted out at approximately 42 min and final product 1-D was formulated in saline with 10% ethanol by SPE.

Example 35

Cell Uptake

HeLa cells (cultured in DMEM with 10% FBS and 1% ampicillin) were grown in a 6 well plate culture dish for 24 h. The wells were then divided into 3 groups. Group 1 wells were cultured normally for 24 h, then the medium was changed and the cells were cultured for another 24 h. Group 2 and 3 wells were cultured with 2 μM doxorubicin (DOX) for 24 h, then the medium was changed and the cells were cultured for another 24 h, group 2 in normal culture medium without doxorubicin and group 3 in normal culture medium without doxorubicin but together with 50 µM Z-VAD-FMK, a caspase-3 inhibitor.

After 48 h, 10 µCi (0.37 MBq) of 1 were added to all three groups and incubated for additional 4 h. Then the medium was removed, the cells washed 3 times with phosphate buffered saline, and 1 mL of Tryp-LETM Express was added and the cells were left for 1-2 min to allow to detach. The cell/Tryp-LE solution was counted in a gamma counter and the radioactivity was normalized to the protein concentration (determined by comparison with BSA standards in each vial.

Example 36

Cell Uptake HPLC Analysis

In a second experiment following the same procedure, the cell/Tryp-LE solutions were placed in a veil and centrifuged at 1200×g for 2 min, the supernatant were removed and the pellets were homogenized with a sonicator (Bronson Sonifier 150) in 1 mL of MeOH. The supernatant was collected and analyzed on HPLC (method D for 1; method E for 1-D). The pellets and part of the MeOH supernatants were saved and counted for radioactive content. Parent 1 and 2 were run on HPLC as well for comparison.

Example 37

Caspase-3 Level in Apoptotic Cells

HeLa cells were incubated with different concentrations of doxorubicin (0, 1, 2 and 5 µM) and the cell/Tryp-LE solution was centrifuge at 11,750×g for 5 min, the supernatant was removed and 1 mL/g Riba buffer (Sigma) was added. The cells were left for 15 min on ice and homogenized with a sonicator (Bronson Sonifier 150) and the suspension was analyzed for Caspase-3 activity with a CASPASE-GLO® kit from Promega.

Example 38

Stability in Mouse Serum

To the mouse serum (500 µL) 100 µL (approximately 100 µCi/3.7 MBq) of radioactive sample was added and the mixture was incubated at 37° C. At each time point, 100 µL of sample was taken and after mixing with 100 µL of acetonitrile was centrifuged at 9,400×g for 5 min. The resulting supernatants were collected, and an aliquot of each supernatant (100 µL) was diluted with 100 µL of water and analyzed via the same HPLC method used for quality control (fitted with a highly sensitive positron detector for radioactivity). The percent ratio of intact compound to the total radioactivity on the HPLC chromatogram was calculated as %=[(peak area for intact compound)/(total peak area)]×100.

Example 39

Animal Model

Mice were injected subcutaneously on the right shoulder with an estimated 1-2 million HeLa cells. The HeLa cells were allowed to establish a tumor xenograft and to grow to the size of 1 cm in diameter. A subset of the mice was treated with intratumoral injections of 0.2 mg (in 20 µL) doxorubicin. Four days later, the animals were killed, the tumors removed and quickly frozen using dry ice. The following day, tumors were cut into small pieces, weighted and 1 mL/g Riba buffer was added. They were kept on ice for 30 min and then homogenized with a sonicator (Bronson Sonifier 150). The lysed tumor solutions were centrifuged at 11,750×g for 15 min at 4° C. The supernatant was analyzed for caspase-3 activity using the CASPASE-GLO® kit (Promega) and for protein concentration using the standard BSA absorption assay.

Example 40

PET Imaging

One group of animals was scanned at baseline (before treatment) and 4 days post treatment with 0.2 mg doxorubicin injected into the tumor. On the day of scanning, the animals were moved from their housing area to the PET scanner around 1 h prior to the experiment. They were constrained shortly in a tail veiner and injected intravenously, with 440±97 µCi (16±3 MBq) [$^{18}$F]C-SNAT formulation. They were anesthetized with 2% isoflurane shortly before placement in an R4 microPET scanner (Siemens Medical Solutions, USA). The anesthesia were continued with 2% isoflurane doing 5 min of acquisition. Scans using the control tracer 1-D (173±73 µCi/9±4 Mbq in 200 µL formulation) were carried out in a similar manner using two groups (one baseline and one treated) instead of the same animals at baseline and after treatment. The images were reconstructed using a standard 2D reconstruction without attenuation correction.

The reconstructed images were analyzed by making two volumes of interest (VOI), one on the tumor and one located on the left shoulder corresponding to muscle/bone mixture. The percent of injected dose per gram tissue (% ID/g) was calculated in each VOI and the ratio between tumor and muscle uptake was calculated based on this uptake (uptake in tumor/uptake in muscle region). The effect of treatment was calculated as the difference in uptake of [$^{18}$F]C-SNAT at baseline and after treatment.

Example 41

Biodistribution

Mice were administered [$^{18}$F]C-SNAT (100-200 µCi/3.7-7.4 MBq in 100-200 µL of 0.9% saline solution) via tail vein injection and then euthanized by bilateral thoracotomy under anesthesia at 2 h after injection of tracer (n=3). All samples (tumor, heart, whole brain, gallbladder, kidney, liver, lung, muscle, bone, spleen, whole blood) were removed quickly following euthanasia and placed in pre-weighed test tubes. Standard solutions of the tracer were prepared by diluting approximately 100 µCi (3.7 MBq) tracer in 100 mL of water, of which 1 mL of aliquots were used for reference counting.

The test tubes containing tissue samples were weighed and the radioactivity was measured by an automated gamma counter (Cobra Model 5002, Packard, USA) along with the standard solutions. The ratios of the radioactivity in organs to muscle are shown in Table 2.

TABLE 2

Ex vivo biodistribution data of [$^{18}$F]C-SNAT (1) 2 h post injection.

| Region (n) | Ratio of % ID/g over muscle ± SEM. |
|---|---|
| Muscle (5) | 1.0 ± 0.5 |
| Bone (5) | 2.4 ± 1.5 |
| Brain (5) | 0.5 ± 0.2 |
| Heart (3) | 4.5 ± 2.4 |
| Kidney (5) | 124.2 ± 46.6 |
| Liver (5) | 22.9 ± 9.7 |
| Lung (3) | 4.1 ± 1.8 |
| Plasma (2) | 4.0 ± 1.8 |
| Spleen (5) | 1.7 ± 0.7 |
| Tumor (2) | 5.6 ± 2.3 |
| Whole Blood (5) | 5.1 ± 2.4 |

Example 42

Statistical Analysis

Comparisons were done using a one-sided unpaired t-test, except for comparing treated to baseline of [$^{18}$F]C-SNAT where a one-sided paired t-test was used.

Example 43

An $^{18}$F label was introduced to a propargylglycine residue between CHQ and the cysteine residue via the Click reaction. Upon the activation of caspase-3 that cleaves the peptide DEVD, the amino of the cysteine residue is released free, and the reductive intracellular environment reduces the disulfide to generate a free thiol. It has been demonstrated that free cysteine and CHQ can undergo intramolecular cyclization through the condensation reaction with a fast kinetics (half-life at 119.8±10.2s). The cyclized products are more hydrophobic and then self-assemble in situ into nanoparticles with a high density of $^{18}$F positron activity, resulting in prolonged retention in apoptotic cells and thus enhanced PET imaging contrast.

The control tracer 1-D was designed to have a similar structure and pharmacokinetics to 1 but not be cleavable by caspase-3 and undergo cyclization and aggregation. Therefore, it contained the same substrate sequence of caspase-3 but made in D-amino acids. In addition, the mercapto group of the cysteine side chain was methylated and it did not have the cyano substitution on its quinoline.

The precursor 3a for synthesizing 1 was prepared according to the scheme shown in FIG. 19, starting from N-Boc-propragylglycine that was coupled with 6-amino-2-cyanobenzothiazole (CBT) to afford 4. Deprotection of N-Boc group followed by coupling with protected D-cysteine provided the dipeptide 5. Condensation of 5 and 6a between the CBT group and cysteine occurred under mild conditions, subsequent deprotection of N-Boc and S-Trt groups and protection of the thiol group with -SEt producing intermediate 7a. The amino group of 7a was coupled with the protected caspase-3 substrate, Ac-Asp(tBu)-Glu(tBu)-Val-Asp(tBu)-OH (8a), and final deprotection of the t-Butyl group gave the desired precursor 3a. The precursor 3b for the control tracer 1-D consisted of D-peptide amino acids, and was prepared similarly.

The prosthetic group 10 was obtained in a single step substitution of 9 by $^{18}$F in the presence of $K_{222}$ with a radiochemical yield (RCY) of 37±8% (n=16), as shown in FIG. 20. All RCYs and specific radioactivities were decay-corrected to end-of-bombardment (EOB) as indicated and reported as means±SD.

The Click labeling of 3a by 10 occurred in a mild condition (40-60° C.) with copper ion as the catalyst. When $CuSO_4$ and sodium ascorbate were employed, the RCY in this step was 15±6% (n=6) for 1, and 25±8% (n=4) for 1c. When $Cu(CH_3)_4PF_6$ and BPDS were applied, the RCY increased to 30±5% (n=4) for 1 with less side products formed, probably due to improved stability of 1 in the absent of sodium ascorbate. The final product was purified on a semi-preparative HPLC and formulated in saline containing less than 10% EtOH. During the HPLC purification of 1-D, because both the precursor 3b and product 1-D had very close retention times ($\Delta t_R$<0.1 min), additional [$^{19}$F]azide 11 was added to consume remaining 3b and afford a product whose retention time was shifted to a much earlier time ($\Delta t_R$>10 min), which significantly improved the HPLC purification (FIGS. 24A and 24B). Thus, 1 and 1-D were successfully obtained with overall RCYs and specific radioactivities of 10±0.4% and 63±7.4 GBq/μmol (1.7±0.2 Ci/μmol) for 1; 7±3% and 99.9±33.3 GBq/μmol (2.7±0.9 Ci/μmol) for 1-D (radiochemical purity >99%, chemical purity >95%) after a total synthesis time of 3-3.5 h from EOB.

Example 44

The serum stabilities of 1 and 1-D were tested in human and mouse serum. Both tracers were more than 90% intact in human serum after 2 h incubation at 37° C.; in mouse serum, 1-D displayed higher stability than 1, i.e. 90% of intact 1-D versus 60% of intact 1 was observed after 1 h incubation, probably due to the replacement by the D-amino acids. The intramolecularly cyclized product 2 was also tested and showed greater than 90% integrity in mouse serum after 2 h incubation, as shown in FIG. 25.

Example 45

To evaluate the activatable PET tracer 1 for caspase-3 detection, it was first incubated with recombinant caspase-3 in buffer. Within 1 h, 90% of 1 was shown to cyclize and afford two cyclized isomers based on the Radio-HPLC chromatograph, as shown in FIG. 21A. As expected, under the same condition, 1-D could not be cleaved by caspase-3 and no cyclization products but 1-D itself was observed.

Example 46

PET tracer 1 was applied to detect caspase-3 in apoptotic cells in vitro. HeLa cells were incubated with doxorubicin (Dox) (2 μM) for 24 h to induce apoptosis. Caspase-3 assays confirmed that the lysates of Dox-treated cells showed 9.5-fold higher caspase-3 activity than that of non-treated cells (FIG. 26A). Both Dox-treated and non-treated cells were then incubated with 1 for 4 h.

The retained $^{18}$F activity in Dox-treated cells was 2.2-fold of that of non-treated cells. As control, a caspase-3 inhibitor (Z-VAD-fmk) was applied to a similar set of Dox-treated cells, which decreased the retained $^{18}$F activity to 1.3-fold (FIG. 21B). Both Dox-treated and non-treated cells were subject to extraction and analysed by Radio-HPLC. The major radioactive fractions from Dox-treated cells were cyclized products of 2 (FIG. 21A), but it was not observed in the extraction from non-Dox-treated cells. These results support that caspase-3 activity can trigger the cyclization of PET tracer 1 in living cells and enhance the retention of the radioactivity.

Example 47

The biodistribution of the activatable PET tracer 1 was performed in nude mice that were euthanized at 120 minutes post injection. Organs were collected, weighed, and analyzed with a gamma counter for radioactivity uptake as shown in Table 1.

Briefly, kidney and bladder showed high levels of absolute uptake, suggesting primary clearance through the renal system. Low tracer uptake in muscle promises minimal background signal in PET imaging. Uptake in the brain tissue was low, suggesting that the anionic 1 could not cross the blood-brain barrier.

Example 48

Evaluation of activatable PET tracer 1 and control tracer 1-D for PET imaging of caspase-3 activity in vivo was performed in HeLa tumor xenograft-bearing nude mice. Tumors were implanted and grown for a minimum of 10 d before receiving intratumoral injection of 0.2 mg DOX (20 µL). 1 or 1-D (5-15 MBq/135-405 µCi) was injected through the tail vein for PET imaging 4 d post treatment. Static PET scans (5 min) were performed 65, 125 and 182 mins post tracer injection. FIG. 22 shows representative PET images of 1 before and after DOX treatment in same mouse and 1-D in a different mouse after DOX treatment.

Quantification of the PET images with the activatable tracer 1 revealed that the uptake (% ID/g) of the $^{18}F$ activity in tumors significantly increased after DOX treatment: from 0.81±0.28 (baseline) to 1.17±0.17 (treated) at 65 min, from 0.67±0.24 (baseline) to 1.29±0.07 (treated) at 182 min (FIG. 23A); this result correlates well with the caspase-3 level detected in tumors—a 1.9 fold increase in treated tumors (FIG. 26B). The uptake difference between baseline and treated increased from 0.36±0.15 at 65 min to 0.63±0.11 at 182 min (FIG. 23B), and the uptake ratio between tumor and muscle (T/M) increased from 3.30-fold at 65 min to 7.00-fold at 182 min in treated tumors (FIG. 23C).

In contrast, the uptake of the control tracer 1-D in both treated and non-treated tumors was much lower than that of 1 (FIG. 23A), and the uptake difference between before and after treatment (less than 0.2% ID/g) was much smaller than that with 1 (FIG. 23B). The ratio of T/M did not show significant increases either (FIG. 23C). These PET imaging results demonstrate that the activatable PET tracer 1 could image caspase-3 activity in drug-treated tumors in vivo and that both caspase-3 activation and cyclization are required for the enhanced imaging contrast in apoptotic tumors.

Example 49

Synthesis of 13

A mixture of (t-BuO)$_3$DOTA-COOH (0.11 mmol), HBTU (0.12 mmol), and DIPEA (0.21 mmol) in dry DMF (5 ml) was stirred at room temperature for 5 min, to which was added compound 4 (0.1 mmol). The reaction solution was kept stirring at room temperature for another 2 h. After the reaction was completed, the mixture was poured into water (40 ml). The precipitate was collected after centrifugation for 5 min (3000 rpm), which was further dried after lyophilization. MS: calcd. for $C_{95}H_{144}N_{17}O_{22}S_4$ [(M+H)$^+$]: 2003.0. found MALDI-MS: m/z 2002.9.

Example 50

Synthesis of 14

Compound 13 from last step was deprotected using a solution of TFA/ACN/TIPSH (95/2.5/2.5) at room temperature for 3 h. After the reaction, the solvent was removed under vacuum, and the residue was purified by HPLC to obtain 14 as light yellow powder after lyophilization. 56% yield from 4. $^1$H NMR (400 MHz, DMSO-d$_6$) δ. MS: calcd. for $C_{71}H_{94}N_{17}O_{22}S_4$ [(M−H)$^−$]: 1664.6. found MALDI-MS: m/z 1664.3.

Example 51

Synthesis of MR Probe 15

A solution of 14 in water was carefully added 0.5 M NaHCO$_3$ solution to adjust the pH value to 7, which was following by addition of a solution of GdCl$_3$ (3-5 equivalents) to (8) in water. After stirring at room temperature for 10 min, the pH value of the reaction solution was further adjusted to 7 using 0.5 M NaHCO$_3$ solution. The reaction mixture was bubbled with Ar, and then kept stirring at room temperature overnight. After centrifugation (2500 rpm, 3 min), the supernatant was purified by HPLC to obtain probe 15 as light yellow powder after lyophilization. 75% yield. MALDI-MS: calcd. for $C_{71}H_{93}GdN_{17}O_{22}S_4$ [(M+H)$^+$]: 1821.5. found MALDI-MS: m/z 1821.4. HRMS: calculated for $C_{71}H_{94}GdN_{17}O_{22}S_4$ [(M+2H)$^{2+}$]: 1822.4883, observed. HR-ESI/MS: [(M+2)/2]$^+$911.2458.

Example 52

Synthesis of Two-Photon Imaging Probe 1-Eu$^{3+}$ (16)

Similar to the synthesis of probe 15, was obtained after chelated of 8 with EuCl$_3$. 79% yield. MALDI-MS: calcd. for $C_{71}H_{91}EuN_{17}O_{22}S_4$ [(M−H)$^−$]: 1814.5. found MALDI-MS: m/z 1814.4.

Example 53

Synthesis of 1-Ctrl (19)

Synthesis of 17

A mixture of (t-BuO)$_3$DOTA-COOH (0.11 mmol), HBTU (0.12 mmol), and DIPEA (0.21 mmol) in dry DMF (5 ml) was stirred at room temperature for 5 min, to which was added compound 8 (0.1 mmol). The reaction solution was kept stirring at room temperature for another 2 h. After the reaction was completed, the mixture was poured into water (40 ml). The precipitate (17) was collected after centrifugation for 5 min (3000 rpm), which was further dried after lyophilization. MS: calcd. For $C_{64}H_{145}N_{16}O_{22}S_4$ [(M+H)$^+$]: 1978.0. found MALDI-MS: m/z 1978.1.

Synthesis of 18

Compound 17 was deprotected using a solution of TFA/DCM/TIPSH (95/2.5/2.5) at room temperature for 3 h. After the reaction, the solvent was removed under vacuum, and the residue was purified by HPLC to obtained 18 after lyophilization. 53% yield from 4.

$^1$H NMR (400 MHz, DMSO-d$_6$) δ 10.36 (s, 1H), 9.01 (d, J=4.1 Hz, 1H), 8.80 (d, J=8.1 Hz, 1H), 8.59 (s, 1H), 8.48 (br, 2H), 8.40 (s, 1H), 8.29 (s, 1H), 8.23 (d, J=7.6 Hz, 2H), 8.11 (d, J=8.7 Hz, 1H), 8.03 (m, 2H), 7.93-7.84 (m, 1H), 7.77-7.59 (m, 4H), 5.31 (t, J=9.0 Hz, 1H), 4.51-4.62 (m, 3H), 4.36-4.49 (br, 2H), 4.19 (s, 2H), 4.09 (s, 2H), 3.91 (s, 2H), 3.78-3.57 (m, 4H), 3.30-3.48 (m, 10H), 3.27 (s, 2H), 2.92-3.24 (m, 12H), 2.81-2.57 (m, 4H), 2.19 (m, 2H), 2.10-1.98 (m, 2H), 1.92 (s, 2H), 1.62-1.85 (m, 5H), 1.32-1.55 (m, 4H), 1.21 (t, J=7.3 Hz, 3H), 0.89-1.11 (m, 4H), 0.66-0.85 (m, 6H). $^{13}$C NMR (101 MHz, DMSO-d$_6$) δ 174.79, 172.56, 172.40, 171.90, 171.80, 171.72, 171.56, 171.47, 170.60, 170.36, 170.30, 169.83, 164.92, 159.84, 159.22 (TFA, J=35 Hz), 158.73, 149.31, 144.16, 142.94, 138.75, 136.97, 136.52, 130.75, 126.96, 124.85, 122.84, 120.40, 116.65 (TFA, J=294 Hz), 112.16, 107.70, 79.93, 72.93, 66.88, 58.43, 55.35, 54.62, 54.32, 53.18, 53.14, 52.71, 51.24, 50.48, 50.35, 48.91, 48.54, 36.67, 35.28, 32.30, 31.91, 31.06, 30.74, 29.07, 27.70, 27.52, 23.61, 23.13, 19.84, 19.75, 18.65, 18.47, 17.63, 14.92. MS: calcd. for $C_{70}H_{97}N_{16}O_{22}S_4$ [(M+H)$^+$]: 1641.6. found MALDI-MS: m/z 1641.8.

Synthesis of 1-Ctrl (19)

A solution of 18 in water was carefully added 0.5 M NaHCO$_3$ solution to adjust the pH value to 7, which was following by addition of a solution of GdCl$_3$ (3-5 equivalent) to (18) in water. After stirring at room temperature for 10 min, the pH value of the reaction solution was further adjusted to 7 using 0.5 M NaHCO$_3$ solution. The reaction mixture was bubbled with Ar, and then kept stirring at room temperature overnight. After centrifugation (2500 rpm, 3 min), the supernatant was purified by HPLC to obtain probe 19 as light yellow powder after lyophilization. 82% yield. MALDI-MS: calcd. for $C_{70}H_{94}GdN_{16}O_{22}S_4$ [(M+H)$^+$]: 1796.5. found MALDI-MS: m/z 1796.9. HRMS: calculated for $C_{71}H_{94}GdN_{17}O_{22}S_4$ [(M+2H)$^{2+}$]: 1822.4883. obsvd. HR-ESI/MS: [(M+2)/2]$^+$911.2458.

Example 54

Synthesis of 1-FITC (22)

Synthesis of 20

Compound 4 was deprotected using a solution of TFA/CH$_3$CN/TIPSH (95/2.5/2.5) at room temperature for 3 h. After the solvent was removed, cold Et$_2$O was added, and the precipitate was dried under vacuum to give compound (5) in 83% yield without further purification.

$^1$H NMR (400 MHz, DMSO-d$_6$) δ 10.37 (s, 1H), 8.59 (d, J=9.7 Hz, 1H), 8.43 (d, J=8.0 Hz, 2H), 8.36-8.13 (m, 4H), 8.12-7.86 (m, 5H), 7.66 (m, 5H), 7.53 (d, J=9.2 Hz, 1H), 7.46 (s, 1H), 5.30 (t, J=9.0 Hz, 1H), 4.66-4.27 (m, 5H), 4.18 (s, br, 2H), 4.13-4.04 (m, 1H), 3.36 (m, 3H), 3.15-3.02 (m, 1H), 2.96 (m, 1H), 2.85-2.64 (m, 5H), 2.56 (m, 2H), 2.44 (m, 1H), 2.16 (m, 2H), 2.09-1.63 (m, 11H), 1.54 (s, br, 2H), 1.37 (m, 2H), 1.21 (t, J=6.9 Hz, 3H), 0.77 (m, 6H); $^{13}$C NMR (101 MHz, DMSO) δ 174.81, 172.40, 172.36, 171.82, 171.70, 171.42, 170.31, 169.81, 164.92, 159.87, 159.39, 149.32, 144.30, 138.72, 137.22, 136.99, 131.39, 131.01, 130.58, 125.40, 124.89, 124.81, 120.39, 118.62, 112.18, 106.87, 79.94, 66.76, 58.39, 54.10, 53.19, 52.65, 50.48, 50.29, 39.38, 36.70, 36.64, 36.48, 35.30, 32.28, 31.75, 31.11, 30.73, 29.11, 27.51, 27.30, 23.17, 23.05, 19.76, 18.71, 14.96. MS: calcd. for $C_{55}H_{70}N_{13}O_{15}S_4$ [(M+H)$^+$]: 1280.4. found MALDI-MS: m/z 1280.8.

Synthesis of 1-FITC (22)

To a solution of 20 (5 mg) in dry DMF (0.5 ml) was added FITC-NCS (1.2 mg) and DIPEA (5 μl), and the mixture was kept stirring at room temperature for 1 h. After the reaction was completed, the mixture was purified by HPLC to afford 1-FITC (22) in 57% yield. MS: calcd. For $C_{94}H_{110}N_{14}O_{28}S_7$ [M$^+$]: 2106.6. found MALDI-MS: 2106.2.

Example 55

MR Imaging Protocol

A series of solutions containing contrast agents with five different concentrations (0.05-0.5 mM) in Caspase buffer (pH 7.4) were treated with or without Casp-3 (50 nM) at 37° C. overnight. The solutions were placed in PCR tubes, bundled together, and MR-imaged at 1 T (Bruker Icon, Bruker BioSpin Corp.), 0.5, 1.5 and 3 T (Signa HDx, GE Healthcare) at room temperature.

The scanning procedure began with a localizer and then consisted of a series of inversion-prepared fast spin echo scans, identical in all aspects (TR 8000 ms (6000 ms for Bruker Icon), TE minimum, field of view 6 cm, slice thickness 2 mm, matrix 128×128, NEX 1) except for the inversion time (TI) that was varied as: 4000, 2400, 1200, 800, 600, 400, 300, 200, 100, and 50 ms. For quantitative data analysis, the acquired MR images were transferred as DICOM images to an offline workstation, and signal intensities were extracted from each of the 5 samples at each of the 10 TI times by manual region of interest (ROI) placement and voxel averaging within the ROI.

Signal intensity versus TI relationships were fit to the following exponential T1 recovery model by non-linear least squares regression: SI (TI)=S0[1−2*exp(−TI/T1)+exp(−TR/T1)]. Relaxation rates (R1) were determined as 1/T1. Longitudinal relaxivities (r1, units of mM$^{-1}$s$^{-1}$) were calculated as the slope of R1 vs [Gd] after the determination of true Gd concentration of each sample by the ICP-MS measurement.

Example 56

Caspase (human, recombinant from *E. coli*) assays were performed for caspase-3 (4.9×10$^{-3}$ U; 7.35×10$^{-4}$ mg, Sigma), -7 (18.3 U; 7.35×10$^{-4}$ mg, Calbiochem), and -9 (0.3 U; 7.35×10$^{-4}$ mg, Calbiochem). All caspase assays were conducted in caspase buffer with 50 mM HEPES, 100 mM NaCl, 1 mM EDTA, 10 mM TCEP, 10% glycerol, and 0.1% CHAPS at pH 7.4.

Cathepsin B (human liver; 0.27 U; 7.35×10$^{-4}$ mg, Calbiochem) and Legumain (human, recombinant from mouse myeloma cell line; >250 pmol/min/μg; 7.35×10$^{-4}$ mg, R&D Systems) were conducted in reaction buffer with 50 mM sodium acetate, 50 mM NaCl, 0.5 mM EDTA and 10 mM TCEP at pH 5.5. The C-SNAF was diluted in the respective enzyme reaction buffer (25 μM, 1 mL) and remained at room temperature for 10 min, to which was added respective enzymes.

Example 57

Cell Culture

HeLa human cervical adenocarcinoma epithelial cells were cultured in Dulbecco's modified eagle medium (GIBCO) supplemented with 10% fetal bovine serum (FBS, GIBCO), 100 U/mL penicillin and 100 µg/mL streptomycin (GIBCO). For epifluorescence microscopy experiments, cells were plated onto #1.5 borosilicate 8-well chambered coverslips and grown to about 70% confluence. For cell uptake and flow cytometry experiments, HeLa cells were plated onto 12-well clear plates and grown to about 70% confluence. For MR imaging of cell pellets experiment, HeLa cells were cultured in a cell culturing dish (75 mm), and grown to about 70% confluence.

Example 58

Cell Viability Study

About $2 \times 10^5$ HeLa cells in 1 mL DMEM medium were seeded onto 12-well plates. The following day, the medium was replaced with 1 ml of fresh medium, or medium containing probe 15 or Dotarem (200 µM). After 24 h incubation, the medium was removed, and the cells were trypsinized. The cell number was counted using trypan blue assay. The viability of cell with blank medium was set as 100%, and cells incubating with 1 or Dotarem were normalized to that in blank medium.

Example 59

In Vivo MR Imaging

In vivo MR imaging was performed on an Aspect M2 1T permanent magnet (Aspect Imaging, Shoham, Israel) using a 40 mm Transmit/Receive mouse body coil. During imaging, the animals were anaesthetized with isofluorane and their respiration and body temperature were constantly monitored. Intravenous contrast injection at 0.1 mmol/kg concentration was administered in a 100 µL volume for every imaging session. Multi-slice (312 µm in-plane, 12 slices with 1 mm thickness) T1-weighted spin echo images (TE/TR=8.9/250 ms, matrix 128×128, FOV=40 mm, NEX=6) were acquired, one before contrast injection and then every 4 min up to 4 h after contrast injection. A 1 mM Dotarem reference tube was inserted in the field of view to enable inter-session variability correction during post-processing. Each animal underwent two imaging session; one before DOX treatment (baseline), and one after DOX treatment (treated).

Example 60

Analysis of MRI Data

Acquired MR data were transferred as DICOM images to an offline workstation and ImageJ (NIH) was used for post processing and quantitative image analysis. This consisted of manual segmentation of tumor ROI for each slice, slice-wise normalization of mean tumor signal intensity with the 1 mM Dotarem reference standard to account for inter-session variability, followed by combining these normalized, slice-wise values to generate mean volumetric tumor signal intensities (SI) for each time point.

Example 61

Signal Enhancement (SE)

Signal enhancement was calculated at each time point as the difference between the tumor SI at that time point and the tumor SI in the pre-contrast (t=0) dataset.

$SE(t)=SI(t)-SI(t=0)$; for each mouse, for every session

Example 62

Percentage Difference in Signal Enhancement (% D)

This metric was used to quantify the difference in SE between the baseline (before DOX treatment) session and the treated session for each mouse, as a means to tease out the difference between the two contrast agents, probe 1 and 1-cntl (19) over the time course of the imaging session.

$\% D(t)=[SE(t,\text{treated})-SE(t,\text{baseline})]/SE(t,\text{baseline})$; for each mouse.

Example 63

Mice were implanted with HeLa tumor xenografts subcutaneously on the left shoulder. Once the tumors reached 0.7-0.8 mm in largest diameter, mice were treated with radiation therapy. Radiation therapy was delivered with a single 225 kV beam using the Kimtron IC 225 irradiator (Kimtron Medical, Woodbury, Conn.). The subcutaneous tumors received a dose of 7.6 Gy, which was measured in vivo with thermoluminescent dosimeters calibrated in the treatment beam. Following treatment, MR imaging was performed exactly as described for the chemotherapy mouse model, except that it occurred 24 h, 48 h, or 72 h post-treatment as shown in FIGS. 33A-35B.

What is claimed:

1. An activatable probe comprising a self-cyclizing molecule that comprises a cysteine moiety, a 2-cyano-6-hydroxyquinoline moiety, and an amino luciferin scaffold, and wherein the activatable probe further comprises a detachable capping moiety, wherein the detachable capping moiety is a peptide having an amino acid sequence consisting of L-aspartate-glutamate-valine-aspartate and conjugated to the cysteine moiety of the self-cyclizing molecule by a peptidase-cleavable bond, and wherein the activatable probe further comprises a detectable imaging moiety attached thereto.

2. The activatable probe of claim 1, wherein the peptidase-cleavable bond conjugating the detachable capping moiety to the cysteine moiety is selected from a caspase-3-cleavable bond or a caspase-7-cleavable bond.

3. An activatable probe comprising a detachable capping moiety conjugated to a self-cyclizing molecule comprising a cysteine moiety, a 2-cyano-6-hydroxyquinoline moiety, and an amino luciferin scaffold, and a detectable imaging moiety, wherein the detachable capping moiety is a peptide having an amino acid sequence consisting of L-aspartate-glutamate-valine-aspartate and conjugated to the cysteine moiety by a peptidase-cleavable bond.

4. The activatable probe of claim 1, wherein the self-cyclizing molecule has the formula I:

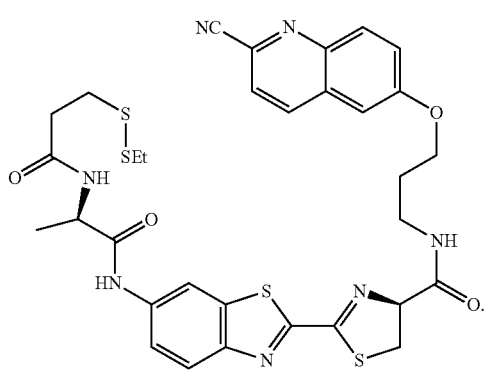

5. The activatable probe of claim 1, wherein the detectable imaging moiety is an optically detectable label, a positron electron transmission detectable label, or a magnetic resonance imaging (MRI) detectable label.

6. The activatable probe of claim 5, wherein the detectable imaging moiety is a fluorophore.

7. The activatable probe of claim 5, where the detectable imaging moiety detectable by positron electron transmission is selected from the group consisting of: $^{11}$C, $^{13}$N, $^{15}$O, $^{17}$F, $^{18}$F, $^{75}$Br, $^{76}$Br, and $^{124}$I.

8. The activatable probe of claim 5, wherein the activatable probe further comprises a chelating agent and the detectable imaging moiety is a magnetic resonance imaging (MRI) detectable label, and wherein said detectable label is a metal ion chelated to the chelating agent.

9. The activatable probe of claim 8, wherein the metal ion is gadolinium (Gd), thulium (Tm), europium (Eu), or a combination thereof.

10. The activatable probe of claim 6, further comprising a quenching moiety attached to the detachable capping moiety.

11. The activatable probe of claim 1 having the formula II or III or IV:

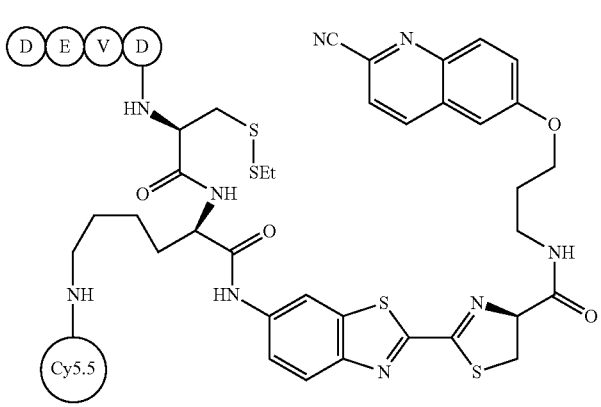

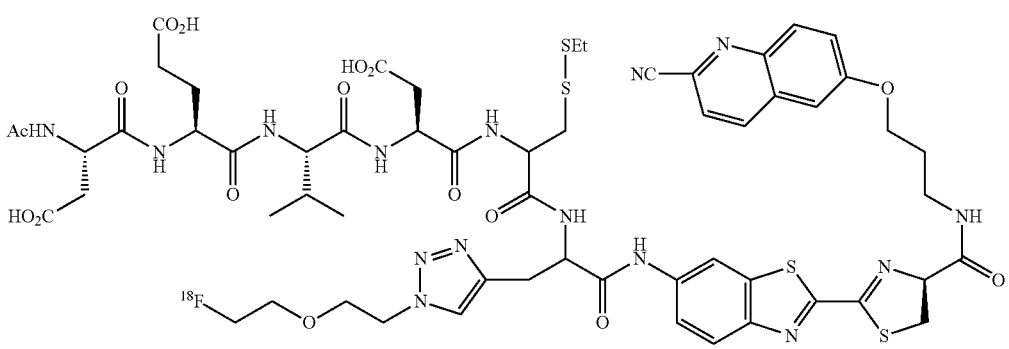

-continued

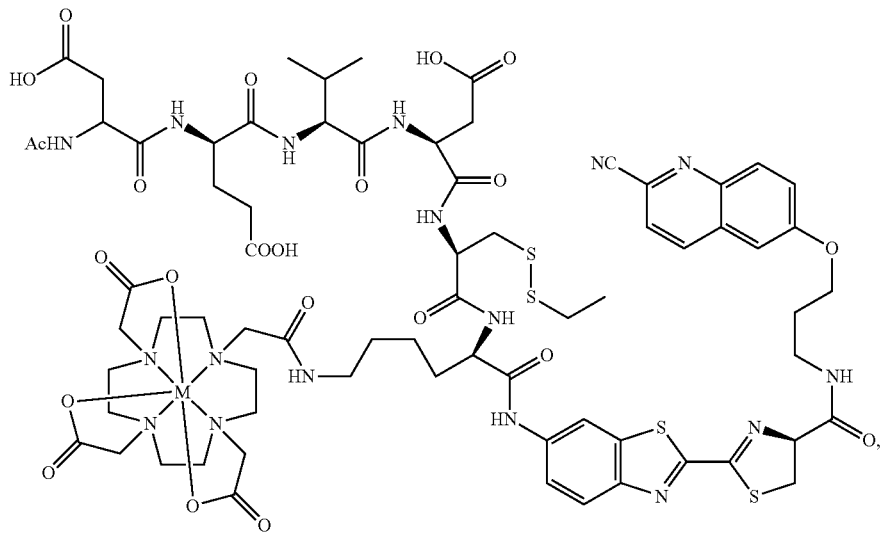

IV wherein, in Formula IV, M is a detectable metal ion.

12. The activatable probe of claim 11, wherein M is gadolinium (Gd), thulium (Tm), europium (Eu), or a combination thereof.

13. A composition comprising the activatable probe of claim 1 and a pharmaceutically acceptable carrier.

14. A nano-aggregation probe, wherein said nano-aggregation probe is an aggregate of an activated probe, wherein said activated probe comprises a self-cyclized molecule having the formula V:

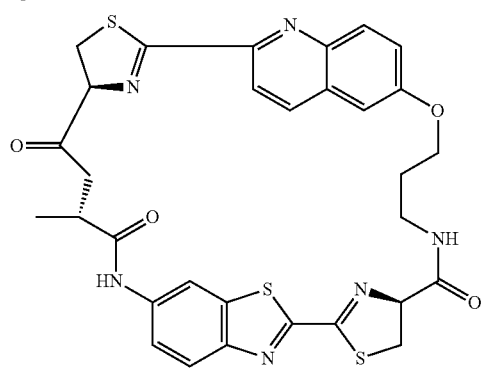

V and a detectable imaging moiety attached thereto.

15. A method of forming a nano-aggregation probe comprising delivering to an apoptotic cell a pharmaceutically acceptable composition comprising an activatable probe and a pharmaceutically acceptable carrier, wherein said activatable probe comprises a detachable capping moiety conjugated to a self-cyclizing molecule, said self-cyclizing molecule comprising a cysteine moiety, a 2-cyano-6-hydroxyquinoline moiety, an amino luciferin scaffold, and a detectable imaging moiety, wherein the detachable capping moiety has an amino acid sequence consisting of L-aspartate-glutamate-valine-aspartate and is selectively cleavable from the self-cyclizing molecule by caspase 3/7, whereupon the activatable probe enters the apoptotic cell, an apotopically-induced caspase 3/7 cleaves the detachable capping moiety from the activatable probe, and said probe aggregates to form the nano-aggregation probe.

16. The method of claim 15, wherein the activatable probe has the formula II, III, or IV:

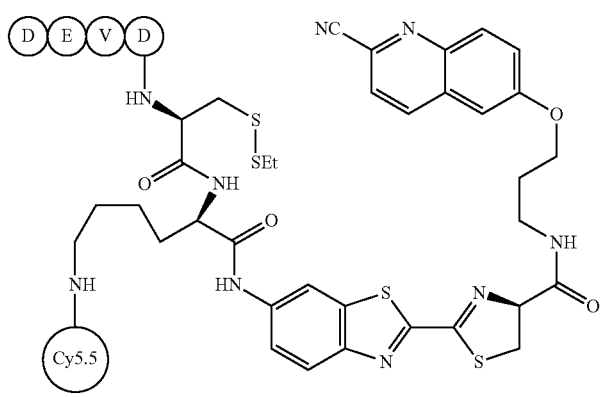

II

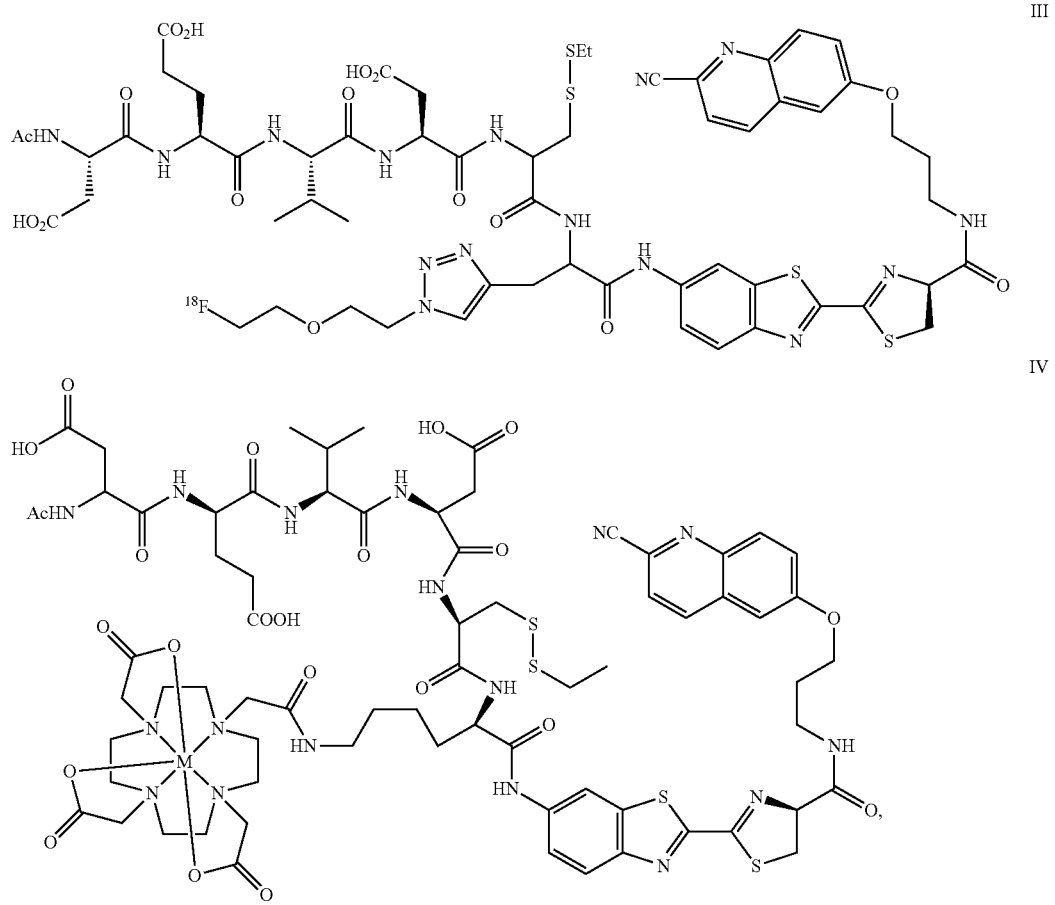

wherein, in Formula IV, M is a detectable metal ion.

17. The method of claim 16, wherein in the activatable probe having the formula IV, M is gadolinium (Gd), thulium (Tm), or europium (Eu).

18. The method of claim 15, wherein the detectable imaging moiety is a fluorophore and the activatable probe further comprises a quenching moiety attached to the detachable capping moiety.

19. A method of detecting an apoptotic cell, the method comprising the steps of:
(i) delivering to the cytoplasm of an animal cell a pharmaceutically acceptable composition comprising an activatable probe, wherein said activatable probe comprises a detachable capping moiety conjugated to a self-cyclizing molecule, said self-cyclizing molecule comprising a cysteine moiety, a 2-cyano-6-hydroxyquinoline moiety, an amino luciferin scaffold, and a detectable imaging moiety, wherein the detachable capping moiety has an amino acid sequence consisting of L-aspartate-glutamate-valine-aspartate and is selectively cleavable from the self-cyclizing molecule by caspase 3/7, whereupon the activatable probe enters the apoptotic cell, an apotopically-induced caspase 3/7 cleaves the detachable capping moiety from the activatable probe, and said probe aggregates to form a nano-aggregation probe; and
(ii) detecting the nano-aggregation probe, thereby determining that the animal cell recipient of the activatable probe is an apoptotic animal cell having an apoptosis-induced caspase 3/7 that cleaved the detachable capping moiety from the activatable probe to form the nano-aggregation probe,
wherein, when the detectable imaging moiety is a fluorophore step (ii) further comprises irradiating the recipient cell with an incident excitation energy, optically detecting an emitted fluorescence, measuring the intensity of said emission, and optionally generating an image of the fluorescence, when the detectable imaging moiety is detectable by positron electron transmission step (ii) further comprises detecting the nano-aggregation probe by PET imaging, and when the detectable imaging moiety is detectable by magnetic resonance imaging step (ii) further comprises detecting the nano-aggregation probe by MRI imaging.

* * * * *